(12) United States Patent
Teng et al.

(10) Patent No.: US 11,457,977 B2
(45) Date of Patent: Oct. 4, 2022

(54) METHOD FOR TREATING DIABETES, DIABETES-ASSOCIATED CONDITION OR DISORDER, OR SYMPTOMS THEREOF

(71) Applicants: Gaojun Teng, Nanjing (CN); Yonghua Dong, Shanghai (CN); Huaqing Yin, Shanghai (CN)

(72) Inventors: Gaojun Teng, Nanjing (CN); Yonghua Dong, Shanghai (CN); Huaqing Yin, Shanghai (CN)

(73) Assignee: Shanghai Golden Leaf Medtech Co., Ltd., Shanghai (CN)

( * ) Notice: Subject to any disclaimer, the term of this patent is extended or adjusted under 35 U.S.C. 154(b) by 750 days.

(21) Appl. No.: 16/271,745

(22) Filed: Feb. 8, 2019

(65) Prior Publication Data

US 2020/0253662 A1 Aug. 13, 2020

(51) Int. Cl.
*A61B 18/14* (2006.01)
*A61B 18/00* (2006.01)
(Continued)

(52) U.S. Cl.
CPC ..... *A61B 18/1492* (2013.01); *A61M 25/0026* (2013.01); *A61N 1/0492* (2013.01);
(Continued)

(58) Field of Classification Search
CPC .. A61B 2018/00267; A61B 2018/0016; A61B 2018/1467; A61B 18/1492; A61B 2018/00511; A61B 2018/00404; A61B 2018/00714; A61B 2018/00666; A61B 2018/00577; A61B 2018/00821;
(Continued)

(56) References Cited

U.S. PATENT DOCUMENTS

| | | | |
|---|---|---|---|
| 7,425,212 B1* | 9/2008 | Danek | A61N 1/403 606/42 |
| 2003/0040772 A1* | 2/2003 | Hyodoh | A61F 2/90 606/200 |

(Continued)

OTHER PUBLICATIONS

Yiqing Song et al. Insulin Sensitivity and Insulin Secretion Determined by Homeostasis Model Assessment (HOMA) and Risk of Diabetes in a Multiethnic Cohort of Women: The Women's Health Initiative Observational Study, Apr. 27, 2007 (Year: 2007).*

(Continued)

*Primary Examiner* — Linda C Dvorak
*Assistant Examiner* — Nicholas S Borsch
(74) *Attorney, Agent, or Firm* — George Guosheng Wang; Upstream Research and Patent LLC

(57) ABSTRACT

The present invention provides a method for treating diabetes, a diabetes-associated condition or disorder, or symptoms thereof suffered by a subject such as a mammal (e.g. a human patient or a pet), comprising (1) placing multiple electrodes within at least one renal artery of the subject and against blood vessel wall of the at least one renal artery; (2) adhering a surface electrode on an external surface such as skin of the subject; and (3) releasing a therapeutically effective amount of radiofrequency energy through at least one of the multiple electrodes to nearby tissues, so as to increase the temperature of the nearby tissues and induce a thermal alteration of the nearby tissues.

10 Claims, 34 Drawing Sheets

(51) Int. Cl.
*A61M 25/00* (2006.01)
*A61N 1/04* (2006.01)
*A61N 1/32* (2006.01)

(52) U.S. Cl.
CPC ...... *A61N 1/32* (2013.01); *A61B 2018/00267* (2013.01); *A61B 2018/00404* (2013.01); *A61B 2018/00511* (2013.01); *A61B 2018/00577* (2013.01); *A61B 2018/00666* (2013.01); *A61B 2018/00714* (2013.01); *A61B 2018/00821* (2013.01); *A61B 2018/00875* (2013.01); *A61B 2018/1467* (2013.01)

(58) Field of Classification Search
CPC ........ A61B 2018/00875; A61B 5/4836; A61B 18/16; A61B 2218/002; A61B 2018/00702; A61B 2018/00791; A61B 2018/00886; A61B 2018/00214; A61B 2018/00434; A61B 2018/00636; A61B 2018/00642; A61B 2018/00648; A61B 2018/00672; A61B 2018/00678; A61B 2018/00684; A61B 2018/00761; A61B 2018/00732; A61B 2018/00797; A61B 2018/00815; A61B 2018/00845; A61M 25/0026; A61N 1/0492; A61N 1/32
See application file for complete search history.

(56) References Cited

U.S. PATENT DOCUMENTS

| | | | | |
|---|---|---|---|---|
| 2008/0255642 | A1* | 10/2008 | Zarins | A61N 7/02 607/99 |
| 2011/0207758 | A1* | 8/2011 | Sobotka | A61K 31/198 514/567 |
| 2012/0101413 | A1* | 4/2012 | Beetel | A61B 18/1492 601/3 |
| 2014/0275993 | A1* | 9/2014 | Ballakur | A61N 5/00 607/96 |
| 2015/0374435 | A1* | 12/2015 | Cao | A61B 5/053 29/601 |
| 2016/0278853 | A1* | 9/2016 | Ogle | A61B 5/283 |
| 2017/0224415 | A1* | 8/2017 | Dong | A61B 18/1492 |

OTHER PUBLICATIONS

Annotated_Dong_Fig_8 (Year: 2022).*

* cited by examiner

| Groups | SHAM | | | LRDN | | | BRDN | | |
|---|---|---|---|---|---|---|---|---|---|
| Time points | W0 | W20 | P | W0 | W20 | P | W0 | W20 | P |
| Weight (kg) | 12.0 ± 0.5 | 18.9 ± 1.9 | <.0001 | 12.0 ± 0.6 | 19.4 ± 2.3 | <.0001 | 12.0 ± 0.7 | 19.2 ± 2.5 | <.0001 |
| TG (mmol/L) | 0.44 ± 0.10 | 2.51 ± 0.41 | <.0001 | 0.43 ± 0.08 | 2.55 ± 0.37 | <.0001 | 0.45 ± 0.13 | 2.52 ± 0.32 | <.0001 |
| TC (mmol/L) | 5.08 ± 0.52 | 7.69 ± 0.76 | <.0001 | 5.06 ± 0.49 | 7.85 ± 1.10 | <.0001 | 5.10 ± 0.50 | 7.78 ± 0.93 | <.0001 |
| LDL (mmol/L) | 2.10 ± 0.20 | 3.91 ± 0.61 | <.0001 | 2.08 ± 0.18 | 3.94 ± 0.48 | <.0001 | 2.12 ± 0.21 | 3.96 ± 0.55 | <.0001 |
| FPG (mmol/L) | 4.16 ± 0.77 | 9.85 ± 1.77 | <.0001 | 4.26 ± 0.60 | 10.08 ± 1.90 | <.0001 | 4.23 ± 0.65 | 10.05 ± 1.89 | <.0001 |
| FIns (mIU/mL) | 2.74 ± 0.46 | 17.78 ± 1.27 | <.0001 | 2.65 ± 0.36 | 18.71 ± 1.92 | <.0001 | 2.68 ± 0.33 | 18.41 ± 1.80 | <.0001 |
| HOMA-IR | 0.51 ± 0.13 | 7.81 ± 1.85 | <.0001 | 0.50 ± 0.10 | 8.34 ± 1.50 | <.0001 | 0.50 ± 0.10 | 8.14 ± 1.43 | <.0001 |
| NE (pg/mL) | 160.5 ± 24.6 | 569.4 ± 89.6 | <.0001 | 155.2 ± 28.4 | 560.9 ± 72.5 | <.0001 | 158.3 ± 20.3 | 579.4 ± 81.2 | <.0001 |
| Ang II (pg/mL) | 1.45 ± 0.08 | 2.22 ± 0.24 | <.0001 | 1.47 ± 0.08 | 2.28 ± 0.28 | <.0001 | 1.49 ± 0.09 | 2.25 ± 0.31 | <.0001 |
| BUN (mmol/L) | 3.18 ± 0.96 | 3.78 ± 0.93 | .5245 | 3.14 ± 0.88 | 3.89 ± 0.74 | .2159 | 3.16 ± 0.82 | 3.82 ± 0.80 | .2932 |
| Cr (μmol/L) | 72.1 ± 11.8 | 76.4 ± 18.0 | 1.0000 | 69.9 ± 13.7 | 75.2 ± 14.9 | 1.0000 | 74.2 ± 15.3 | 72.4 ± 13.1 | 1.0000 |

| Groups | SHAM | LRDN | BRDN | P* | P† | P‡ |
|---|---|---|---|---|---|---|
| Weight (kg) | 12.0 ± 0.5 | 12.0 ± 0.6 | 12.0 ± 0.7 | 1.0000 | 1.0000 | 1.0000 |
| TG (mmol/L) | 0.44 ± 0.10 | 0.43 ± 0.08 | 0.45 ± 0.13 | 1.0000 | 1.0000 | 1.0000 |
| TC (mmol/L) | 5.08 ± 0.52 | 5.06 ± 0.49 | 5.10 ± 0.50 | 1.0000 | 1.0000 | 1.0000 |
| LDL (mmol/L) | 2.10 ± 0.20 | 2.08 ± 0.18 | 2.12 ± 0.21 | 1.0000 | 1.0000 | 1.0000 |
| FPG (mmol/L) | 4.16 ± 0.77 | 4.26 ± 0.60 | 4.23 ± 0.65 | 1.0000 | 1.0000 | 1.0000 |
| FIns (mIU/mL) | 2.74 ± 0.46 | 2.65 ± 0.36 | 2.68 ± 0.33 | 1.0000 | 1.0000 | 1.0000 |
| HOMA-IR | 0.51 ± 0.13 | 0.50 ± 0.10 | 0.50 ± 0.10 | 1.0000 | 1.0000 | 1.0000 |
| NE (pg/mL) | 160.5 ± 24.6 | 165.2 ± 28.4 | 158.3 ± 20.3 | 1.0000 | 1.0000 | 1.0000 |
| Ang II (pg/mL) | 1.45 ± 0.08 | 1.47 ± 0.08 | 1.49 ± 0.09 | 1.0000 | .8019 | 1.0000 |
| BUN (mmol/L) | 3.18 ± 0.96 | 3.14 ± 0.88 | 3.16 ± 0.82 | 1.0000 | 1.0000 | 1.0000 |
| Cr (μmol/L) | 72.1 ± 11.8 | 69.9 ± 13.7 | 74.2 ± 15.3 | 1.0000 | 1.0000 | 1.0000 |

Figure 31

| Time | | W20 | | | | |
|---|---|---|---|---|---|---|
| Groups | SHAM | LRDN | BRDN | P | P* | P** |
| Weight (kg) | 18.9 ± 1.9 | 19.4 ± 2.3 | 19.2 ± 2.5 | 1.0000 | 1.0000 | 1.0000 |
| TG (mmol/L) | 2.51 ± 0.41 | 2.55 ± 0.37 | 2.52 ± 0.32 | 1.0000 | 1.0000 | 1.0000 |
| TC (mmol/L) | 7.69 ± 0.76 | 7.85 ± 1.10 | 7.78 ± 0.93 | 1.0000 | 1.0000 | 1.0000 |
| LDL (mmol/L) | 3.91 ± 0.61 | 3.94 ± 0.48 | 3.96 ± 0.55 | 1.0000 | 1.0000 | 1.0000 |
| FPG (mmol/L) | 9.85 ± 1.77 | 10.09 ± 1.90 | 10.05 ± 1.69 | 1.0000 | 1.0000 | 1.0000 |
| FIns (mIU/mL) | 17.78 ± 1.27 | 18.71 ± 1.92 | 18.41 ± 1.80 | 1.0000 | 1.0000 | 1.0000 |
| HOMA-IR | 7.81 ± 1.85 | 8.34 ± 1.50 | 8.14 ± 1.43 | 1.0000 | 1.0000 | 1.0000 |
| NE (pg/mL) | 569.4 ± 89.6 | 560.9 ± 72.5 | 579.4 ± 81.2 | 1.0000 | 1.0000 | 1.0000 |
| Ang II (pg/mL) | 2.22 ± 0.24 | 2.28 ± 0.28 | 2.25 ± 0.31 | 1.0000 | 1.0000 | 1.0000 |
| BUN (mmol/L) | 3.78 ± 0.93 | 3.89 ± 0.74 | 3.82 ± 0.80 | 1.0000 | 1.0000 | 1.0000 |
| Cr (μmol/L) | 76.4 ± 18.0 | 75.2 ± 14.9 | 72.4 ± 13.1 | 1.0000 | 1.0000 | 1.0000 |

Figure 32

Time: W32

| Groups | SHAM | LRDN | BRDN | P | P' | P* |
|---|---|---|---|---|---|---|
| Weight (kg) | 20.3 ± 2.4 | 20.0 ± 2.1 | 19.8 ± 1.6 | 1.0000 | 1.0000 | 1.0000 |
| TG (mmol/L) | 2.62 ± 0.33 | 2.59 ± 0.27 | 2.55 ± 0.40 | 1.0000 | 1.0000 | 1.0000 |
| TC (mmol/L) | 8.08 ± 1.10 | 8.13 ± 0.77 | 8.02 ± 0.91 | 1.0000 | 1.0000 | 1.0000 |
| LDL (mmol/L) | 4.09 ± 0.64 | 4.03 ± 0.58 | 3.99 ± 0.53 | 1.0000 | 1.0000 | 1.0000 |
| FPG (mmol/L) | 9.64 ± 1.57 | 7.65 ± 1.18 | 5.12 ± 1.08 | .0043 | <.0001 | .0003 |
| FIns (mIU/mL) | 16.19 ± 1.43 | 10.08 ± 1.64 | 5.07 ± 1.13 | <.0001 | <.0001 | <.0001 |
| HOMA-IR | 6.95 ± 1.33 | 3.40 ± 0.60 | 1.15 ± 0.33 | <.0001 | <.0001 | <.0001 |
| NE (pg/mL) | 600.6 ± 93.6 | 471.9 ± 62.7 | 364.2 ± 47.5 | .0008 | <.0001 | .0047 |
| Ang II (pg/mL) | 2.54 ± 0.28 | 2.17 ± 0.27 | 1.78 ± 0.20 | .0080 | <.0001 | .0040 |
| BUN (mmol/L) | 4.28 ± 1.00 | 4.33 ± 0.90 | 4.35 ± 0.96 | 1.0000 | 1.0000 | 1.0000 |
| Cr (μmol/L) | 73.9 ± 12.3 | 79.2 ± 18.8 | 77.2 ± 15.9 | 1.0000 | 1.0000 | 1.0000 |

Figure 33

METHOD FOR TREATING DIABETES, DIABETES-ASSOCIATED CONDITION OR DISORDER, OR SYMPTOMS THEREOF

FIELD OF THE INVENTION

The present invention generally relates to a method for treating diabetes, a diabetes-associated condition or disorder, or symptoms thereof. A related disclosure was made by the inventor or joint inventor 1 year or less before the effective filing date of the present invention, and the disclosure shall not be prior art to the present invention under 35 U.S.C. 102 (a)(1). The disclosure is a publication of Tao Pan et al. "Effects of Multi-Electrode Renal Denervation on Insulin Sensitivity and Glucose Metabolism in a Canine Model of Type 2 Diabetes Mellitus", J Vasc Interv Radiol.; 29(5):731-738; May 2018.

BACKGROUND OF THE INVENTION

Diabetes mellitus is a serious lifelong metabolic disease that is defined by the presence of chronically elevated levels of blood glucose (hyperglycemia). This disease often leads to blindness, heart and blood vessel disease, strokes, kidney failure, amputations, and nerve damage. This state of hyperglycemia is the result of a relative or absolute lack of activity of the peptide hormone, insulin. Insulin is produced and secreted by the β cells of the pancreas. Insulin promotes glucose utilization, protein synthesis, and the formation and storage of carbohydrate energy as glycogen. Glucose is stored in the body as glycogen, a form of polymerized glucose, which may be converted back into glucose to meet metabolism requirements. Under normal conditions, insulin is secreted at both a basal rate and at enhanced rates following glucose stimulation, all to maintain metabolic homeostasis by the conversion of glucose into glycogen.

The term diabetes mellitus encompasses several different hyperglycemic states. These states include Type 1 (insulin-dependent diabetes mellitus or IDDM) and Type 2 (non-insulin dependent diabetes mellitus or NIDDM) diabetes. Type 1 diabetes is associated with deficient, reduced, or nonexistent levels of insulin that are insufficient to maintain blood glucose levels within the physiological range. Type 1 diabetes affects 10% of diabetic patients, and is characterized by a depletion of pancreatic insulin supply, resulting from an autoimmune destruction of the insulin-producing beta-cells. Treatment requires the administration of exogenous insulin in order to meet energy demands. Type 2 diabetes, which affects the vast majority ~90% of the diabetic population, occurs when the body cannot effectively utilize the insulin that is being produced. The pathophysiology of Type 2 diabetes mellitus (T2DM) includes insulin resistance, hyperglycemia, and a variable degree of insulin secretory deficiency. Type 2 diabetes is an increasingly prevalent disease of aging. It is initially characterized by decreased sensitivity to insulin or insulin resistance and a compensatory elevation in circulating insulin concentrations, the latter of which is required to maintain normal blood glucose levels. Increased insulin levels are caused by increased secretion from the pancreatic β cells, and the resulting hyperinsulinemia is associated with cardiovascular complications of diabetes. As insulin resistance worsens, the demand on the pancreatic β cells steadily increases until the pancreas can no longer provide adequate levels of insulin, resulting in elevated levels of glucose in the blood. Ultimately, overt hyperglycemia and hyperlipidemia occur, leading to the devastating long-term complications associated with diabetes, including cardiovascular disease, renal failure, and blindness.

A number of factors may contribute to an impaired insulin response, including decreases in insulin production, insulin secretion or insulin sensitivity. In the initial stages of Type 2 diabetes, most patients' beta cells undergo a compensatory expansion of functional mass and insulin output. As the disease progresses, this compensatory response eventually fails and pharmaceutical intervention is required in order to adequately regulate glucose levels. However, with further disease progression, the effectiveness of initially prescribed therapeutics generally declines, thus requiring additional method to be incorporated into the treatment regimen.

Many studies have indicated that the sympathetic nervous system plays a pivotal part in the development of insulin resistance and T2DM, and that renal nerves participate in blood pressure control, renal function, and glucose metabolism. It has been shown that increased sympathetic nervous system activation plays a significant role in insulin resistance, and insulin resistance can induce an increase in sympathetic nervous system activation.

In the past decade, catheter-based renal denervation (RDN), an ablation technique targeting renal sympathetic nerves, has been used for resistant hypertension. However, the efficacy of RDN in the treatment of resistant hypertension is still controversial. Early studies have shown improvements in insulin sensitivity and glucose metabolism, as well as lower blood pressure and sympathetic nerve activity after RDN, which might be a combination of the beneficial effects of sympathoinhibition and the reduced release of noradrenaline on regional hemodynamics. In some animal studies in which RDN was performed either surgically or chemically, reduced sympathetic nerve activity and elevated insulin sensitivity were observed. There was no significant reduction in fasting glucose and no effect on systemic sympathetic activity demonstrated in the DREAMS study, which used the Symplicity Flex device with monopolar electrodes for RDN.

In a recent clinical trial of multi-electrode RDN on patients with metabolic syndrome, the authors clarified that multi-electrode RDN could reduce elevated sympathetic nerve activity and restore the normal neural response to oral glucose loading (Tsioufis C, Dimitriadis K, Kasiakogias A, et al. Effects of multi-electrode renal denervation on elevated sympathetic nerve activity and insulin resistance in metabolic syndrome. J Hypertens 2017; 35: 1100-1108). Nonetheless, the effects of multi-electrode RDN for the treatment of T2DM in an experimental animal and the pathophysiology of multi-electrode RDN on T2DM have not been systematically examined.

Advantageously, the present invention provides numerous embodiments, one of which includes using multi-electrode catheter-based RND to improve insulin sensitivity and glucose metabolism in a canine model of T2DM.

SUMMARY OF THE INVENTION

One aspect of the invention provides a method for treating diabetes, a diabetes-associated condition or disorder, or symptoms thereof suffered by a subject such as a mammal (e.g. a human patient or a pet). The method includes steps of:

(1) placing multiple electrodes within at least one renal artery of the subject and against blood vessel wall of the at least one renal artery;

(2) adhering a surface electrode on an external surface such as skin of the subject; and (3) releasing a therapeutically effective amount of radiofrequency energy through at least one of the multiple electrodes to nearby tissues, so as to increase the temperature of the nearby tissues and induce a thermal alteration of the nearby tissues. The terms "treating" and "therapeutically effective" refer to reversing, alleviating, inhibiting the progress of, or preventing the diabetes or the diabetes-associated condition or disorder, or the symptoms thereof in the subject.

The above features and advantages and other features and advantages of the present invention are readily apparent from the following detailed description of the best modes for carrying out the invention when taken in connection with the accompanying drawings.

BRIEF DESCRIPTION OF THE SEVERAL VIEWS OF THE DRAWINGS

The present invention is illustrated by way of example, and not by way of limitation, in the figures of the accompanying drawings and in which like reference numerals refer to similar elements. All the figures are schematic and generally only show parts which are necessary in order to elucidate the invention. For simplicity and clarity of illustration, elements shown in the figures and discussed below have not necessarily been drawn to scale. Well-known structures and devices are shown in simplified form, omitted, or merely suggested, in order to avoid unnecessarily obscuring the present invention.

FIG. 18 shows the Diabetes Mellitus Model Development in the SHAM, LRDN, and BRDN groups in accordance with an exemplary embodiment of the present invention.

Figure 30:
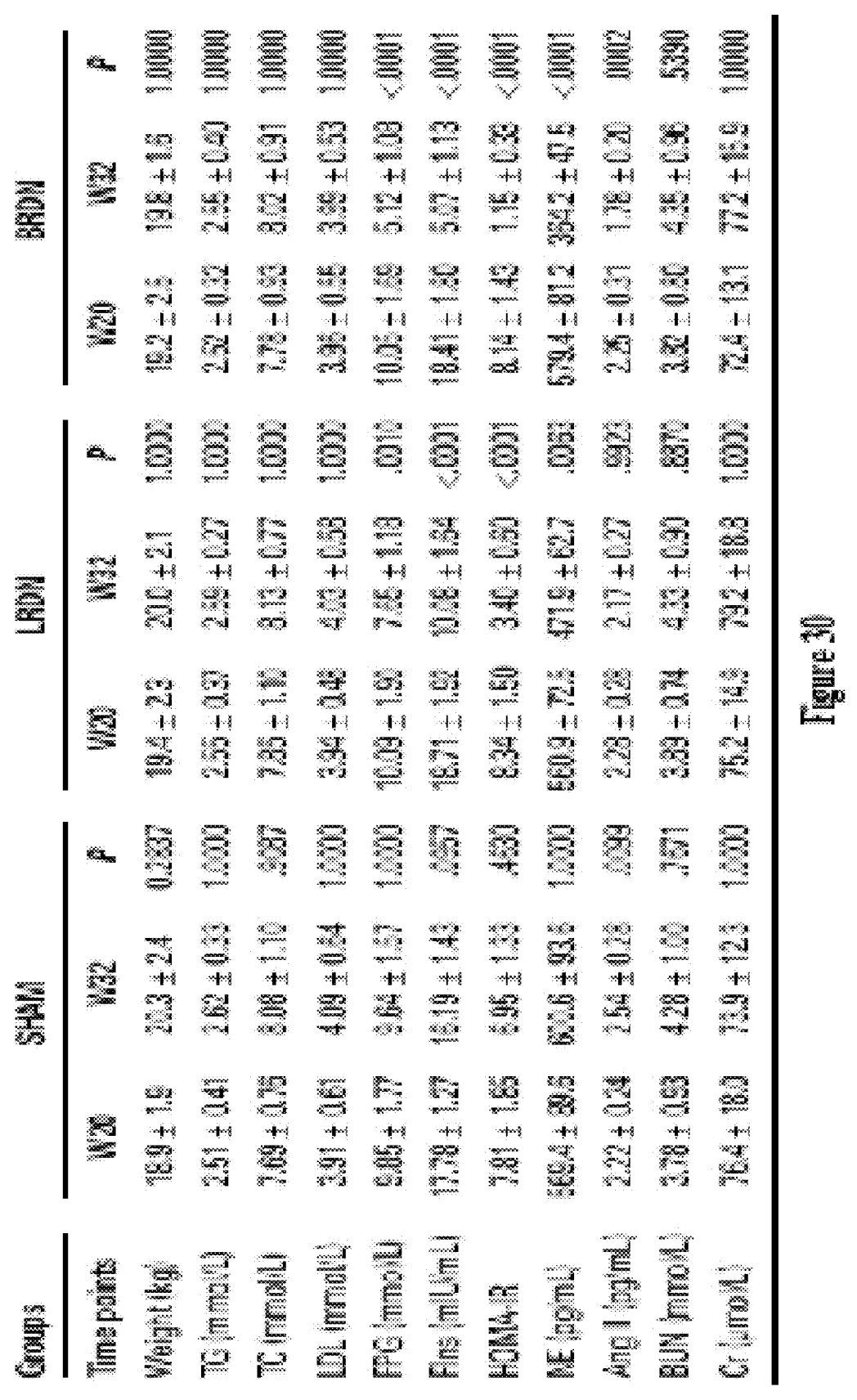

FIG. 30 is a summary of the changes after the procedure in the SHAM, LRDN, and BRDN groups in accordance with an exemplary embodiment of the present invention.

FIG. 31 is a summary of the data comparisons among the SHAM, LRDN, and BRDN Groups at W0 in accordance with an exemplary embodiment of the present invention.

FIG. 32 is a summary of the data comparisons among the SHAM, LRDN, and BRDN Groups at W20 in accordance with an exemplary embodiment of the present invention.

FIG. 33 is a summary of the data comparisons among the SHAM, LRDN, and BRDN Groups at W32 in accordance with an exemplary embodiment of the present invention.

DETAILED DESCRIPTION OF THE PREFERRED EMBODIMENT

In the following description, for the purposes of explanation, numerous specific details are set forth in order to provide a thorough understanding of the present invention. It is apparent, however, to one skilled in the art that the present invention may be practiced without these specific details or with an equivalent arrangement.

Where a numerical range is disclosed herein, unless otherwise specified, such range is continuous, inclusive of both the minimum and maximum values of the range as well as every value between such minimum and maximum values. Still further, where a range refers to integers, only the integers from the minimum value to and including the maximum value of such range are included. In addition, where multiple ranges are provided to describe a feature or characteristic, such ranges can be combined.

Figure 1A:
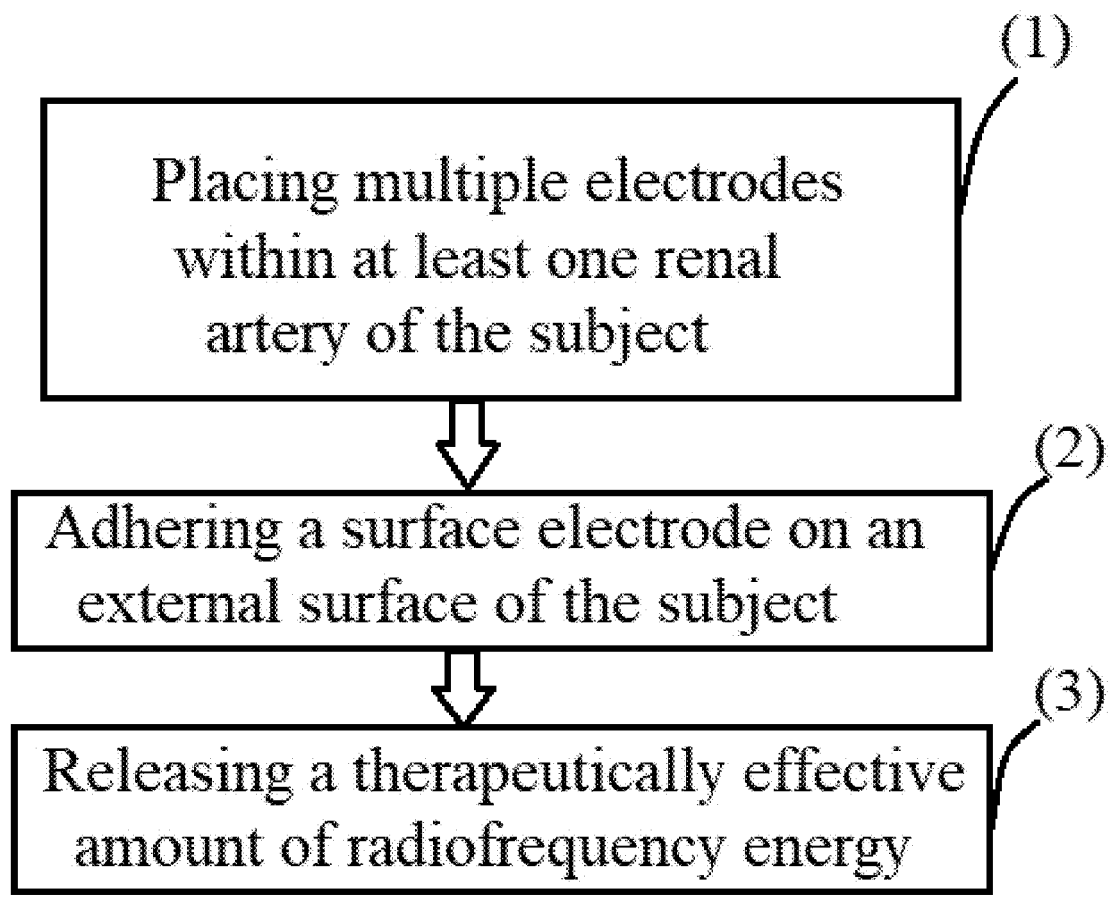
FIG. 1A is a flow chart of the method according to an exemplary embodiment of the present invention.
Figure 1B:
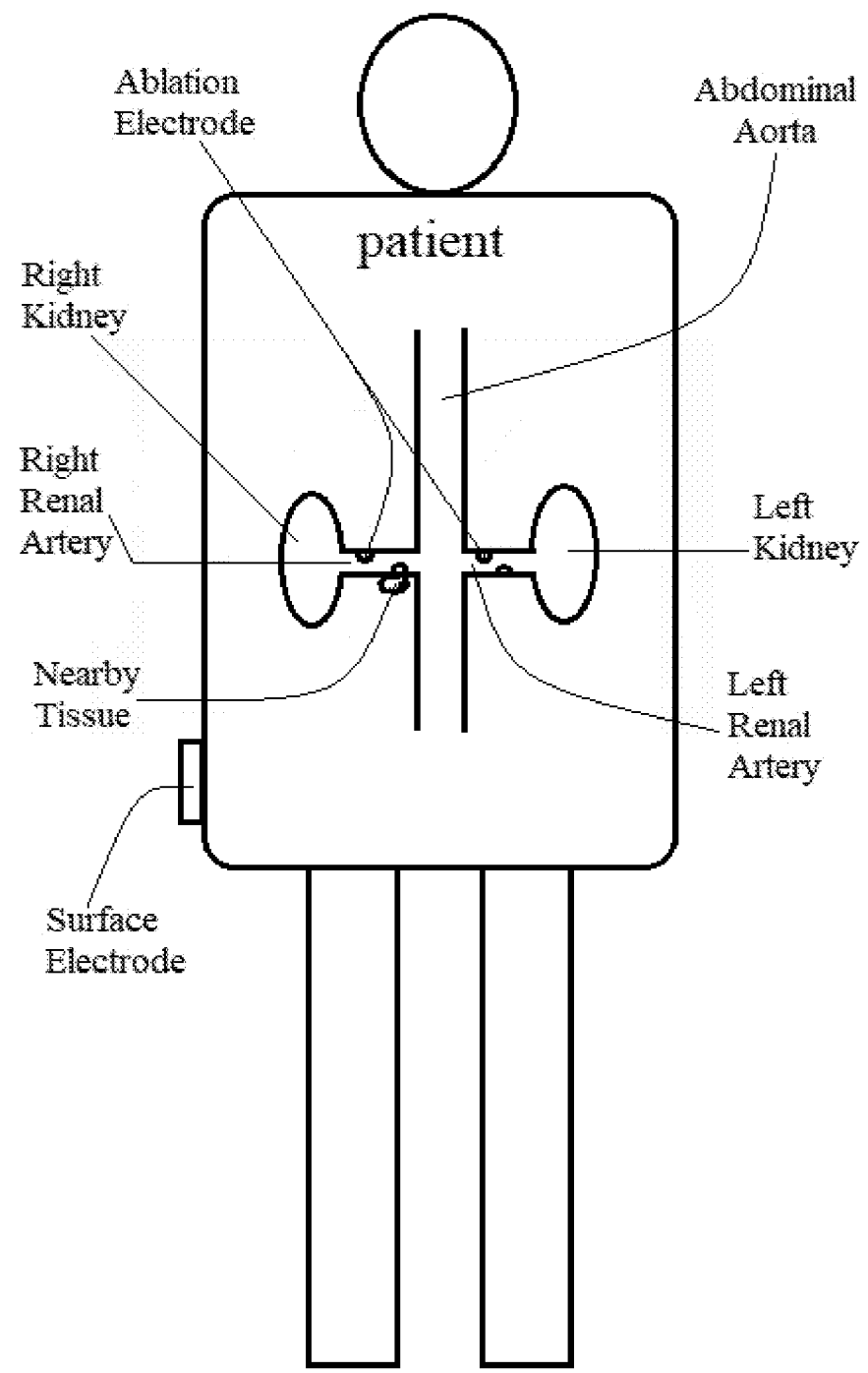
FIG. 1B illustrates the step of placing multiple electrodes within at least one renal artery and against blood vessel wall in an exemplary embodiment of the present invention.

As shown in FIGS. 1A and 1B, the present invention provides a method for treating diabetes such as Type 2 diabetes, a diabetes-associated condition or disorder, or symptoms thereof suffered by a subject such as a mammal (e.g. a human patient or a pet such as a dog). The method includes step (1) placing multiple electrodes within at least one renal artery of the subject and against blood vessel wall of the at least one renal artery; step (2) adhering a surface electrode on an external surface such as skin of the subject; and step (3) releasing a therapeutically effective amount of radiofrequency energy through at least one of the multiple electrodes to nearby tissues, so as to increase the temperature of the nearby tissues and induce a thermal alteration of the nearby tissues. Said treating and said "therapeutically effective" refer to reversing, alleviating, inhibiting the progress of, or preventing the diabetes or the diabetes-associated condition or disorder, or the symptoms thereof in said subject. The at least one renal artery includes left renal artery only, right renal artery only, or preferably both left and right renal arteries Various embodiments of the present invention use the femoral artery for the endovascular method. Endovascular diagnostic and therapeutic procedures are generally performed through the femoral artery. Some of the reasons for this generalized approach include its location, easy approach for puncture and hemostasis, low rate of complications, technical ease, wide applicability and relative patient comfort. Femoral puncture also allows access to virtually all of the arterial territories and affords favorable ergonomics for the operator in most instances.

In step (2), a surface electrode (or external electrode) is adhered on an external surface such as skin of the patient. The method may further include a step of adjusting or changing the adhesion position of the surface electrode on the back or butt of the patient (preferably not on the belly of the patient) to vary the impedance between the surface electrode and a given electrode within the at least one renal artery until the impedance falls within a desired range, for example, until the impedance is <400Ω, such as 300-400 ΩOhms, before step (2).

In Step (3), the radiofrequency energy may be released through an alternating current of 460-470 KHz such as 465 KHz between the surface electrode and a given electrode within the renal artery. The radiofrequency energy may be released with a temperature threshold setting of 60° C. to ensure that collagen does not denature, tissue does not shrink, and cell wall does not break, in the nearby tissue. In general, when tissue temperature rises above about 50° C., protein is permanently damaged. If heated over about 65° C., collagen denatures and tissue shrinks. If heated over about 65° C. and up to 100° C., cell walls break and oil separates from water. Above about 100° C., tissue desiccates. In preferred embodiments, the radiofrequency energy is released with a temperature threshold setting of 60° C. and a period of 30-90 seconds such as 50-70 seconds e.g. 60 seconds to ensure that in the nearby tissue, collagen does not denature, tissue does not shrink, and cell wall does not break.

The thermal heating effects according to the present invention can include both thermal ablation and non-ablative thermal alteration or damage (e.g., via sustained heating and/or resistive heating). Desired thermal heating effects may include raising the temperature of the target segment above a desired threshold to achieve non-ablative thermal alteration, and/or above a higher temperature to achieve ablative thermal alteration. For example, the target temperature can be above body temperature (e.g., approximately 37° C.) but less than about 45° C. for non-ablative thermal alteration, or the target temperature can be about 45-60° C. or higher for the ablative thermal alteration. The time period for non-ablative thermal alteration (<45° C.) is defined as Tna, the time period for ablative thermal alteration (≥45° C.) is defined as Ta, and the ratio between the two is defined as Rna/a.

In step (3), the radiofrequency energy may be released for a continuous period of 30-90 seconds for each of the multiple electrodes one by one, which protocol is defined as one session. Step (3) may include two, three, four, or more such sessions that are separately carried out. The thermal alteration comprises non-ablative thermal alteration, ablative thermal alteration, or any combination thereof; and wherein the thermal alteration produces a lesion with a depth of 5-8 mm or 5.9-6.9 mm such as about 6.4 mm in the nearby tissues.

In preferred embodiments, during and/or after step (3), the method of the invention triggers/stimulates further steps or mechanisms in the subject, for example, suppressing gluconeogenetic genes, suppressing expression of G6Pase and PEPCK, reducing hepatic PEPCK and G6Pase protein levels, and improving glucose metabolism.

In preferred embodiments, during and/or after step (3), the method of the invention triggers/stimulates further steps or mechanisms in the subject, for example, enhancing the phosphorylation of InsR, increasing the phosphorylation of insulin receptors—AKT in the liver, stimulating liver insulin signaling, altering insulin signaling pathways, and increasing insulin sensitivity.

In preferred embodiments, during and/or after step (3), the method of the invention triggers/stimulates further steps or mechanisms in the subject, for example, decreasing fasting plasma glucose level of the subject down to less than 55% of that without the treatment three months after step (3) is carried out, such as decreasing from 9.64 mmol/L down to 5.12 mmol/L.

In preferred embodiments, during and/or after step (3), the method of the invention triggers/stimulates further steps or mechanisms in the subject, for example, comprising decreasing fasting insulin level of the subject down to less than 35% of that without the treatment three months after step (3) is carried out, such as decreasing from 16.19 mIU/mL down to 5.07 mIU/mL.

In preferred embodiments, during and/or after step (3), the method of the invention triggers/stimulates further steps or mechanisms in the subject, for example, decreasing homeostasis-model assessment of insulin resistance (HOMA-IR) of the subject down to less than 20% of that without the treatment three months after step (3) is carried out, such as decreasing from 6.95 down to 1.15.

In preferred embodiments, during and/or after step (3), the method of the invention triggers/stimulates further steps or mechanisms in the subject, for example, damaging nerve and decreasing renal tissue noradrenaline of the subject down to less than 90% (e.g. <80%, <70%, <35%, or <15%) of that without the treatment three months after step (3) is carried out, such as decreasing from 585.5 pg/g down to 187.7 pg/g or 66.9 pg/g.

In preferred embodiments, during and/or after step (3), the method of the invention triggers/stimulates further steps or mechanisms in the subject, for example, maintaining integrity of the at least one renal artery by introducing no dissection, no aneurysm, no thrombus, no rupture, and no renal function impairment in the artery, after step (3) is carried out.

According to some embodiments of the invention, an external control unit can be coupled to a catheter to provide RF energy and temperature monitoring. An electrode activation circuitry may be configured to control activation and deactivation of the multiple electrodes in accordance with a predetermined energy delivery protocol and in response to signals received from temperature measuring circuitry.

According to some embodiments, temperature at or near the electrode and/or electrode-tissue can be measured using an optical fiber that extends along the catheter shaft and terminates at or near the electrode assembly. In some configurations, temperature measurements can be made by an optical fiber that has evanescent loss that varies with temperature, or by analyzing the Raman scattering of the optical fiber.

Temperature sensors provide for continuous monitoring of tissue temperatures, and RF generator power is automatically adjusted so that the target temperatures are achieved and maintained. An impedance sensor arrangement may be used to measure and monitor electrical impedance during the process, and the power and timing of the RF generator may be moderated based on the impedance measurements or a combination of impedance and temperature measurements.

Temperature-measurement devices are for example, thermocouples, thermistors, and other temperature sensors. Following types of thermocouples may be used in the present invention: nickel alloy, platinum/rhodium alloy, tungsten/rhenium alloy, gold/iron alloy, noble metal alloy, platinum/molybdenum alloy, iridium/rhodium alloy, pure noble metal, Type K, Type T, Type E, Type J, Type M, Type N, Type B, Type R, Type S, Type C, Type D, Type G, and/or Type P.

According to some embodiments, impedance can be measured and monitored for each electrode, in a unipolar configuration, or between electrode assemblies, in a bipolar configuration. Changes in tissue impedance due to heating and ablation can be monitored by an external control unit, alone or along with temperature monitoring, to enable automatic or semi-automatic control of an ablation procedure.

Without being bound to any particular theory, it is believed that the process of the present invention causes controllable injury to nerves within the walls of the renal artery, or in the neighborhood of the renal artery. The nerves also include those unassociated with any walls of blood vessels. The nerves may even include those within the spine of the patient. The "controllable injury" according to the present invention includes a spectrum of nerve injuries: (1) transient and reversible nerve injury, (2) more severe than (1) but remain reversible nerve injury if the process of the invention is terminated in a timely manner; and (3) severe and irreversible nerve injury, resulting in permanent cessation of nerve activity.

As used herein, the terms "distal" and "proximal" define a position or direction with respect to the treating clinician or clinician's control device (e.g., a handle assembly). "Distal" or "distally" refers to a position distant from or in a direction away from the clinician or clinician's control device. "Proximal" or "proximally" refers a position near or in a direction toward the clinician or clinician's control device.

The present invention provides a method for altering/ablating extravascular target tissue from within a blood vessel, particularly within the patient's renal artery. With the treatment according to the present invention, the extent and relative permanency of nerve injury may be tailored to achieve a desired reduction in sympathetic nerve activity (including a partial or complete block) and to achieve a desired degree of permanency (including temporary or irreversible injury).

In preferred embodiments, the multiple electrodes consist of six electrodes configured to create interrupted spiral but full circumferential lesions on internal wall of the renal artery of the patient. The multiple electrodes used in the present method may be a part of any suitable catheter apparatus, for example, the catheter device as described in Chinese Patent Application 201410035836.5 published as CN 103767787A, the content of which is incorporated herein in its entirety.

Figure 1C:
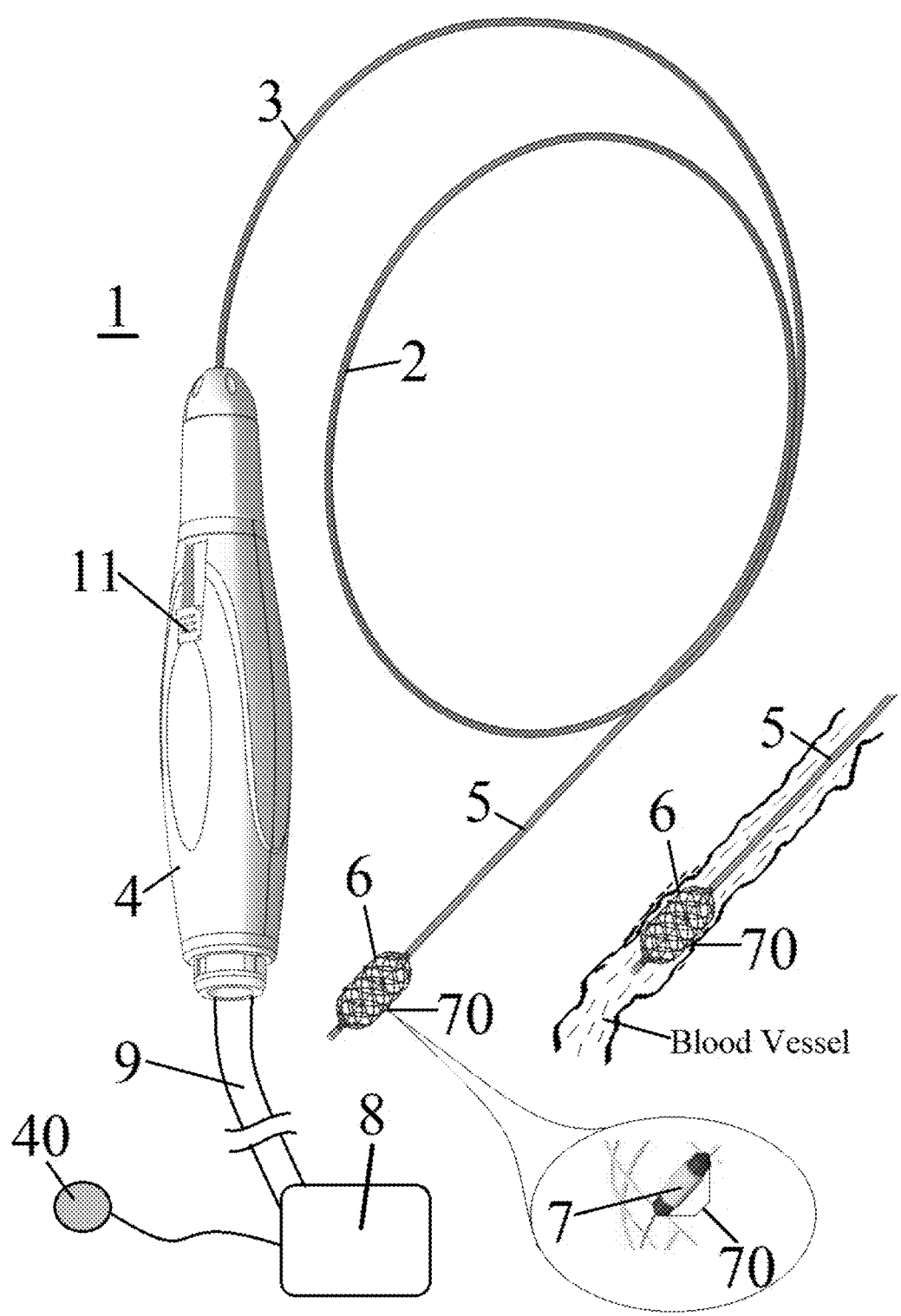
FIG. 1C schematically shows a catheter system used in an exemplary embodiment of the present invention.

In various exemplary embodiments, the multiple electrodes used in the present method are six electrodes in a catheter apparatus as shown in FIG. 1C. The system includes a catheter apparatus 1 that can be operably coupled to an energy source or energy generator 8. The catheter apparatus 1 includes an elongated shaft 2 having a proximal portion 3, a handle assembly 4 at a proximal region of the proximal portion 3, and a distal portion 5 extending distally relative to the proximal portion 3. The catheter apparatus 1 further includes an expandable carrier 6 carrying at least one therapeutic assembly 70 including a therapeutic member 7 for intravascular treatment. The carrier 6 is located at, or proximate to, the distal portion 5 of the elongated shaft 2.

Figure 2:
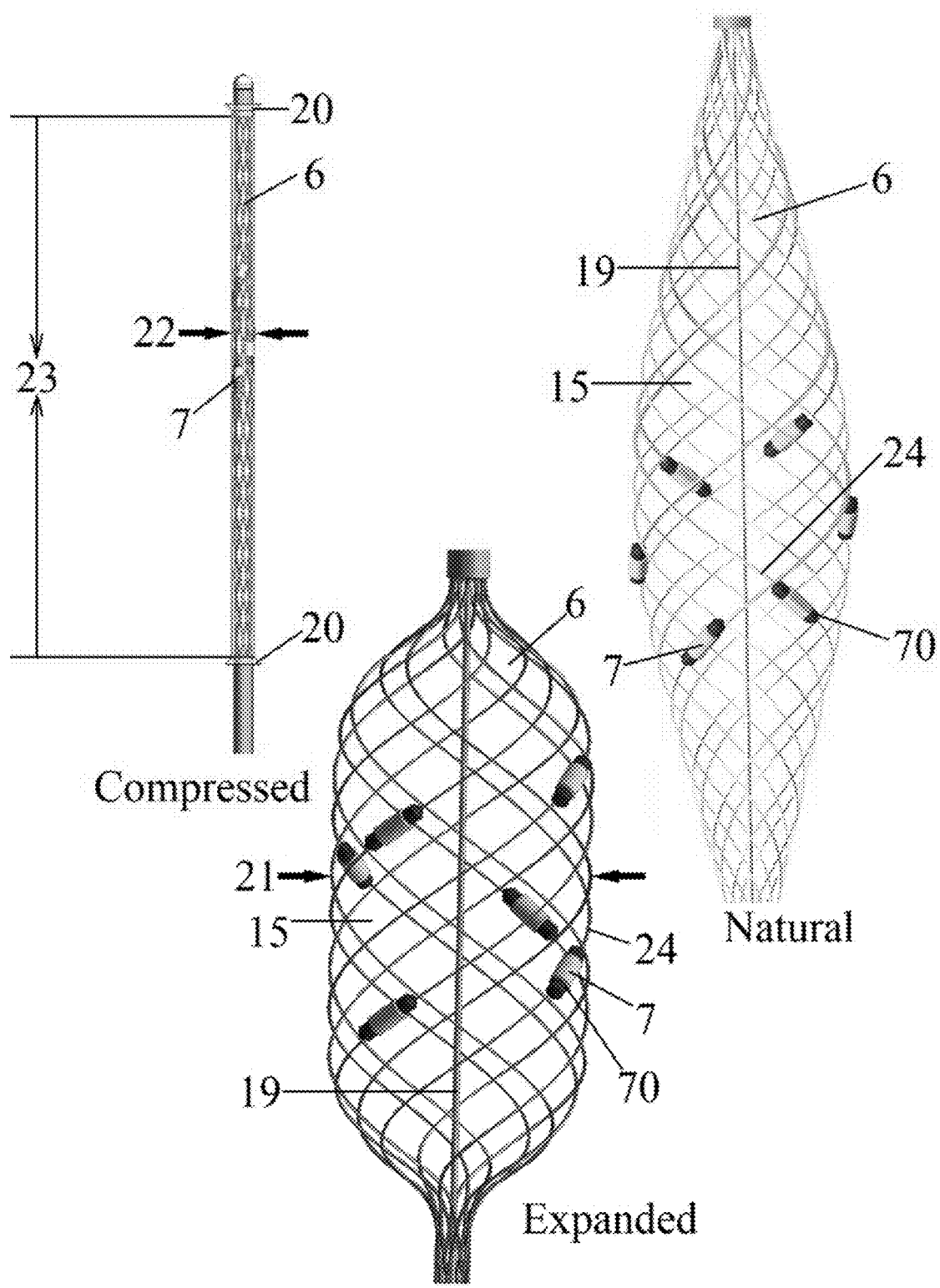
FIG. 2 shows different configurations of the carrier used in an exemplary embodiment.

As shown in FIG. 2, the carrier 6 is configured to be delivered to a blood vessel in a compressed (or low-profile, or delivery, or compacted) configuration. The carrier 6 in compressed configuration can be stored within a protective tube 20. Upon delivery to the target site within the blood vessel, the carrier 6 may be deployed into an expanded (or treatment, or deployed) configuration, bringing the therapeutic member 7 in contact with the walls of the vessel. In various embodiments, therapeutic member 7 is configured to deliver energy at the treatment site and provide therapeutically-effective electrically- and/or thermally-induced medical effect. In some embodiments, the carrier 6 may be placed in the deployed configuration or arrangement via remote actuation, e.g., via an actuator 11, such as a knob, pin, or lever carried by the handle 4, as shown in FIG. 1C. In other embodiments, however, the carrier 6 may be movable between the delivery and deployed configurations using other suitable mechanisms or techniques (e.g., self-expanding). For example, the carrier 6 may be deployed into a natural configuration without any external force imposed upon it, i.e. carrier 6 is neither compressed nor expanded, also bringing the therapeutic member 7 in contact with the walls of the vessel. In some embodiments, a delivery sheath (not shown) is used for deploying the carrier 6. The carrier 6 can self-expand and lengthen when the delivery sheath is retracted.

The carrier 6 is capable of expanding to a maximum diameter 21 that is larger than a collapsed diameter, as shown in FIG. 2. Further, the carrier 6 may be sized so that the maximum diameter 21 is larger than the lumen diameter of the blood vessel. In some embodiments, when inserted into a patient, the carrier 6 expands radially to span the vessel lumen. In other examples, the largest transverse dimension of the carrier 6 is approximately or slightly less than the diameter of the blood vessel lumen, so as to give room to other parts projecting outwardly from the carrier 6. A slight amount of vessel distension may be caused without undue injury and the carrier 6 may expand such that its largest transverse dimension is slightly more than the natural lumen diameter of the blood vessel, or such that the therapeutic member 7 is slightly pressed into the wall of the blood vessel. Sometimes, the carrier 6 that causes slight and non-injurious distension of an artery wall may advantageously provide stable contact force between the therapeutic member 7 and the artery wall and/or hold the therapeutic member 7 in place even as the artery moves with respiratory motion and pulsing blood flow. In some embodiments, the blood vessel lumen diameter can restrict the expansion of the carrier 6 and provide a limit to the maximum diameter 21. This restriction can cause the carrier 6 to form more of a cylindrical tapered shape than a prolate spheroid shape. Because the lumen diameter varies from patient to patient, the carrier 6 may be capable of assuming a range of diameters between the compressed diameter 22 and the maximum diameter 21, as shown in FIG. 2.

The carrier 6 may be characterized by its length 23 along the axis of the elongated shaft 2 or control wire 19. As the carrier 6 expands; its diameter 21 increases and its length 23 decreases. That is, when the carrier 6 expands, its distal end moves axially towards its proximal end. Accordingly, the expanded length 23 is shorter than the unexpanded or natural, or collapsed or compressed, length. In some embodiments, only the proximal end or only the distal end of the carrier 6 is fixedly coupled to the elongated shaft 2. In such a configuration, the distance between the proximal end and the distal end of the carrier 6 changes as the carrier 6 moves between the expanded and collapsed configurations.

The dimensions of the carrier 6 are influenced by its physical characteristics and its configuration (e.g., expanded vs. unexpanded), which in turn may be selected with blood vessel geometry in mind. The expanded configuration length 23 of the carrier 6 is less than the corresponding or counterpart length 23 in the compressed configuration. In some embodiments, the expanded configuration length 23 may be less than about 50%, 55%, 60%, 65%, 70%, 75%, 80%, 85%, or 90% of the corresponding or counterpart compressed length 23. Further, in some embodiments, the expanded configuration diameter 21 may be at least 1.2×, 1.25×, 1.5, 1.75×, 2×, 2.25×, 2.5×, 2.75×3×, 3.25×, 3.5×, 3.75×, 4×, 4.25×, 4.5×, 4.75×, 5×, 10×, 15×, 20×, 30× or 40× of the compressed diameter 22.

The axial length 23 of the carrier 6 may be selected to be no longer than a patient's target blood vessel. A blood vessel may constrict, dilate or move in response to blood flow changes or changes in a patient's breathing, etc. The carrier 6 may be selected to be used in conjunction with a particular blood vessel lumen diameter, taking into account that this lumen diameter may change (e.g., up to 20%) during the time that the carrier 6 is in place. As such, the largest diameter 21 of the carrier 6 may be sufficiently oversized relative to the blood vessel to allow for additional expansion during use. In one embodiment, the largest diameter 21 may be at least 1.2×, 1.5×, or 2× an estimated lumen diameter of the targeted blood vessel. In addition, stable contact with the blood vessel is facilitated by the contact force of the carrier 6 against the blood vessel wall. This contact force is influenced by the materials and construction of the carrier 6. The carrier 6 may be fabricated with super-elastic material such as nickel titanium alloy (nitinol) or composite nitinol with polymer coating for insulation.

Referring to FIGS. 1C and 2, the carrier 6 may carry two or more therapeutic members 7 for intravascular treatment. The therapeutic member 7 may be for example an electrode or a heating element, which is configured to deliver energy such as electrical energy, radiofrequency (RF) electrical energy, pulsed electrical energy, and thermal energy to a target blood vessel after being advanced via a catheter along a percutaneous transluminal path. For example, an energy generator 8 may supply a continuous or pulsed RF electric field to the therapeutic member 7. Although a continuous delivery of RF energy is desirable, the application of RF energy in pulses may allow the application of relatively higher instantaneous power (e.g., higher power), longer or shorter total duration times, and/or better controlled intravascular therapy. Pulsed energy may also allow for the use of a smaller therapeutic member 7.

For example, the purposeful application of energy to tissue by therapeutic member(s) 7 may induce one or more desired thermal heating effects on localized regions of the blood vessel and adjacent regions thereof. The thermal heating effects can include both thermal ablation and non-ablative thermal alteration or damage (e.g., via sustained heating and/or resistive heating). Desired thermal heating effects may include raising the temperature of target tissue above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher (such as 60° C.) for the ablative thermal alteration.

When therapeutic members 7 are employed, they may function, for example deliver power, independently (i.e., may be used in a monopolar fashion), either simultaneously, selectively, or sequentially, and/or may deliver power between any desired combination of the members 7 (i.e., may be used in a bipolar fashion). Furthermore, the doctor optionally may be permitted to choose which therapeutic member(s) 7 are used to function medically, such as power delivery in order to form highly customized lesion(s) within the blood vessel, as desired. For example, an RF electric field causes lesion formation via resistive heating of tissue exposed to the electric field. As will be described in more details, the therapeutic member 7 is mounted or integrated into the carrier 6. As the carrier 6 is expanded, the therapeutic member 7 is placed in contact with the wall of a blood vessel. The carrier 6 ensures the contact force of the therapeutic member 7 does not exceed a maximum force, thus advantageously providing a more consistent contact force that may allow for more consistent lesion formation.

Referring back to FIG. 1C, the energy source or energy generator 8 (e.g., a RF energy generator) may be configured to generate a selected form and magnitude of energy for delivery to the target treatment site via therapeutic member 7. The energy generator 8 can be electrically coupled to the catheter apparatus 1 via a cable 9. A control mechanism (not shown), such as foot pedal, may be connected (e.g., pneumatically connected or electrically connected) to the energy generator 8 to allow the doctor to initiate, terminate and, optionally, adjust various operational characteristics of the energy generator, for example, power delivery. The energy generator 8 can be configured to deliver the treatment energy via an automated control algorithm and/or under the control of the doctor. In addition, the energy generator 8 may include one or more evaluation or feedback algorithms to provide feedback to the doctor before, during, and/or after the intravascular treatment. The generator 8 may be part of a device or monitor that may include processing circuitry, such as a microprocessor. The processing circuitry may be configured to execute stored instructions relating to the control algorithm. The monitor may be configured to communicate with the catheter apparatus 1 to control power to the therapeutic member 7 and/or to obtain signals from the therapeutic member 7 or any associated sensors within or outside the therapeutic assembly 70. The monitor may be configured to provide indications of power levels or sensor data, such as audio, visual or other indications, or may be configured to communicate the information to another device.

In some embodiments, the catheter apparatus 1 may be configured to provide delivery of a monopolar electric field via the therapeutic member 7 (e.g. an electrode). In such embodiments, a skin electrode or surface electrode 40 (as shown in FIG. 1C) may be electrically connected to the energy generator 8 and attached to the exterior of the patient, and may function as a neutral or dispersive electrode during the intravascular treatment.

Figure 3:
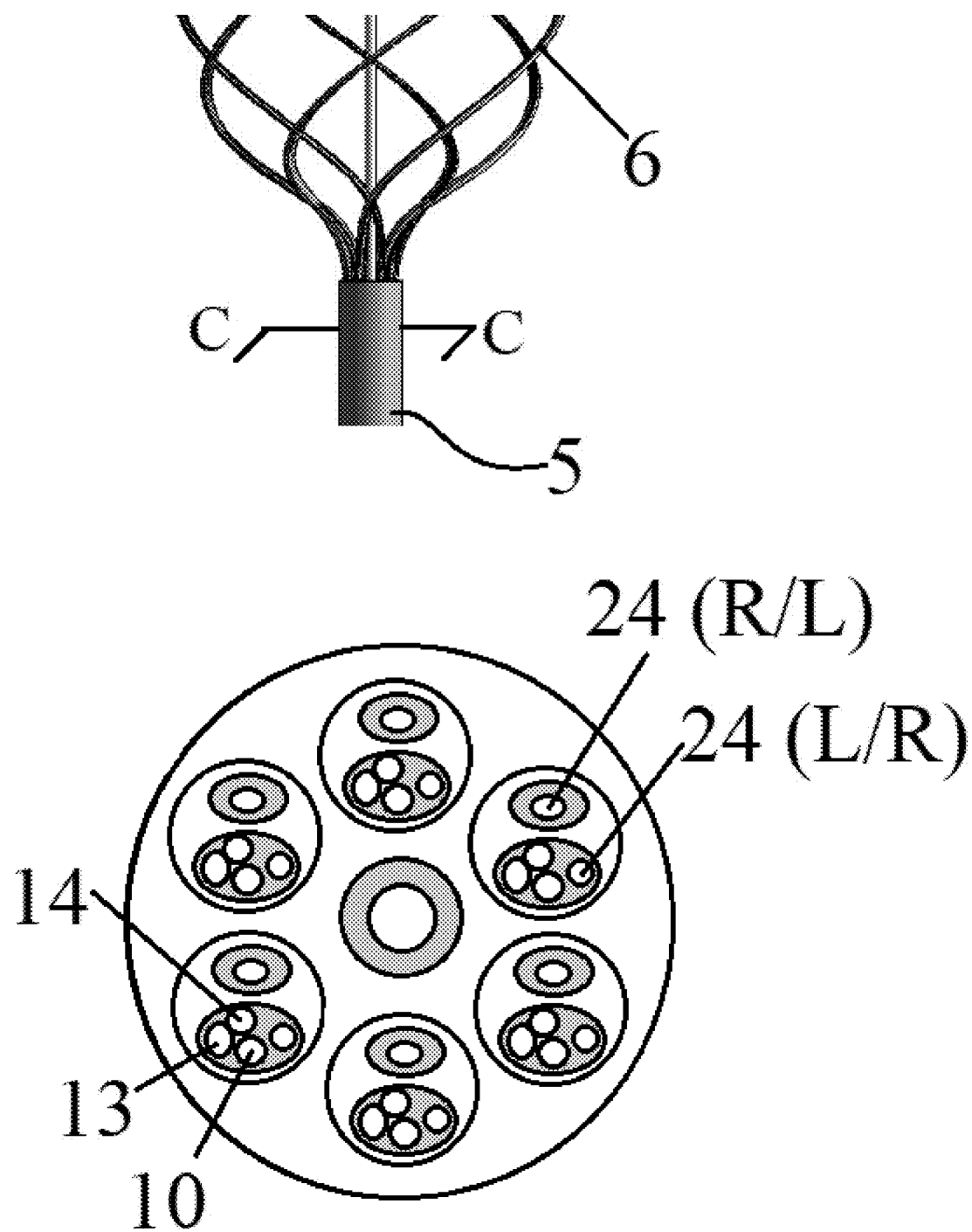
FIG. 3 is a cross-sectional view along C-C of the elongated shaft near the carrier used in an exemplary embodiment.

As shown in FIG. 3, at least one supply wire 10 (such as RF wire 10) passes along the elongated shaft 2 or through a lumen in the elongated shaft 2 to the therapeutic member 7 and transmits the treatment energy from the energy source/generator 8 to the therapeutic member 7.

Figure 4:
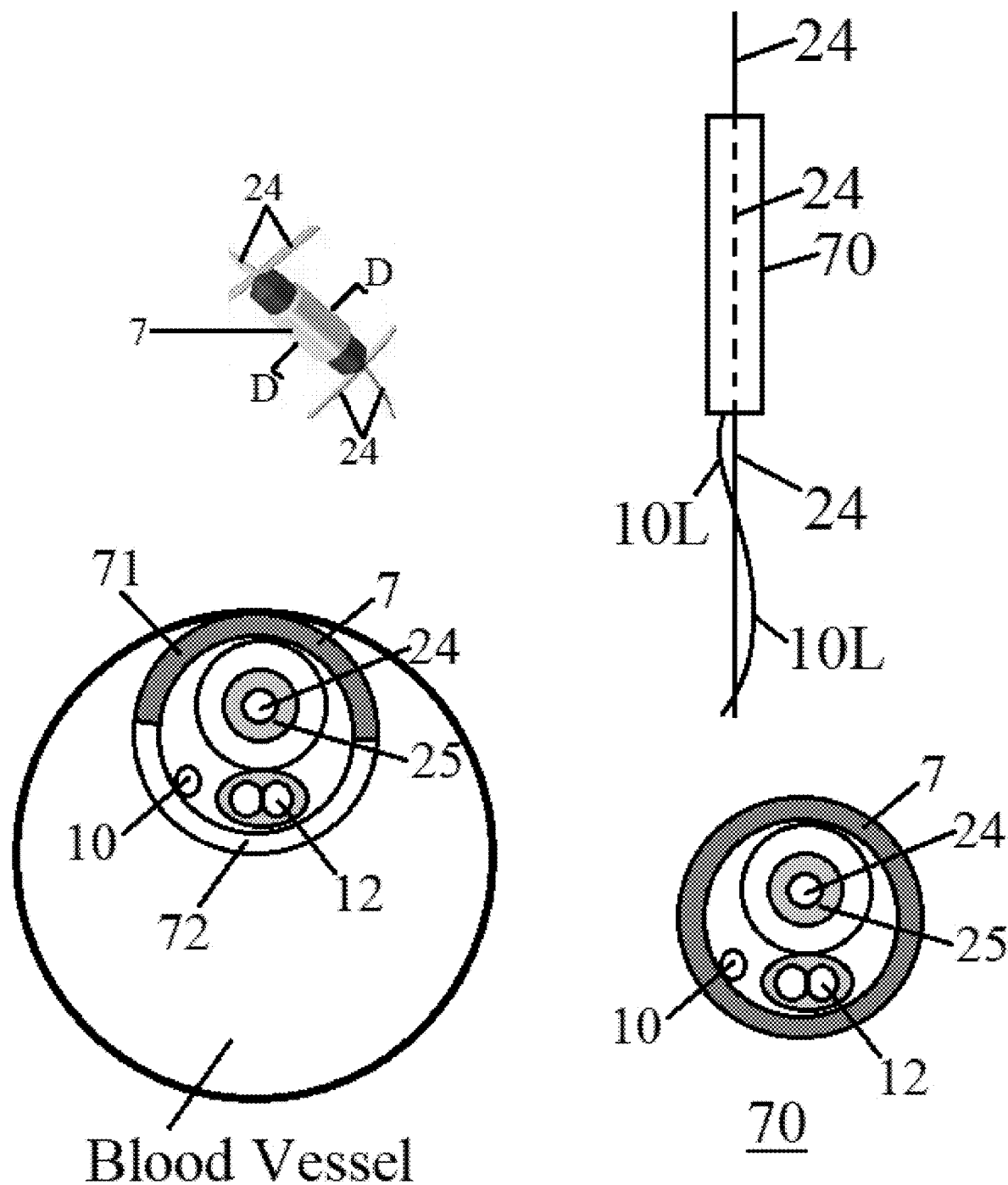
FIG. 4 is a cross-sectional view along D-D of a therapeutic assembly and its position and orientation in a blood vessel.

With reference to FIG. 4, one or more sensors measuring temperature (e.g., thermocouple 12, thermistor, etc.), impedance, pressure, optical, flow, chemical or other parameters, may be located proximate to the therapeutic member 7, e.g. within the therapeutic assembly 70 (i.e. as a part of the therapeutic assembly 70), or not within the therapeutic assembly 70 (i.e. not a part of the therapeutic assembly 70). For example, a total of two supply wires such as thermocouple wires 13 and 14 as shown in FIG. 3 may be included, in which both wires 13 and 14 could transmit the signal from the sensor such as the thermocouple 12, and one wire 13 or 14 could serve dual purpose and also convey RF energy to the therapeutic member 7 (e.g. a RF electrode) without a separate RF wire 10. Alternatively, both wires 13 and 14 could transmit energy to the therapeutic member 7 (e.g. a RF electrode) without a separate RF wire 10.

In various embodiments, energy delivery may be controlled and monitored via data collected with the sensor(s), such as temperature sensors (e.g., thermocouples, thermistors, etc.), impedance sensors, pressure sensors, optical sensors, flow sensors, chemical sensors, etc., which may be incorporated into or on the therapeutic member 7, e.g. within the therapeutic assembly 70, the carrier 6, and/or in/on adjacent areas on the distal portion 5. A sensor may be incorporated into the therapeutic assembly 70 with the therapeutic member 7 in a manner that specifies whether the sensor(s) are in contact with tissue at the treatment site and/or are facing blood flow. It is important to specify temperature sensor placement relative to tissue and blood flow, since a temperature gradient across the electrode from the side facing blood flow to the side in contact with the vessel wall may be up to about 15° C. (for platinum-iridium electrodes). For gold electrodes, this temperature gradient can be around, for example, 1-2° C. In some embodiments, the temperature gradient can vary based, at least in part, on the electrode configuration/material. Significant gradients across the electrode in other sensed data (e.g., flow, pressure, impedance, etc.) can also take place.

The sensor(s) may, for example, be incorporated on or near the side of the therapeutic member 7 that contacts the vessel wall at the treatment site during power and energy delivery or may be incorporated otherwise, such as on the opposing side of the therapeutic member 7 that faces blood flow during energy delivery, and/or may be incorporated within any suitable regions of the therapeutic member 7 (e.g., distal, proximal, quadrants, etc.). In some embodiments, multiple sensors may be provided at multiple positions along the therapeutic member 7, the therapeutic assembly 70, or carrier 6, and/or relative to blood flow. For example, a plurality of circumferentially and/or longitudinally spaced sensors may be provided. In one embodiment, a first sensor may face the vessel wall during treatment, and a second sensor may face the blood flow.

Additionally or alternatively, various microsensors may be used to acquire data corresponding to the therapeutic member 7, the vessel wall and/or the blood flowing across the therapeutic member 7. For example, arrays of micro thermocouples and/or impedance sensors may be implemented to acquire data along the therapeutic member 7 or other parts of the carrier 6. Sensor data may be acquired or monitored prior to, simultaneous with, or after the delivery of energy or in between pulses of energy. The monitored data may be used in a feedback loop to better control therapy, e.g., to determine whether to continue or stop treatment, and it may facilitate controlled delivery of therapy with an increased or reduced power, or a longer or shorter duration.

When catheter apparatus 1 is being used, the distal portion 5 of the elongated shaft 2 as well as the carrier 6 may be moved through an intravascular path by following a path defined by a guide catheter, a guide wire, or a sheath, such as from a percutaneous access site in the femoral, brachial, radial, or auxiliary artery, to a targeted site within the blood vessel. A section of the proximal portion 3 of the shaft 2 is exposed externally of the patient. By manipulating the proximal portion 3 of the shaft 2 from outside the intravascular path (e.g., via the handle assembly 4), the doctor may advance the shaft 2 through the sometimes tortuous intravascular path and remotely manipulate or actuate the distal portion 5 of the shaft 2. Image guidance, e.g., computed tomography (CT), fluoroscopy, intravascular ultrasound (IVUS), optical coherence tomography (OCT), any other suitable guidance modality, or combinations thereof, may be used to aid the doctor's manipulation. In some embodiments, image guidance components (e.g., IVUS, OCT) may even be incorporated into the catheter apparatus 1 itself. After the carrier 6 is adequately positioned in the blood vessel, it can be expanded or otherwise deployed using the handle 4 or other suitable means until the therapeutic member 7 such as RF electrodes are in stable contact with the inner wall of the blood vessel.

Referring back to FIG. 2, the compressed, collapsed or delivery configuration of the carrier 6 facilitates insertion and/or removal of the catheter apparatus 1 and, in certain embodiments, repositioning of the catheter apparatus 1 within the blood vessel. In the collapsed configuration, the carrier 6 is sized and shaped to fit within the blood vessel and has a diameter that is less than a blood vessel lumen diameter. The carrier 6 is expected to provide stable contact of the therapeutic member 7 with the inner wall of a vessel without occluding the blood flow within the vessel. As the carrier 6 is fabricated or woven from wires, blood can flow through the carrier 6 via interstices 15, the structure of which will be described in more details.

Figure 5:
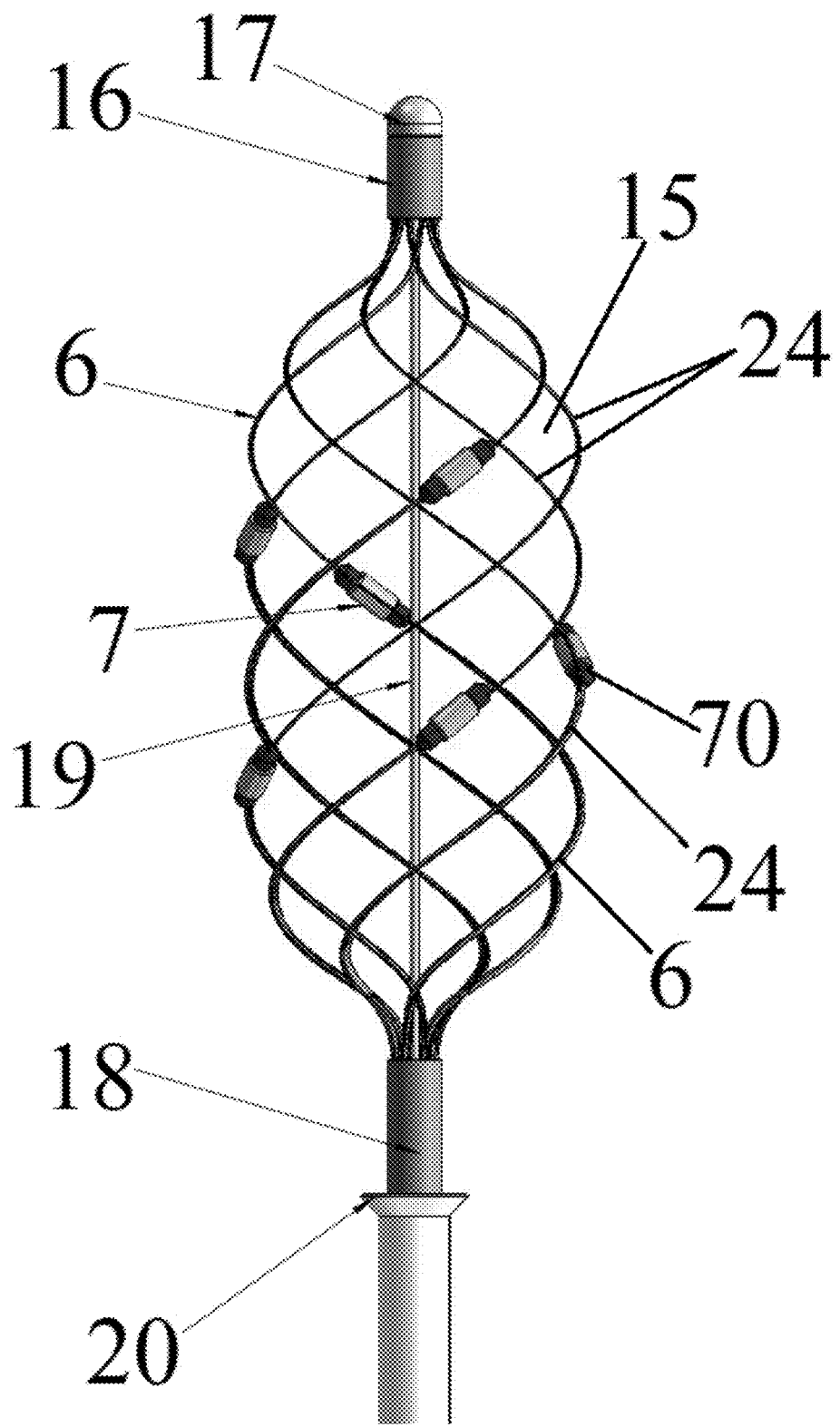
FIG. 5 depicts the specific structure of a carrier used in an exemplary embodiment.

Referring now to FIG. 5, the distal end of the carrier 6 may be coupled to an end piece 16 (e.g., a collar, shaft, or cap) having a rounded distal portion 17 to facilitate atraumatic insertion of the carrier 6 into a blood vessel. Alternatively, a rounded part that is radiopaque (or visible to X-ray imaging such as CT) may replace the rounded distal portion 17 to facilitate atraumatic insertion of the carrier 6 and to track the location of the carrier 6. The proximal end of the carrier 6 may be connected to, or coupled to, the elongated shaft 2 using a multi-lumen coupling 18. Coupling 18, for example, may be an integral end of the elongated shaft 2 (e.g., may not be a separate piece) or may be a separate piece that is associated with the distal region of the elongated shaft 2. The coupling 18 may be formed from the same type of material as the elongated shaft 2, or may be formed from a different material. In one embodiment, the coupling 18 may be formed from a collar, such as a radiopaque band, that surrounds and secures the carrier 6 to an exterior surface of the elongated shaft 2.

The elongated shaft 2, the coupling 18, the carrier 6, and the end piece 16 may include passages sized and shaped to accommodate a control wire or pull/push wire 19 that is fixed to the distal end of the carrier 6 or the end piece 16 and passes through the elongated shaft 2 to the proximal portion 3 of the elongated shaft 2. The control wire 19 facilitates the expansion and/or contraction of the carrier 6 when it is pulled or pushed to shorten or lengthen the carrier 6. For example, pulling (i.e., an increase in tension) the control wire 19 proximally relative to the shaft 2 may trigger expansion of the carrier 6 by drawing end piece 16 closer to coupling 18. Conversely, pushing (i.e., an increase in compression) the control wire 19 distally relative to shaft 2 may lengthen the carrier 6 to a compressed configuration by axially spreading apart end piece 16 and coupling 18. It will be understood that either the shaft 2 or the control wire 19 may be held in fixed position with respect to the patient while the other element is translated to create the relative movements described above. In some embodiments the carrier 6 has elastic or super-elastic shape memory properties such that when force is removed, the carrier 6 elastically returns to a relaxed state or a natural state as shown in FIG. 2. Force may be applied by the control wire 19 to deform the carrier 6 into one state, and when force is removed, the mesh carrier 6 returns to its relaxed state. For example, a relaxed or "natural" state of the carrier 6 may be a half-way expanded configuration as shown in FIG. 2, and the control wire 19 may be pushed to lengthen the carrier 6 and reduce its diameter, placing it in a collapsed or "compressed" configuration as shown in FIG. 2. Alternatively, a relaxed state of the carrier 6 may be a collapsed or compressed configuration and the control wire 19 may be pulled (tension applied) to shorten the carrier 6 and increase its diameter, placing it in an expanded configuration. In some embodiments, the control wire 19 may be a solid or stranded wire or cable made from a metal or polymer. In other embodiments, the control wire 19 may be a hollow tube that can be passed over a guide wire to facilitate insertion through an intravascular path to a targeted site in the blood vessel.

As shown in FIG. 5, the carrier 6 includes structural elements, e.g., wires 24 (or strands, filaments or fibers) arranged to define interstices 15 (or interstitial spaces) therebetween. Because the change in diameter and axial length of the carrier 6 may involve realignment of wires 24 and variations of the geometry of the interstices 15, the makeup of the wires 24 and the geometry of the interstices 15 may at least in part define how much the diameter and length of the carrier 6 change as a result of its configuration changes.

The wires 24 may be formed from biocompatible metals, polymers, or composites. For example, suitable metals can include stainless steel, spring steel, cobalt chromium, gold, platinum, platinum-iridium, stainless steel, or combinations thereof. In one particular embodiment, the carrier 6 may be composed of nitinol with gold plating to enhance radiopacity and/or conductivity. Suitable polymer materials can include, for example, polyethylene terephthalate (PET), polyamide, polyimide, polyethylene block amide copolymer, polypropylene, or polyether ether ketone (PEEK) polymers. In some embodiments, the carrier 6 may be a combination of electrically conductive and nonconductive materials.

In some embodiments, the carrier 6 may be formed at least in part from radiopaque materials that are capable of being imaged fluoroscopically to allow a doctor to determine if the carrier 6 is appropriately placed and/or deployed in the blood vessel. Radiopaque materials may include barium sulfate, bismuth trioxide, bismuth subcarbonate $(BiO)_2CO_3$, powdered tungsten, powdered tantalum, or various formulations of certain metals, including gold and platinum, and these materials may be directly incorporated into the wires 24 or may form a partial or complete coating of the carrier 6.

The carrier 6 may be designed to apply a desired outward radial force to a blood vessel wall when inserted and expanded to contact the inner surface of the wall. The radial force may be selected to avoid injury from stretching or distending the vessel when the carrier 6 is expanded against the wall within the patient. Radial forces that may avoid injuring the blood vessel yet provide adequate stabilization force may be determined by calculating the radial force exerted on a vessel wall by typical blood pressure. For example, a suitable radial force may be less than about 300 mN/mm (e.g. less than 200 mN/mm). Fibers 24 formed from stiffer materials (e.g. metals) may be thinner relative to fibers 24 formed highly flexible polymers to achieve similar flexibilities and radial force profiles. The outward pressure of the carrier 6 may be assessed in vivo by an associated pressure transducer.

The carrier 6 with more open structures (e.g., bigger interstices 15, or lower material per square inch ratios) may have less radial stiffness and strength than more closed structures (smaller interstices 15, or high material density structures). The thickness of fibers 24 also affects outward pressure, radial strength and stiffness. Certain secondary processes, including heat treating and annealing, may harden or soften the fiber material to affect strength and stiffness. In particular, for shape-memory alloys such as nitinol, these secondary processes may be varied to give the same starting material different final properties. For example, the elastic range or softness may be increased to impart improved flexibility. The secondary processing of shape memory alloys influences the transition temperature, i.e., the temperature at which the structure exhibits a desired radial strength and stiffness. This temperature may be set at normal body temperature (e.g. 37° C.).

The carrier 6 may be braided, knit, or woven to form a conformable structure (e.g., a tubular, barrel-shaped, parachute-shaped, or spherical structure) through which fluids may pass. In embodiments, the carrier 6 may include 4-48 fibers. It should be understood that fiber 24 may be formed from a single filament (monofilament) or by a plurality of filaments twisted or otherwise grouped together to form a multifilar fiber. In addition, the carrier 6 may be characterized by its braid pitch, which may be between 1-10 picks (i.e., windings) along its axial length. In preferred embodiments, the carrier 6 may be helically braided with right-handed helix wires and left-handed helix wires) into a generally ovoid, tubular, barrel, or other shaped structure.

In some embodiments, the carrier 6 may be generally symmetrical and coaxial with respect to the elongated shaft 2 or control wire 19. However, it is also contemplated that the carrier 6 may conform to any irregularities in the blood vessel (e.g. a shape of fortune cookie), which may be assessed by imaging or other techniques. For example, particular sizes and types of carrier 6 may be used in conjunction with a patient's particular anatomic features.

For some patients, it may be desirable to configure the therapeutic member(s) 7 in such a manner that they can create either a single lesion or a pattern of multiple focal lesions that are spaced apart circumferentially and/or axially along the longitudinal axis of the blood vessel. A single focal lesion with desired longitudinal and/or circumferential dimensions, one or more full circumferential lesions, multiple circumferentially spaced focal lesions at a common longitudinal position, spiral-shaped lesions, interrupted spiral lesions, generally linear lesions, and/or multiple longitudinally spaced focal lesions along a line parallel to the axis of the blood vessel alternatively or additionally may be created. In other embodiments, the therapeutic member(s) 7 may be used to create lesions having a variety of other geometric shapes or patterns.

Depending on the size, shape, and number of the therapeutic member(s) 7, the lesions created may be circumferentially spaced around the blood vessel, either in a single transverse plane or the lesions may also be spaced apart longitudinally. In some embodiments, it is desirable for each lesion to cover at least 10% of the vessel circumference. It is also desirable that each lesion be sufficiently deep to penetrate into and beyond the adventitia. However, lesions that are too deep run the risk of interfering with non-target tissue and tissue structures, and therefore a controlled depth of treatment is also desirable.

In general embodiments, the therapeutic member(s) 7 may be circumferentially repositioned relative to the blood vessel during treatment. This angular repositioning may be achieved, for example, by compressing the carrier 6 and rotating the elongated shaft 2 via handle assembly 4. In addition to the angular or circumferential repositioning of the therapeutic member(s) 7, it/they optionally may also be repositioned along the lengthwise or longitudinal dimension of the blood vessel. This longitudinal repositioning may be achieved, for example, by translating the elongated shaft 2 via the handle assembly 4, and may occur before, after, or concurrently with angular repositioning of the therapeutic member(s) 7. Repositioning the therapeutic member(s) 7 in both the longitudinal and angular dimensions places it/them in contact with the interior wall of the blood vessel at a second treatment site. RF Energy may then be delivered via the therapeutic member 7 to form a second focal lesion at this second treatment site. For embodiments in which multiple therapeutic members 7 are associated with the carrier 6, the initial treatment may result in two or more lesions, and repositioning may allow additional lesions to be created. One or more additional focal lesions optionally may be formed via additional repositioning of the carrier. In preferred embodiments, the carrier 6 carries a sufficient number of therapeutic member 7 (e.g. RF electrodes), and it does not have to be selectively repositioned within the blood vessel to provide a number of locations for e.g. RF energy delivery.

In certain embodiments, the lesions created via repositioning of the carrier 6 are circumferentially and longitudinally offset from the initial lesion(s) about the angular and lengthwise dimensions of the blood vessel, respectively. The composite lesion pattern created along the blood vessel by the initial energy application and all subsequent energy applications after any repositioning of the therapeutic member(s) 7 may effectively result in a discontinuous lesion (i.e., it is formed from multiple, longitudinally and angularly spaced treatment sites).

Sometimes, it may be desirable to configure the therapeutic member(s) 7 in such a manner to create a composite lesion pattern, as viewed from a proximal or distal end of the vessel, to extend at least approximately all the way around the circumference of the blood vessel under treatment. In other words, each formed lesion covers an arc of the circumference; and each of the lesions, as viewed from an end of the vessel, abut or overlap adjacent lesions to create a virtually circumferential lesion. The formed lesions defining an actual circumferential lesion lie in a single plane perpendicular to a longitudinal axis of the blood vessel. A virtually circumferential lesion is defined by multiple lesions that may not all lie in a single perpendicular plane, although more than one lesion of the pattern can be so formed. At least one of the formed lesions comprising the virtually circumferential lesion is axially spaced apart from other lesions.

For example, a cylindrical carrier 6 having therapeutic members 7 affixed to wires 24 in a helical pattern such that therapeutic members 7 are circumferentially and axially offset from one another. The circumferential offset arcs, or corresponding radial angles, may be selected so that when energy is applied to the blood vessel via therapeutic members 7, a roughly helical lesion pattern is formed therein. Depending on the number and positioning of the therapeutic members 7 selectively mounted on wires 24, a helical lesion pattern with any desired number of turns (e.g. 1, 2, 3 or more) may be formed using only a single RF energy application. In other embodiments, the therapeutic members 7 may have a variety of different arrangements relative to each other (e.g., linear, interrupted helix, continuous helix).

In a non-limiting example, the therapeutic members 7 are configured in such a manner to create a virtually circumferential lesion comprising six lesions created in a single helical pattern along the blood vessel; and each lesion spans an arc extending along at least one sixth (or 60 degree) of the vessel circumference such that the resulting pattern of lesions completely encompasses the vessel circumference, when viewed from an end of the vessel. In other examples, however, a virtually circumferential lesion can comprise a different number of lesions.

The axial distances between axially adjacent therapeutic members 7 may be selected so that the edges of the lesions formed by each individual therapeutic member 7 on the blood vessel wall 55 are either overlapping or non-overlapping. The axial distance may be about 2 mm to about 1 cm. In a particular embodiment, the axial distance may be in the range of about 2 mm to about 5 mm. In another representative embodiment, the axially adjacent therapeutic members 7 may be spaced apart about 10-50 mm.

Therapeutic member(s) 7 may be coupled to leads 10L, which may be e.g. a part of RF wire 10, or electrically connected to RF wire 10. The leads 10L may be separate from the carrier 6, or may be loosely or tightly coupled to, adhered to, wrapped around, or integrated into to the carrier 6 (e.g. around/on/with/to a wire 24) to prevent twisting or kinking of the leads. In particular embodiments, to facilitate the stable contact of the therapeutic member(s) 7 to the blood vessel, the therapeutic assembly 70 may be coupled to carrier 6 by weaving lead(s) into the wires 24 of the mesh or threading leads through interstices in the mesh of carrier 6. At least a part of the therapeutic member(s) 7 is positioned on an exterior surface of carrier 6. The positioning of the therapeutic member(s) 7 on the exterior surface may be associated with a desired lesion pattern. Alternatively, as shown in FIGS. 2 and 5, the therapeutic assembly 70 may be directly coupled to the wire 24. The therapeutic assembly 70 is coupled to wire 24, for example via adhesion or threading a wire 24 through an internal bore 25, as shown in FIG. 4.

The therapeutic member 7 may be in the form of an electrically conductive tube. As shown in FIG. 4, the tube electrode 7 may be wound about (or wrapped around) wire 24. In other words, a wire 24 inserts into and passes through the tube electrode 7. For example, six tube electrodes 7 may form a loose-pitch or tight-pitch "dotted", interrupted or discontinuous helix. Regions of the tube electrode 7 that do not contact the blood vessel wall may contribute to cooling of the electrode. Alternatively, as shown in FIG. 4, only portion 71 of the tube electrode 7 may be electrically conductive with the blood vessel wall tissue. That is, the tube electrode 7 can include insulated portion 72 and uninsulated portion 71 in which the insulation is removed. For example, the flow of blood over the portion 72 (which is not contacting vessel wall) provides conductive and convective cooling of a RF electrode 7, thereby carrying excess thermal energy away from the interface between the vessel wall and electrode 7. Electrode cooling can be alternatively or additionally achieved by injecting or infusing cooling fluids such as saline (e.g., room temperature saline or chilled saline) over the electrode and into the blood stream. It may also be desirable to provide enhanced cooling by inducing additional native blood flow across the carrier 6. For example, techniques may be implemented by the doctor to increase perfusion through the target blood vessel or to the carrier 6. These techniques include positioning partial occlusion elements (e.g., balloons) within upstream vascular bodies such as the aorta, or within a portion of the target blood vessel to improve flow across the carrier 6. Because cooling of the electrode 7 is mediated by blood flow, improved cooling may be achieved by redirecting a faster blood flow into the target blood vessel or into the carrier 6 so that the blood flowing around the electrode 7 is relatively faster. Sometimes, without a proper cooling, resistive heating of the tissue may be too aggressive and not enough excess thermal energy is being carried away, resulting in excessive heat generation and increased potential for stenotic injury, thrombus formation and undesirable lesion size.

The therapeutic member 7 may be sized and configured to contact an internal wall of the blood vessel during the treatment. For example, the therapeutic member 7 may take the form of an electrode sized and configured to apply an electrical field of RF energy from the energy generator 8 to a vessel wall. As described above, the electrode 7 may be operated in a monopolar or unipolar mode. In this arrangement, a return path for the applied RF electric field is established, e.g., by an external dispersive electrode or skin electrode 40 (as shown in FIG. 1), also called an indifferent electrode or neutral electrode. The monopolar application of RF electric field energy serves to ohmically or resistively heat tissue in the vicinity of the electrode 7. The application of the RF electrical field thermally injures tissue. For example, a treatment objective may be to thermally induce neuromodulation (e.g., necrosis, thermal alteration or ablation) in the targeted neural fibers. The thermal injury forms a lesion in the vessel wall. Alternatively, a RF electrical field may be delivered with an oscillating intensity that does not thermally injure the tissue whereby neuromodulation in the targeted nerves is accomplished by electrical modification of the nerve signals.

The term "active surface area" of the electrode 7 is defined as the energy transmitting area of the electrode 7 that may be placed in intimate contact against tissue. Too much contact between the electrode and the vessel wall may create unduly high temperatures at or around the interface between the tissue and the electrode, thereby creating excessive heat generation at this interface. This excessive heat may create a lesion that is circumferentially too large. In some instances, too much contact can also lead to small, shallow lesions. Too little contact between the electrode 7 and the vessel wall may result in superficial heating of the vessel wall, thereby creating a lesion that is too small (e.g., <10%/a of vessel circumference) and/or too shallow.

Figure 6:
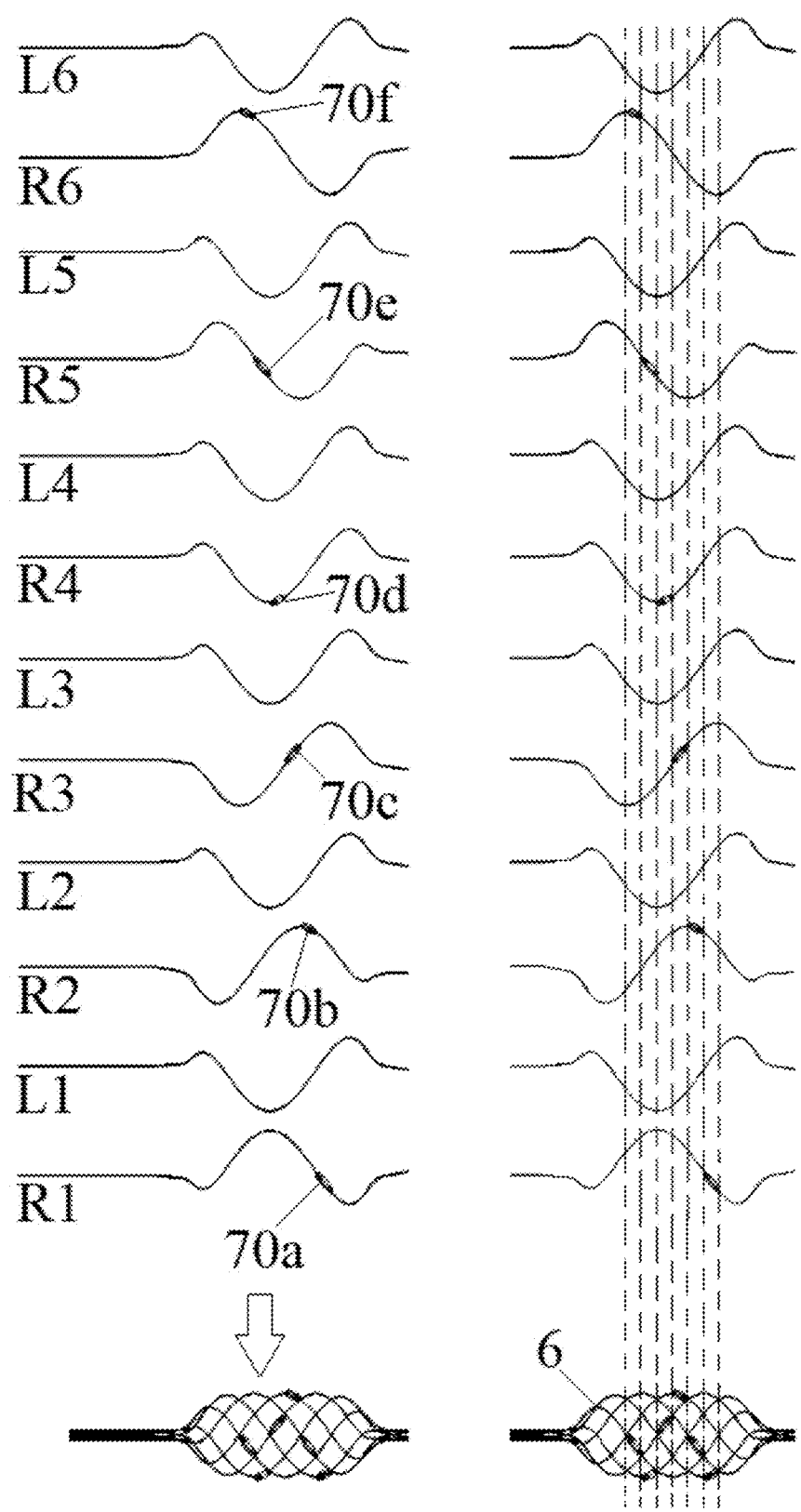
FIG. 6 schematically shows a carrier including right-handed wire helixes and left-handed wire helixes used in an exemplary embodiment.

As described above, the carrier 6 may be helically braided with right-handed helix wires and left-handed helix wires) into a generally ovoid, tubular, barrel, or other shaped structure. In preferred embodiments as shown in FIG. 6, the carrier 6 comprises m (m≥2) right-handed wire helixes such as 6 R-helixes R1~R6 and n (n≥2) left-handed wire helixes such as 6 L-helixes L1~L6. With the line of sight along the helix's axis, if a clockwise screwing motion moves the helix away from the observer, then it is called a right-handed helix; if towards the observer, then it is a left-handed helix. Handedness or chirality (symbolized as R- and L-) is a property of the helix, not of the perspective. A right-handed helix cannot be turned to look like a left-handed one unless it is viewed in a mirror, and vice versa. In some embodiments, the carrier 6 comprises m right-handed wire helixes and n left-handed wire helixes that are plainly or bi-axially woven into a tubular structure, 2≤m≤30 and 2≤n≤30, such as 3≤m≤20 and 3≤n≤20; 4≤m≤15 and 4≤n≤15; 5≤m≤10 and 5≤n≤10. For example, helixes R1~R6 and L1~L6 are plainly or bi-axially woven into carrier 6 with a tubular structure, as shown in FIG. 6.

Figure 7:
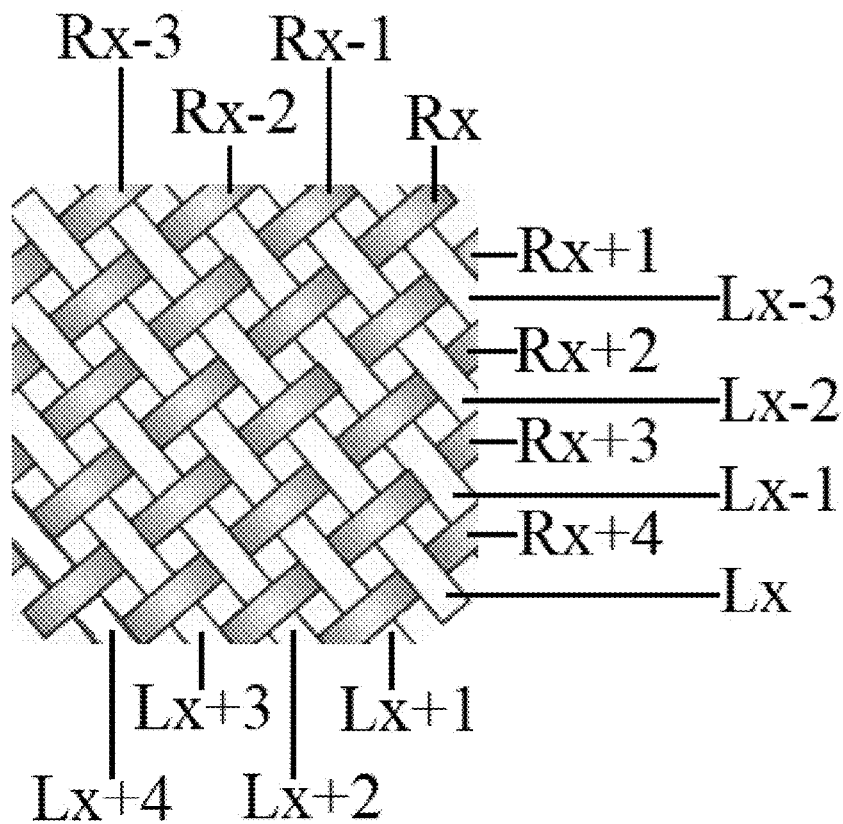
FIG. 7 shows how wires are plainly or bi-axially woven in accordance with an exemplary embodiment of the present invention.
Figure 7:
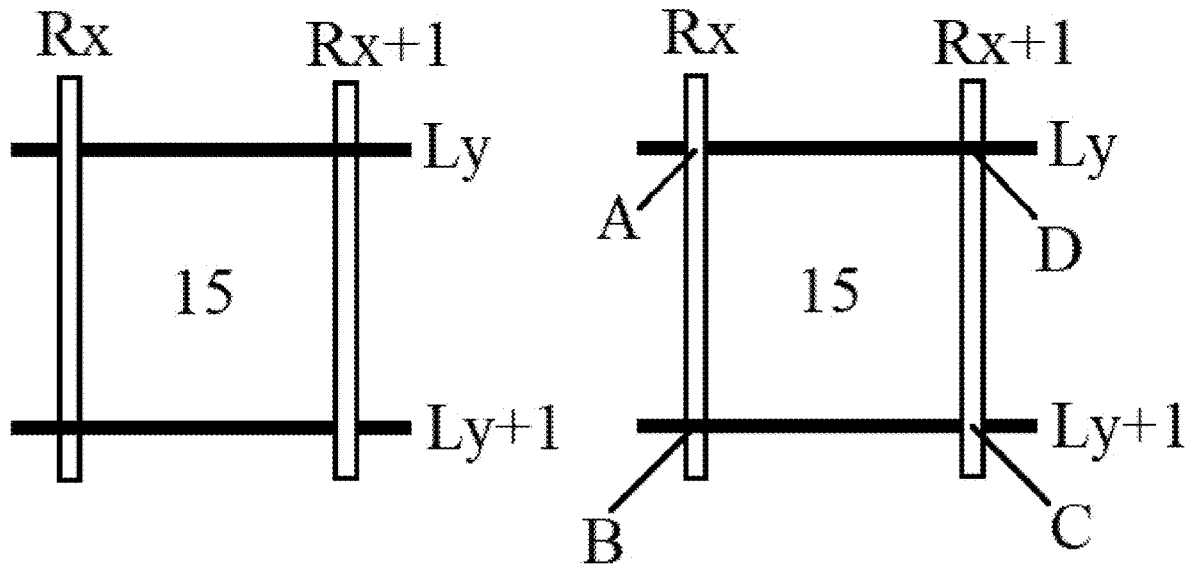

The term "plainly or bi-axially" is defined and explained with reference to FIG. 7. Any right-handed helix wire R (e.g. Rx) is woven into (or between) at least two immediately adjacent left-handed helix wires Ls (e.g. Ly and Ly+1), in such a manner that one L wire (e.g. Ly) is beneath wire R (e.g. Rx), while another L wire which is immediately next to Ly (e.g. Ly+1) is above Rx. In other words, Ly and Ly+1 are located on the opposite sides of wire Rx. A right-handed helix wire Rx+1, that is immediately next to (or adjacent to) wire Rx, is also woven into (or between) two wires Ly and Ly+1, but in an opposite manner to produce an opposite configuration that wire Ly is above wire Rx+1, while wire Ly+1 is beneath Rx+1. By the same token, any left-handed helix wire Ly is woven into at least two immediately adjacent right-handed helix wires Rx and Rx+1, in such a manner that wire Rx is above wire Ly, while wire Rx+1 is below Ly. In other words, Rx and Rx+1 are located on the opposite sides of wire Ly. A left-handed helix wire Ly+1, that is immediately next to (or adjacent to) wire Ly, is woven into two wires Rx and Rx+1, in an opposite manner to produce an opposite configuration that wire Rx is beneath wire Ly+1, while wire Rx+1 is above Ly+1.

In such a pattern, the four wires (Rx, Rx+1, Ly, and Ly+1) will have four intersectional points (or cross-over points) A, B, C and D that are not fixed, and are movable relative to their two corresponding crossed-over wires. For example, point A is moveable relative to wire Rx and/or Ly as wire Rx slides over Ly and/or Ly slides over Rx. Points B, C and D are also moveable for similar reasons and in similar fashions. As a result, the carrier 6 comprises at least one interstice 15 that is defined by four wire helix segments AB, BC, CD and DA selected from two immediately adjacent right-handed wire helixes (Rx and Rx+1) and two immediately adjacent left-handed wire helixes (Ly and Ly+1) that are plainly or bi-axially woven into each other.

Figure 8:
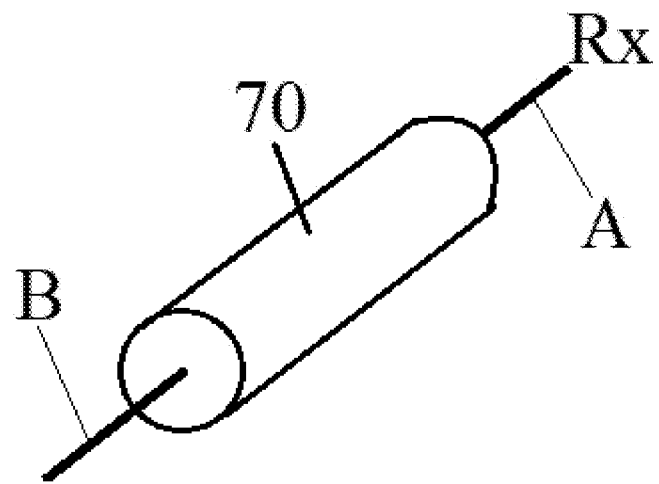
FIG. 8 shows a therapeutic assembly wrapping around a wire helix segment in accordance with an exemplary embodiment.
Figure 8:
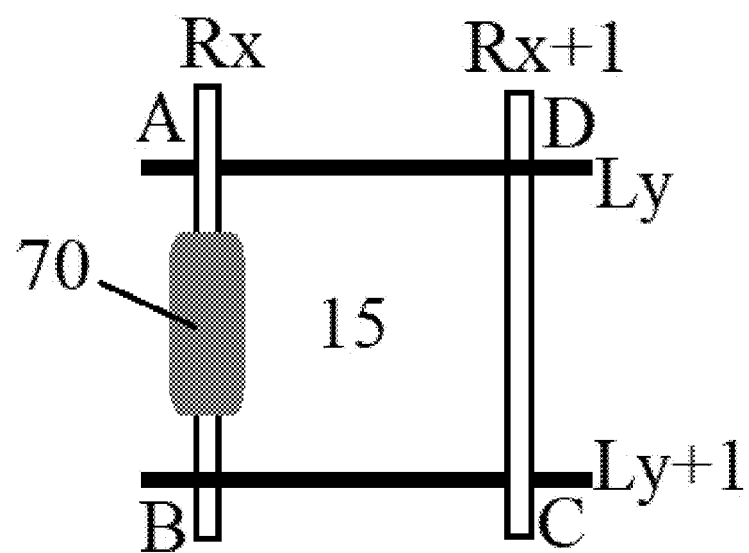

As shown in FIG. 8, at least one therapeutic assembly 70 is configured to wrap around at least one of said four wire helix segments AB, BC, CD and DA (e.g. segment AB) to stabilize said at least one interstice 15. The lengths of helix segments AB, BC, CD and DA vary when the carrier 6's shape is being changed. In some embodiments, only one therapeutic assembly 70 wraps around only one of said four wire helix segments AB, BC, CD and DA (e.g. only segment AB) to stabilize the interstice 15, and does not wrap around any one of the other three helix segments (e.g. segments BC, CD and DA). In a preferred embodiment, therapeutic assembly 70 has a rotational axis (e.g. when it has cylinder shape), and wire helix segment AB penetrates through therapeutic assembly 70 approximately along the rotational axis. By "approximately", it means that the distance between the wire helix segment AB and the rotational axis is always less than 50% of the distance between an edge (or a side surface) of therapeutic assembly 70 and the rotational axis, along any plane perpendicular to the rotational axis. In particularly preferred embodiments, m=n=6, and the carrier 6 carries six therapeutic assemblies 70a-70f as shown in FIG. 6, each of which includes an electrode 7 as the therapeutic member 7, providing six electrodes in total. The six electrodes may be configured to create interrupted spiral but full circumferential lesions on internal wall of a target blood vessel.

Figure 9A:
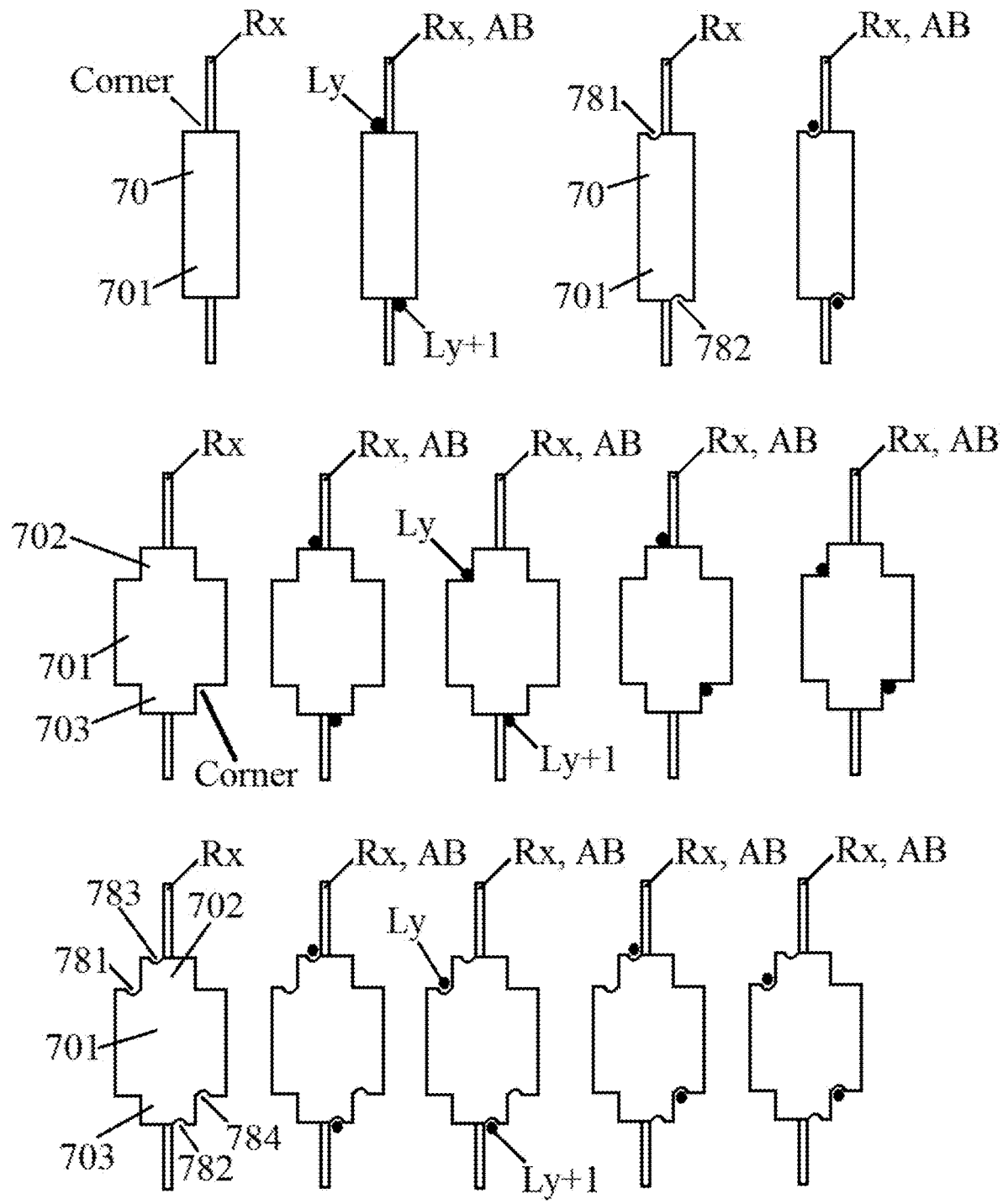
FIG. 9A shows various structures of the therapeutic assembly used in an exemplary embodiment.

As shown in FIG. 9A, the therapeutic assembly 70 may include a main body 701 such as a single cylinder-shaped body 701, without any terminal bodies. Alternatively, assembly 70 may further include two terminal bodies 702 and 703, both of which may be cylinder-shaped, and the main body 701 may be positioned between the two terminal bodies 702 and 703. In other embodiments, terminal bodies 702 and 703 may have a cone shape, tapering down from the main body 701. The cross-sectional area of the main body 701 along a plane perpendicular to the elongation direction of the wire segment AB being wrapped around is larger than cross-sectional areas of both terminal bodies 702 and 703 along a plane perpendicular to the elongation direction of the wire segment AB being wrapped around, which are larger than a cross-sectional area of the wire segment AB itself along a plane perpendicular to the elongation direction of the wire segment AB. The dimension and shape of terminal body 702 may be the same as, or different from, those of terminal body 703.

As shown in FIG. 9A, all the corner areas formed between the main body 701 (when there is no terminal body) and wire Rx, between the main body 701 and terminal body 702 (if present), between the main body 701 and terminal body 703 (if present), between terminal body 702 (if present) and wire Rx, and between terminal body 703 (if present) and wire Rx may be used to accommodate wires Ly and Ly+1, as long as the plainly or bi-axially woven pattern of R- and L-wires is maintained.

At least one of (preferably all) the two terminal bodies 702/703 if any and the main body 710 may include one or more grooves for snugly accommodating or guiding one or more wire helixes that slide(s) over the wire segment around which the therapeutic assembly wraps. For example, body 701/702/703 can be grooved with grooves 781, 782, 783 and 784 near the corner areas for snugly accommodating sliding wires Ly and Ly+1 in a more stable manner, as shown in FIG. 9A. Wires Ly and Ly+1 can slide over wire Rx using the grooves as guides.

Figure 9B:
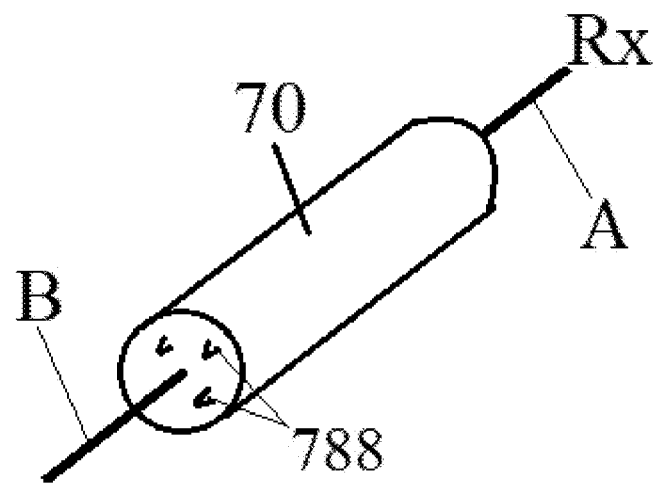
FIG. 9B shows other structures of the therapeutic assembly used in an exemplary embodiment.
Figure 9B:
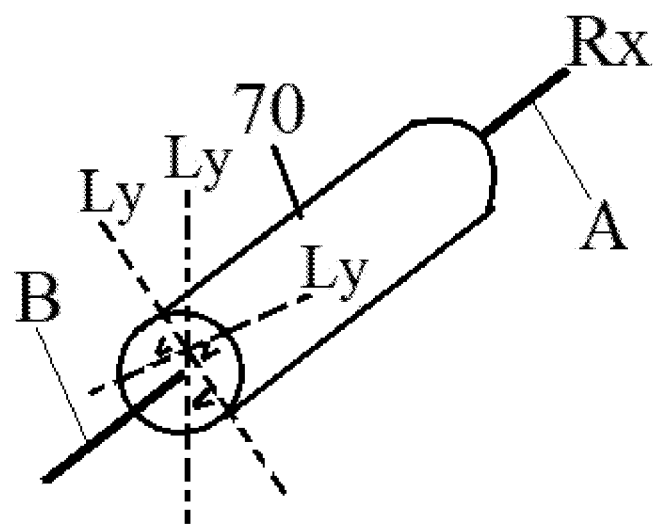

As shown in FIG. 9B, at least one of (preferably all) the two terminal bodies 702/703 if any and the main body 710 may include one, two or more protrusions 788. The gap(s) between segment AB and protrusion(s) 788, and the gap(s) between said protrusion(s) 788 themselves, configured for accommodating or guiding one or more wire helixes Ly or Ly+1 that slide(s) along different directions (represented as the dotted lines Ly) over the wire segment AB around which the therapeutic assembly 70 wraps. When there are three or more protrusions 788, it is preferred that no three protrusions 788 are located along a straight line. As such, we will have as many "Ly guiding directions" as possible.

Figure 10:
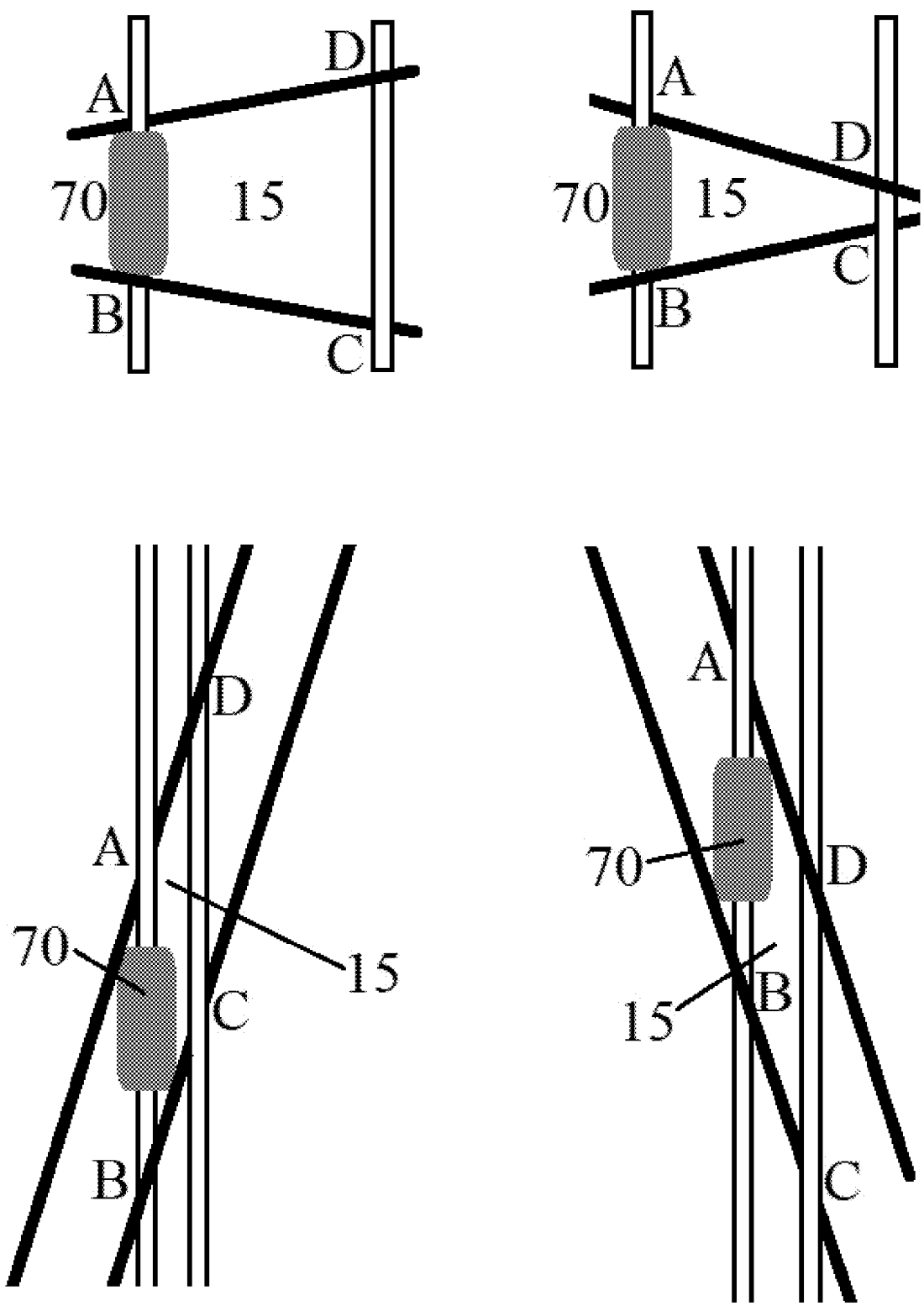
FIG. 10 shows various geometries of the interstice stabilized by a therapeutic assembly in accordance with an exemplary embodiment.

As a result, length of the wire segment AB being wrapped around may now be controlled, depending on where wires Ly and Ly+1 sit, to be equal to, or longer than, the main body 701's length along the elongation direction of the wire segment AB, with or without terminal bodies. It may also be controlled to be equal to, or longer than, the main body 701's length combined with the length of only one of the two terminal bodies (702 or 703) along the elongation direction of the wire segment AB. Alternatively, the length of the wire segment AB being wrapped around may be controlled to be equal to, or longer than, the main body 701's length combined with total length of both two terminal bodies (702 and 703) along the elongation direction of the wire segment AB. As such, various minimal lengths of the wire segment AB may be maintained to be greater than a certain positive value when the carrier 6 is being expanded, compressed, or moved along a curved blood vessel, as shown in FIG. 10. With such minimal lengths of the wire segment AB, wires Ly and Ly+1 are prevented from entangling with each other, and the regular shape of the carrier 6 may be quickly recovered after the carrier is seriously bent or distorted.

Figure 11:
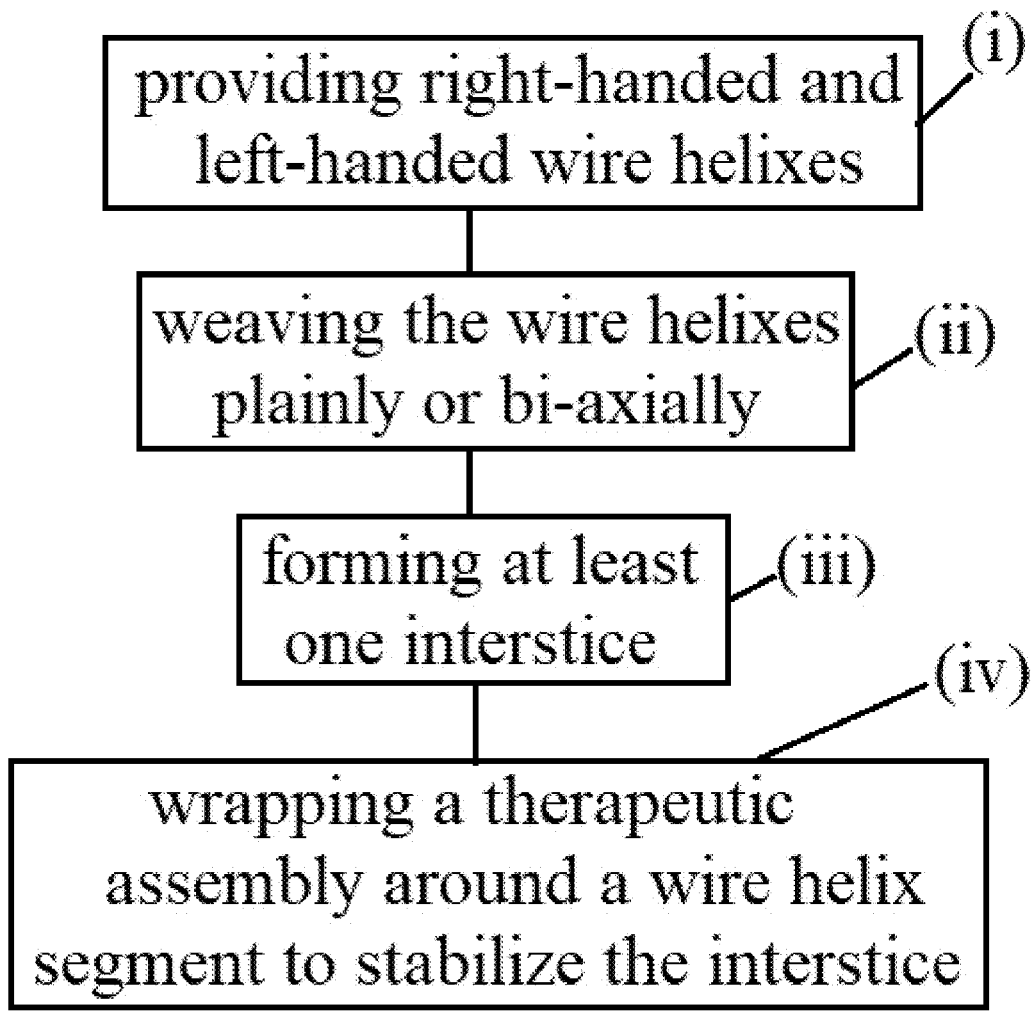
FIG. 11 is a flow chart of a general method of manufacturing a catheter apparatus used in an exemplary embodiment.

The present invention further provides a method of manufacturing the catheter apparatus as described above. As shown in FIG. 11, the method may include: (i) providing m right-handed wire helixes and n left-handed wire helixes, m≥2, and n≥2; (ii) weaving the wire helixes plainly or bi-axially into a tubular structure as the carrier; (iii) forming at least one interstice that is defined by four wire helix segments from two immediately adjacent right-handed wire helixes and two immediately adjacent left-handed wire helixes that are plainly or bi-axially woven into each other, and (iv) wrapping at least one therapeutic assembly around at least one of said four wire helix segments to stabilize the interstice.

Figure 12:
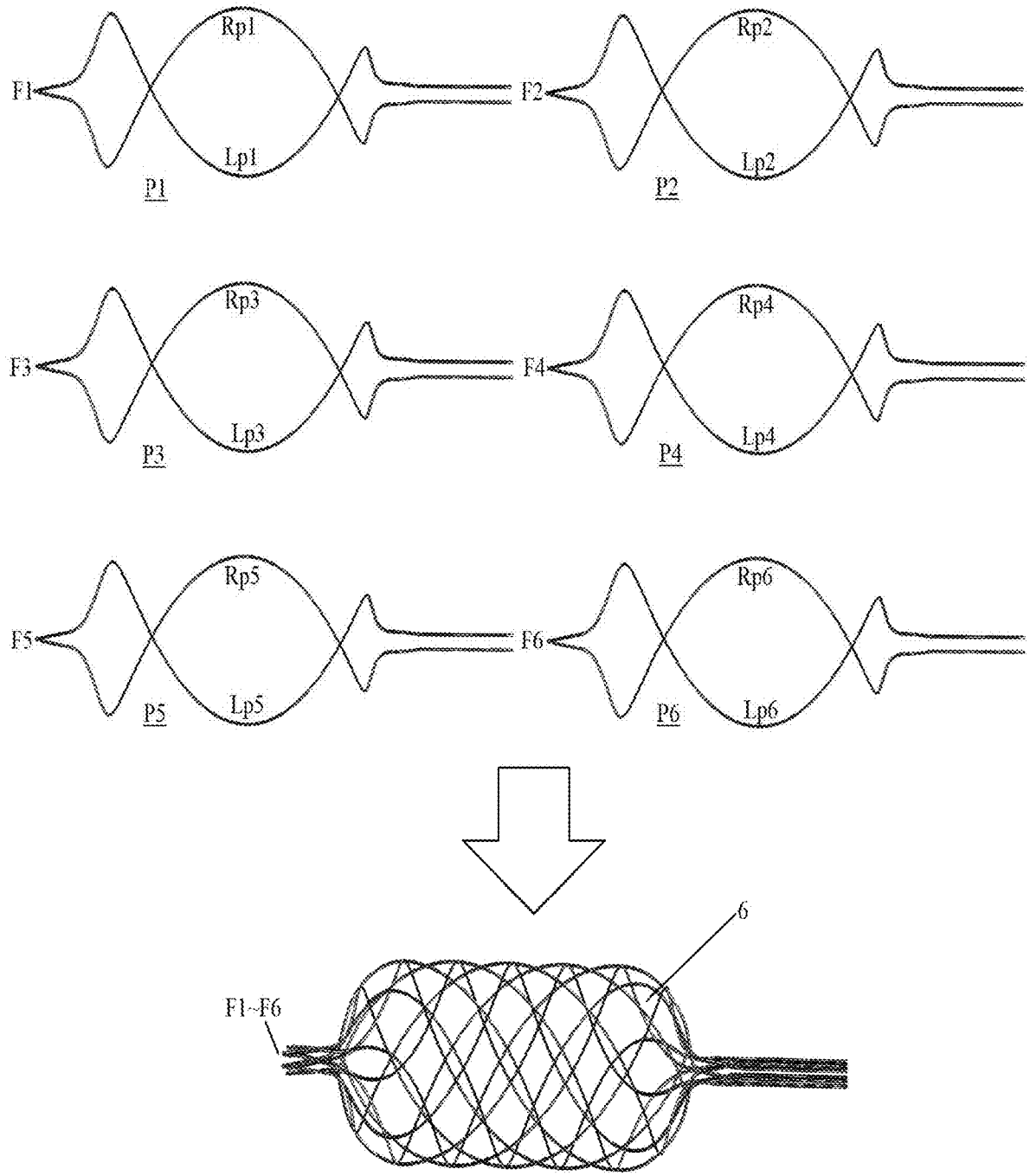
FIG. 12 demonstrates a method of manufacturing a catheter apparatus used in an exemplary embodiment.

In particularly preferred embodiments as shown in FIG. 12, at least one of the m right-handed wire helixes (e.g. one of the 6 R-helixes R1~R6, as shown in FIG. 6) and at least one of the n left-handed wire helixes (e.g. one of the 6 L-helixes L1~L6, as shown in FIG. 6) are made from one single wire, e.g. one of RL-Paired wires P1~P6. The single wire (e.g. P1) includes a first portion of right-handed wire helix Rp, e.g. one of Rp1~Rp6 that are equivalent to R1~R6;

and a second portion of left-handed wire helix Lp, e.g. one of Lp1~Lp6 that are equivalent to L1~L6, by folding or bending a point (F1~F6) of the single wire (P1~P6) between the first portion and the second portion with an angle of approximately 160~180 degree.

As such, step (i) may include the steps of (ia) providing one single wire having a first portion of right-handed wire helix and a second portion of left-handed wire helix; and (ib) folding or bending the single wire at a point between the first portion and the second portion to provide a right-handed wire helix and a left-handed wire helix.

Figure 13:
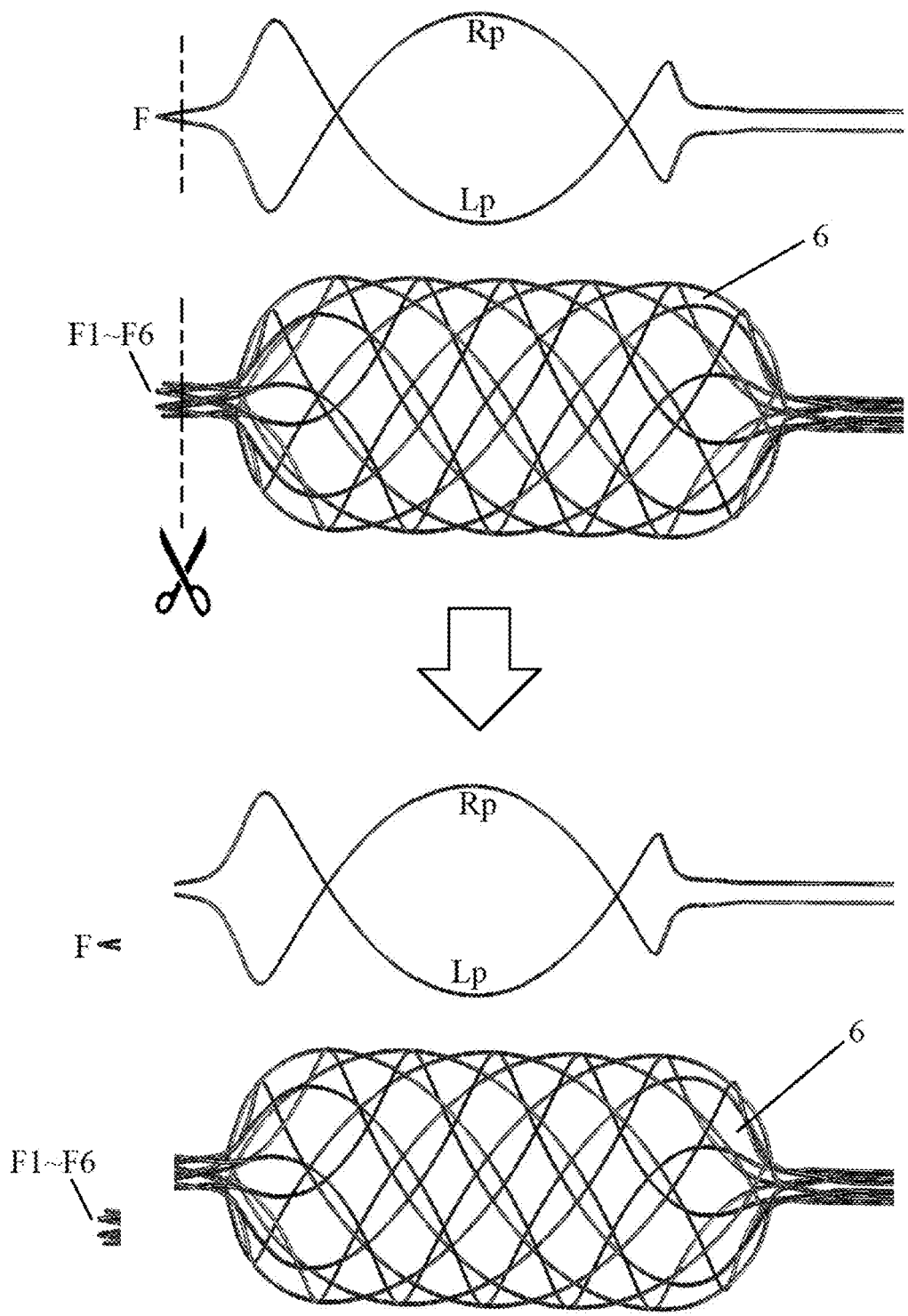
FIG. 13 demonstrates another method of manufacturing a catheter apparatus used in an exemplary embodiment.

In other particularly preferred embodiments as shown in FIG. 13, the method further includes a step of cutting the bent single wire at or near the bending point (F1~F6) to make a separate right-handed wire helix and a separate left-handed wire helix.

Figure 14:
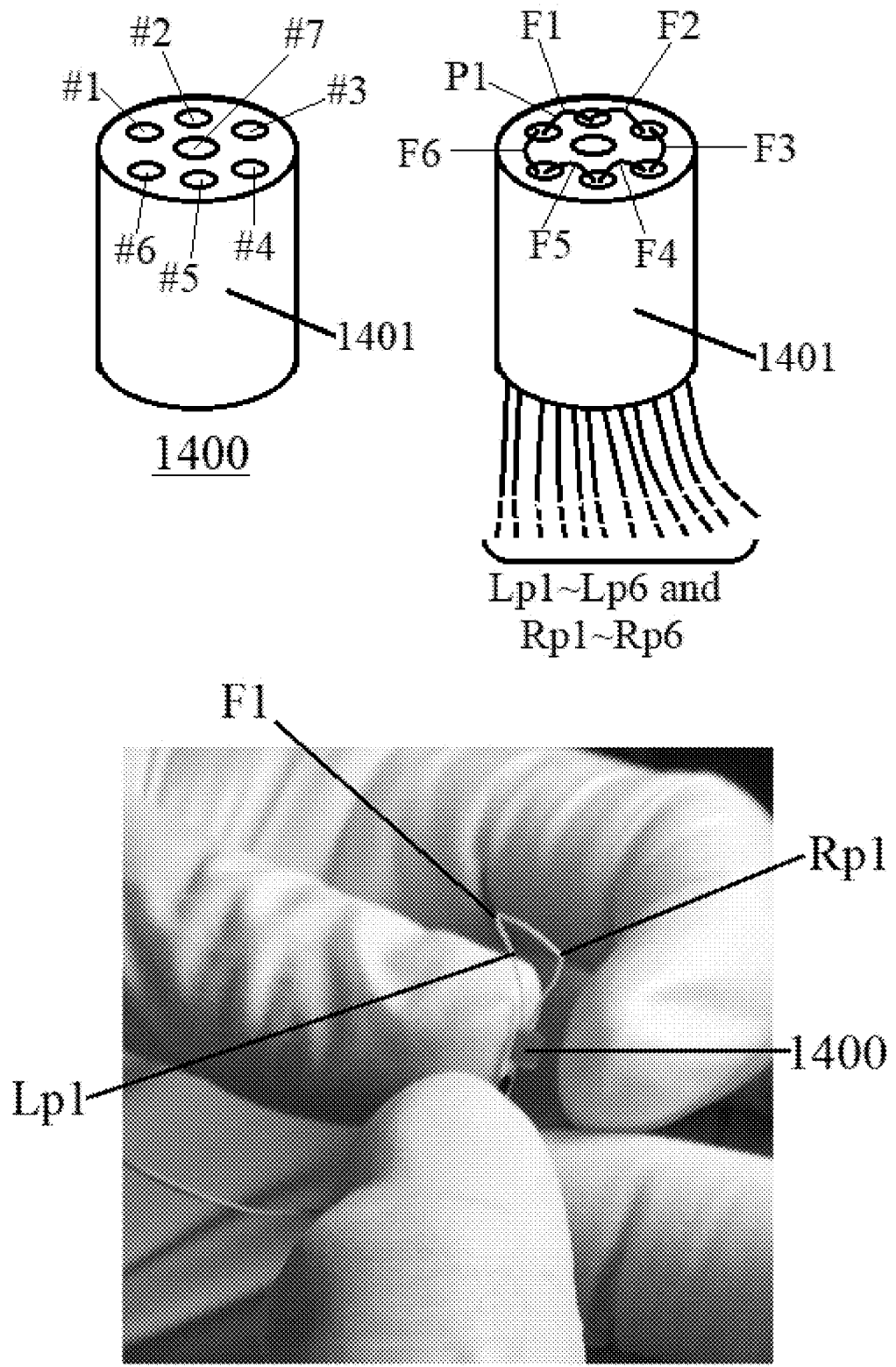
FIG. 14 illustrates the using of a multi-lumen bundler in organizing wires for weaving a carrier used in an exemplary embodiment.

In another embodiment, RL-Paired wires P1, P2, P3, P4, P5 and P6 are bundled together at their ends of the bending points using a multi-lumen bundler. Referring to FIG. 14, the multi-lumen bundler 1400 has a cylinder body 1401. A number of lumens #1~#6 pass axially through the cylinder body 1401 along the longitudinal axis of the cylinder body 1401, and may be arranged in a circular configuration. For a single RL-Paired wire, the first portion of right-handed wire helix Rp may be inserted into a lumen and pass through the lumen, and the second portion of left-handed wire helix Lp may be inserted into another lumen and pass through the lumen. The first portion of right-handed wire helix and the second portion of left-handed wire helix from a same wire may be inserted into and pass through two different lumens. The folding point or bending point of the RL-Paired wire is placed between the two mouths of the two lumens. In exemplary embodiment as shown in FIG. 14, for a single RL-Paired wire P1, the first portion of right-handed wire helix Rp1 may be inserted into lumen #1 and may pass through the lumen #1, and the second portion of left-handed wire helix Lp1 may be inserted into lumen #2 and pass through the lumen #2. The folding point or bending point F1 of the RL-Paired wire P1 is placed between the two mouths of two lumens #1 and #2, preferably F1 is located at the middle point between the two mouths of the two lumens #1 and #2. For RL-Paired wire P2, the first portion of right-handed wire helix Rp2 may be inserted into lumen #2 and may pass through the lumen #2, and the second portion of left-handed wire helix Lp2 may be inserted into lumen #3 and pass through the lumen #3. The folding point or bending point F2 of the RL-Paired wire P2 is placed between the two mouths of two lumens #2 and #3, preferably F2 is located at the middle point between the two mouths of the two lumens #2 and #3. For P3, Rp3 may be inserted into and pass through lumen #3, and Lp3 may be inserted into and pass through lumen #3. Folding point F3 is placed between the two mouths of two lumens #3 and #4, preferably at the middle point there between. For P4, Rp4 and Lp4 may be inserted into and pass through lumens #4 and #5, respectively, and F4 is placed between the two mouths of two lumens #4 and #5, preferably at the middle point there between. In a similar fashion, Rp5 and Lp5 may be inserted into and pass through lumens #5 and #6, respectively, and F5 is placed between the two mouths of two lumens #5 and #6, preferably at the middle point there between. Rp6 and Lp6 may be inserted into and pass through lumens #6 and #1, respectively, and F6 is placed between the two mouths of two lumens #6 and #1, preferably at the middle point there between. The number of wire-accepting lumens may be no less than the number of wires. The number of wire-accepting lumens may be equal to the number of wires. For example, an optional central lumen #7 in parallel with lumens #1~#6 may be included in bundler 1400, not for accepting any RL-Paired wire, but for e.g. control wire or pull/push wire 19 to pass through, if needed. After RL-Paired wires P1~P6 are properly placed in lumens #1~#6 as described above, a liquid adhesive material may be filled into or dropped into lumens #1~#6. After the liquid adhesive material is solidified, RL-Paired wires P1~P6 will be permanently glued and fixed to multi-lumen bundler 1400.

Figure 15:
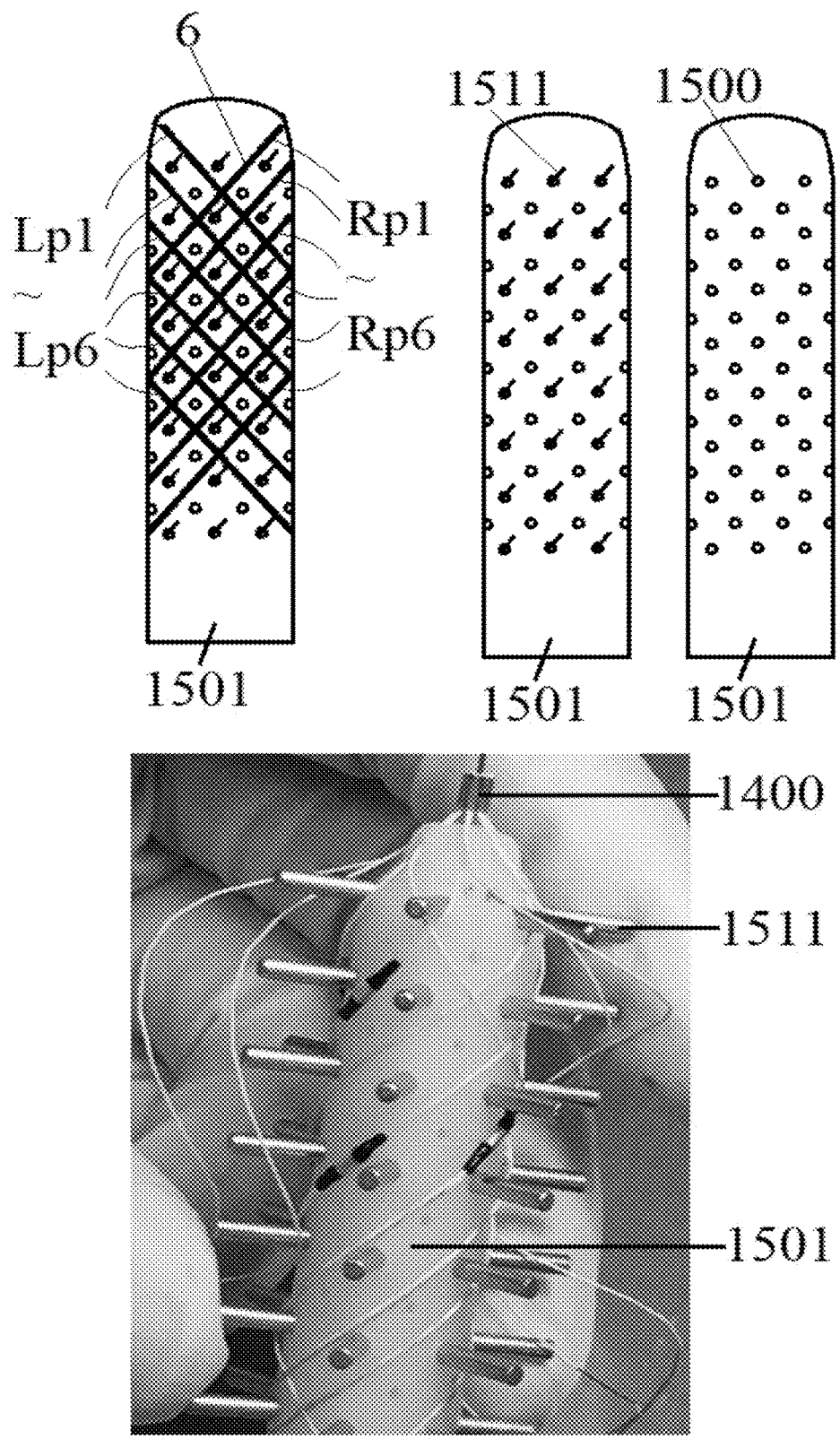
FIG. 15 illustrates the using of a bobbin and a multi-lumen bundler in weaving wire helixes plainly or bi-axially into a tubular structure in accordance with an exemplary embodiment.

When step (ii), i.e. weaving the wire helixes plainly or bi-axially into a tubular structure as the carrier, is implemented, a bobbin may be used as a scaffold. As shown in FIG. 15, a bobbin 1501 has an array of holes 1500 on it, for pins 1511 to insert in. Between any two pins 1500, or two rows of pins 1500, a wire such as one of P1~P6 may be wound. The pins 1500 may function as flanges for bobbin 1501. Multi-lumen bundler 1400 may optionally be used with bobbin 1501. When it is used, multi-lumen bundler 1400 with loose RL-Paired wires P1~P6 is placed on top tip of the bobbin 1501, and functions as the start point of the weaving process. After the weaving process is completed, pins 1511 are removed from bobbin 1501, leaving behind a tubular structure as the carrier of the invention.

EXAMPLES

The following examples are to evaluate the effects of multi-electrode catheter-based renal denervation (RDN) on insulin sensitivity and glucose metabolism in a type 2 diabetes mellitus (T2DM) canine model. Abbreviations include AKT=protein kinase B, Ang II=angiotensin II, BRDN=bilateral renal denervation, BUN=blood urine nitrogen, Cr=creatinine, G6Pase=glucose-6-phosphatase, HFD=high-fat diet, HOMA-IR=homeostasis-model assessment of insulin resistance, HPLC=high-pressure liquid chromatography, InsR=insulin receptor, LRDN=left renal denervation, NCD=normal-chow diet, PEPCK=phosphoenolpyruvate carboxykinase, RDN=renal denervation, SHAM=sham operation, STZ=streptozotocin, and T2DM=type 2 diabetes mellitus.

A total of 33 beagles (10-11 months old, of either sex) were provided by the Animal Center of Southeast University. They were housed in individual cages and subjected to controlled conditions (20-24° C. temperature, 40%-70% humidity, and 12 h: 12 h light-dark cycle), and with free access to water. The Guide for the Care and Use of Laboratory Animals was followed, and the study completely conformed to the National Health and Medical Research Council of China on Animal Experimentation and was approved by the Animal Ethics Committee of Southeast University.

Figure 16:
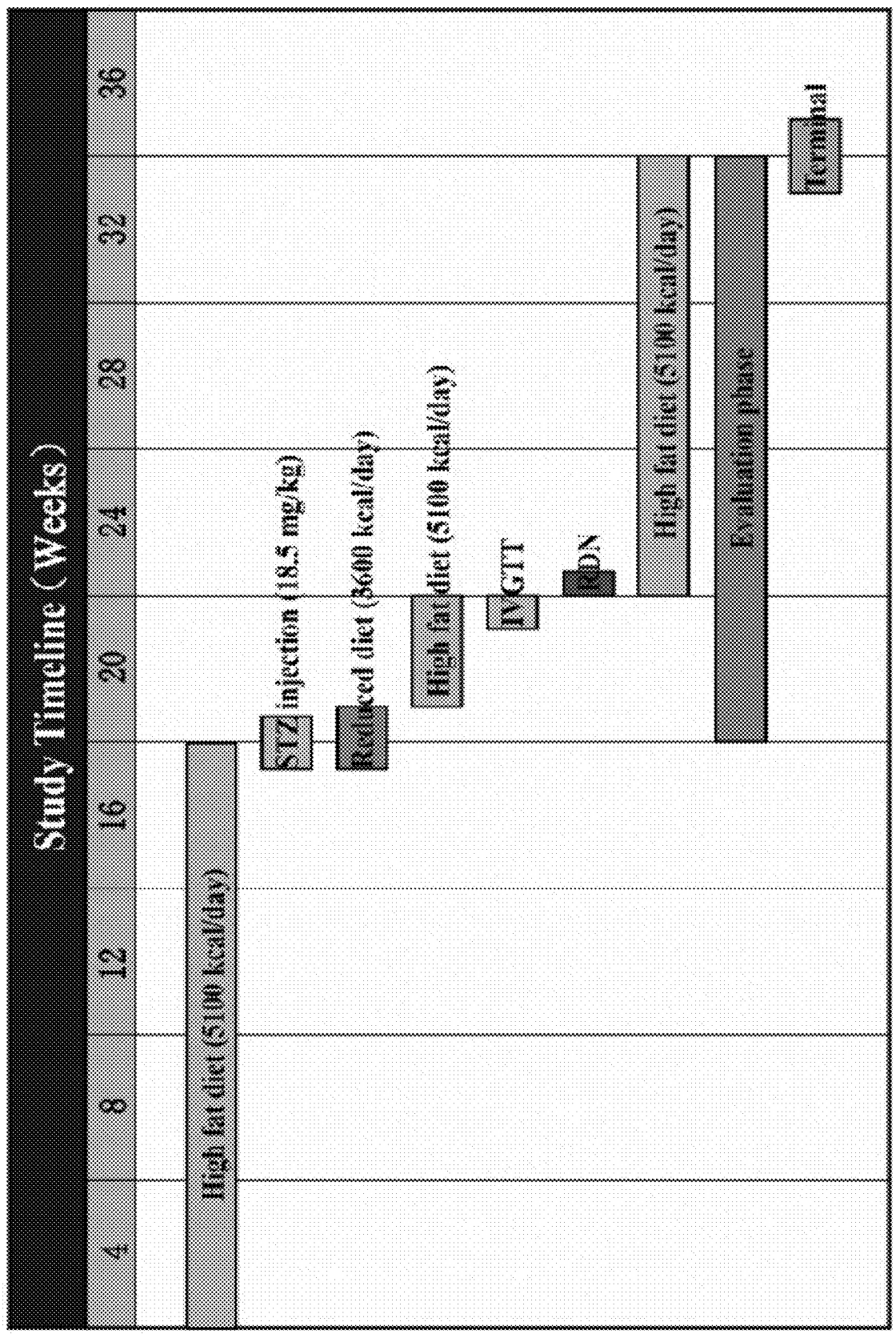
FIG. 16 shows a study timeline on a diabetes model in accordance with an exemplary embodiment of the present invention.

With respect to study timeline, baseline (W0) assessments of body weight and fasting blood levels were performed on all of the animals while they were on a normal-chow diet (NCD; 3,600 kcal/d, 27% protein, 38% carbohydrate, and 35% fat). The dogs were then fed a high-fat diet (HFD; 5,110 kcal/d, 20% protein, 27% carbohydrate, and 53% fat) for 16 weeks (W16). Subsequently, the animals received 18.5 mg/kg streptozotocin (STZ) solution via intravenous injection (21) and reduced food intake for the following week, were fed the HFD for an additional 3 weeks, and then subjected to an intravenous glucose tolerance test at 4 weeks after STZ (W20) to confirm that the T2DM model developed successfully. The 33 dogs were then equally randomized into 3 groups: bilateral renal denervation (BRDN) group, left renal denervation (LRDN) group, and sham operation (SHAM) group. The procedure was performed on all of the animals, which were subsequently fed the HFD for another 12 weeks (W32). FIG. 16 illustrates the study timeline: Baseline assessments of body weight and fasting blood were performed on all of the animals while they were on a normal-chow diet. Then the dogs were fed a HFD for 16 weeks. After that, they received 18.5 mg/kg STZ solution via intravenous injection and reduced food intake for the following week, and then were fed the HFD for an additional 3 weeks, followed by an intravenous glucose tolerance test (IVGTT) four weeks after STZ. At week 20, the procedure was performed on all of the dogs, and they were fed the HFD for another 12 weeks after the procedure.

Body weight and blood biochemistry were measured at baseline, 20 weeks, and 32 weeks, and renal angiography and computerized tomographic (CT) angiography were determined before the procedure and 1 month, 2 months, and 3 months after the procedure. For blood biochemistry, blood samples were collected from the lateral hind legs at W0, W20, and W32. Plasma triglyceride, total cholesterol, low-density lipoprotein, blood urine nitrogen (BUN), creatinine (Cr), and fasting plasma glucose were quantified by using commercially available kits (Rongsheng Biotech, Shanghai, China). Fasting insulin was measured with the use of a radioimmunoassay kit (Academy of Atomic Energy, Beijing, China). Homeostasis-model assessment of insulin resistance (HOMA-IR) was calculated with the use of the following equation: (fasting plasma glucose [in mIU/mL])×(fasting insulin [in mmol/L])/22.5. The serum level of noradrenaline was measured with the use of a commercial enzyme-linked immunosorbent assay kit (Titerzyme Kits, Michigan), and angiotensin II (Ang II) was measured with the use of a radioimmunoassay kit (Beijing Chemclin Biotech Co, Beijing, China), according to the manufacturers' specifications.

Figure 17:
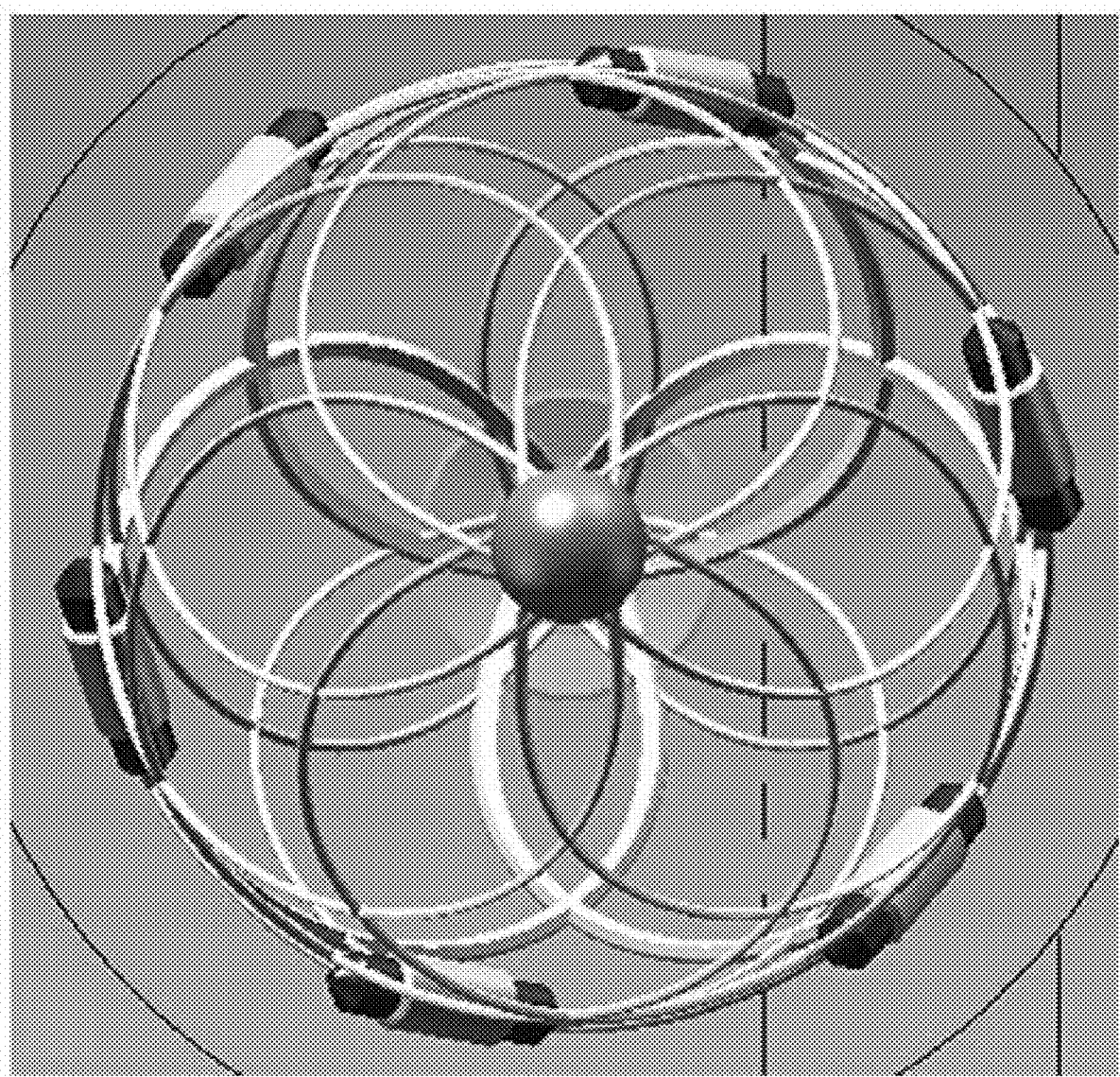
FIG. 17 shows a multi-electrode RDN catheter placed within a renal artery in accordance with an exemplary embodiment of the present invention.

For the renal denervation, the canines were fasted overnight before the procedure. Then, 0.05 mg/kg atropine was administered intravenously and the animals were anesthetized with the use of 20-30 mg/kg pentobarbital sodium via intravenous injection, which was supplemented as needed during the procedure. All animals had electrode patches placed before scrubbing and sterile draping before the procedure. The right femoral artery was punctured and an 8-F introducer sheath was inserted into the artery; then 100 U/kg heparin was injected through the sheath. Angiography of each renal artery was performed with the use of an 8-F JR4.0 guiding catheter (Boston Scientific, Massachusetts). Heparin (3,000 IU) was administered after catheterization. A multiple-electrode RDN catheter of the invention (from Shanghai Golden Leaf Med-Tec Co, Shanghai, China), which has 6 electrodes helically placed on a net structure that can manually expand and contract, was used in this study. As shown in FIG. 17, the multi-electrode RDN catheter has 6 electrodes helically distributed on a net structure (an embodiment of carrier 6). The ablation electrodes can expand according to the renal artery diameter, and they can press against the artery wall if a surgeon draws and rotates the catheter basket.

A test procedure was performed with the use of low-energy radiofrequencies to assess the adherence of the electrodes onto the blood vessel wall, judged by temperature and impedance changes: temperature ~37° C. and impedance <400Ω. Denervation was controlled by setting the temperature limit at 60° C. and the time at 1 minute for each electrode. Impedance was also monitored and limited up to 400Ω. For the BRDN group, the procedure was repeated on the contralateral renal artery; for the LRDN group, RDN was performed on left renal artery only, and denervation energy was not applied to the right renal artery; for the SHAM group, the same procedure was performed except that denervation energy was not delivered to either renal artery. Immediately after the procedure, renal angiography was performed to determine if there were significant stenoses (>75%), renal artery spasms, or any other abnormalities. After the procedure, 40 mg gentamicin (Jinan Limin Pharmaceutical Co, China) was intramuscularly injected for the first 3 days to prevent potential infection. Follow-up renal angiography and computerized tomographic (CT) angiography were performed on all animals at 1, 2, and 3 months after the procedure.

Regarding end points, the primary effectiveness endpoint was the mean change in fasting plasma glucose from baseline to 3 months in the RDN groups compared with the SHAM group. The study was also powered for assessment of secondary efficacy end points of the changes in mean fasting insulin and HOMA-IR at 3 months. The primary safety end point was a composite of major adverse events, defined as death from any cause, an embolic event resulting in organ damage, renal artery or other vascular complications, or new renal artery stenosis of >75% within 3 months.

Regarding necropsy, the dogs were sacrificed by means of an overdose of pentobarbital sodium immediately after the final renal angiography and CT angiography. Both kidneys were immediately removed for noradrenaline concentration analysis. The renal tissue was placed into liquid nitrogen at −20° C. The renal tissue was homogenized, and a single sample of the homogenate was analyzed with the use of a high-pressure liquid chromatography (HPLC) instrument coupled with an electrochemical detector. The noradrenaline concentrations for each animal's left and right kidneys were averaged in the value reported. Renal arteries and livers were removed and processed for histopathology or Western blot.

For histopathologic analyses, sections of renal artery samples were divided longitudinally into 3 equal parts and labeled as proximal, middle, and distal segments, which were analyzed from each artery. Sections were cut at ~10 μm serially. Hematoxylin and eosin- and Masson trichrome-stained slides from the right and left renal arteries were assessed. Histologic slides were examined by an experienced pathologist with 30 years' experience for identification of dissection, aneurysm, thrombus, or artery rupture. In addition, the nerve fibers were examined for any destruction or deformation caused by RDN.

Western blot was used to identify the activities of gluconeogenic enzymes and insulin-signaling proteins In the Western blot analyses, immunoblotting and isolation of liver tissues were performed according to previously described procedures (see Chen W, Chang Y, He L, et al. Effect of renal sympathetic denervation on hepatic glucose metabolism and blood pressure in a rat model of insulin resistance. J Hypertens 2016; 34:2465-2474). Then the blots were incubated with primary antibody, including glucose-6-phosphatase (G6Pase) (ab83690, 1:1,000 dilution), phosphoenolpyruvate carboxykinase (PEPCK) (ab40843, 1:1,000 dilution), insulin receptor (InsR) (ab80527, 1:1,000 dilution), phospho-InsR (ab105180, 1:1,000 dilution), protein kinase B (AKT) (ab106693, 1:1,000 dilution), phospho-AKT (ab66138, 1:1, 000 dilution), and β-actin (ab8226, 1:1,000 dilution; all from Abcam, Cambridge, United Kingdom) overnight at 4° C. Following 3 consecutive 5-minute washes in Tris-buffered saline solution containing 0.1% Tween-20 (TBST), blots were incubated with horseradish peroxidase-conjugated secondary antibody (1:1,000 dilution; Invitrogen, New York) for 1 hour at room temperature. After 2 washes in TBST and a final wash in Tris-buffered saline solution, the blots were scanned with the use of the Odyssey Infrared imaging system (Li-Cor Biosciences, Nebraska), and Quantity One analysis software (Bio-Rad, California) was used to quantify the antigen-antibody complexes.

Continuous data were expressed as mean±SD. Statistical analyses were performed with the use of SPSS 17.0 software, with the level of significance at P≤0.05. All continuous data were tested for normality and homogeneity of variance. A 2-way repeated-measures analysis of variance (ANOVA) with Bonferroni correction was performed to compare the data across groups. A one-way ANOVA was used for comparison within groups across the baseline, pre-procedure, and 3-month post-procedure time points.

The same procedure and dose of anesthetization were followed, but 1 dog in the SHAM group and 1 in the BRDN group died 10 minutes after anesthetization and before the RDN procedure. Therefore, there were 10 dogs each in the SHAM and BRDN groups and 11 in the LRDN group. HFD feeding and STZ injection succeeded, leading to canine models of T2DM at 20 weeks. FIG. 18 shows the Diabetes Mellitus Model Development in the SHAM, LRDN, and BRDN groups. Referring to FIG. 18, data are presented as mean±SD; SHAM represents sham operation; LRDN represents left renal denervation; BRDN represents bilateral renal denervation; TG represents triglyceride; TC represents total cholesterol; LDL represents low-density lipoprotein; FPG represents fasting plasma glucose; Fins represents fasting insulin; HOMA-IR represents homeostasis-model assessment of insulin resistance; NE represents noradrenaline; Ang II represents angiotensin II; BUN represents blood urine nitrogen; and Cr represents creatinine.

Renal tissue noradrenaline concentrations in the SHAM group, the LRDN group, and the BRDN group were 585.5±99.1 pg/g, 187.7±47.5 pg/g, and 66.9±17.5 pg/g, respectively. Compared with the SHAM group, renal noradrenaline concentrations in the LRDN and BRDN groups significantly decreased (both P<0.0001), and renal noradrenaline content in the BRDN group was significantly lower than in the LRDN group (P<0.0001).

Figure 19:
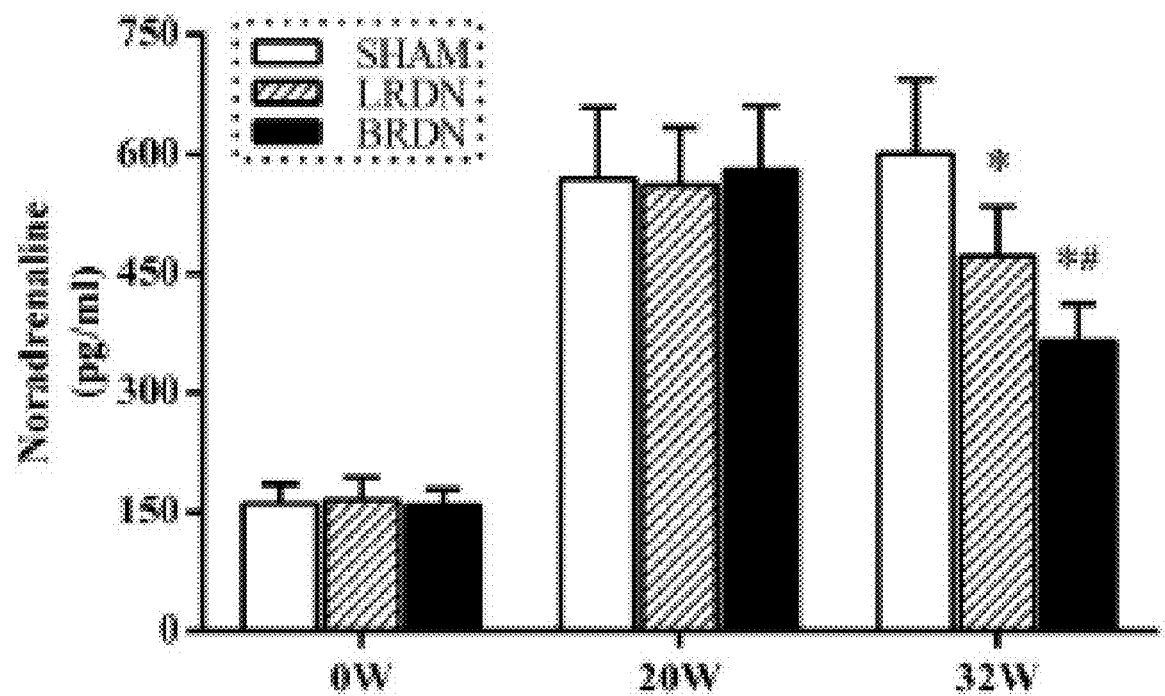
FIG. 19 shows the changes in noradrenaline before and after a procedure at week 20 in accordance with an exemplary embodiment of the present invention.
Figure 20:
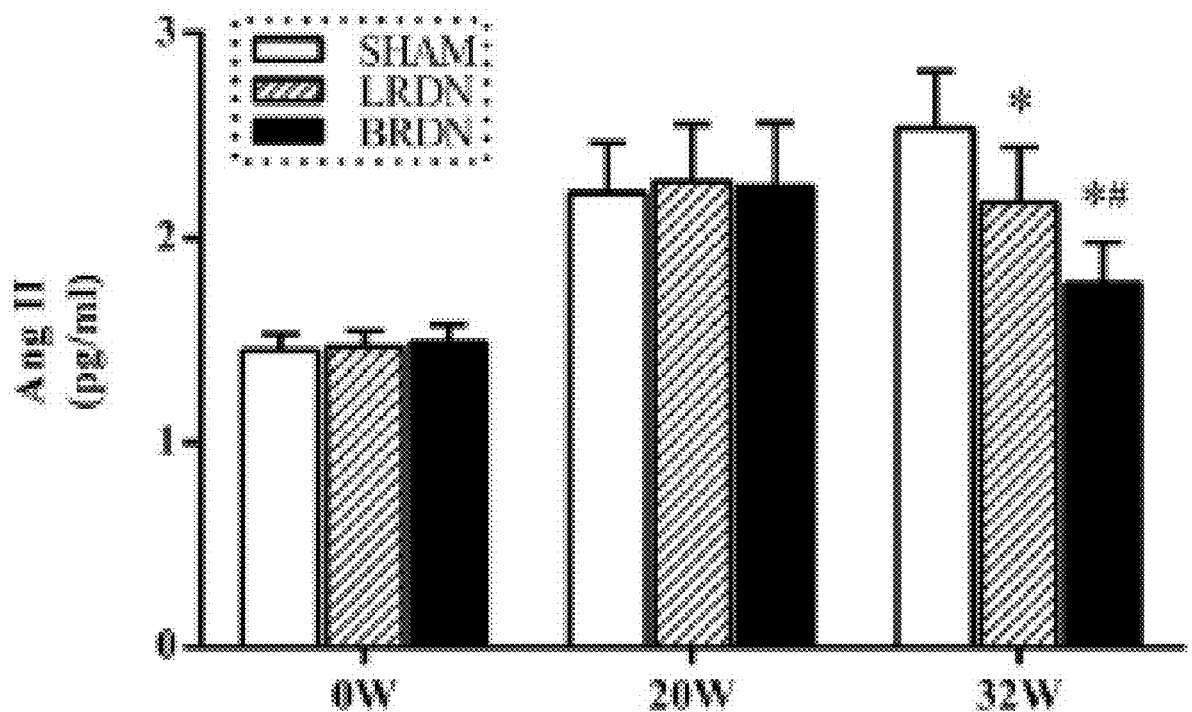
FIG. 20 shows changes in Ang II before and after a procedure at week 20 in accordance with an exemplary embodiment of the present invention.
Figure 21:
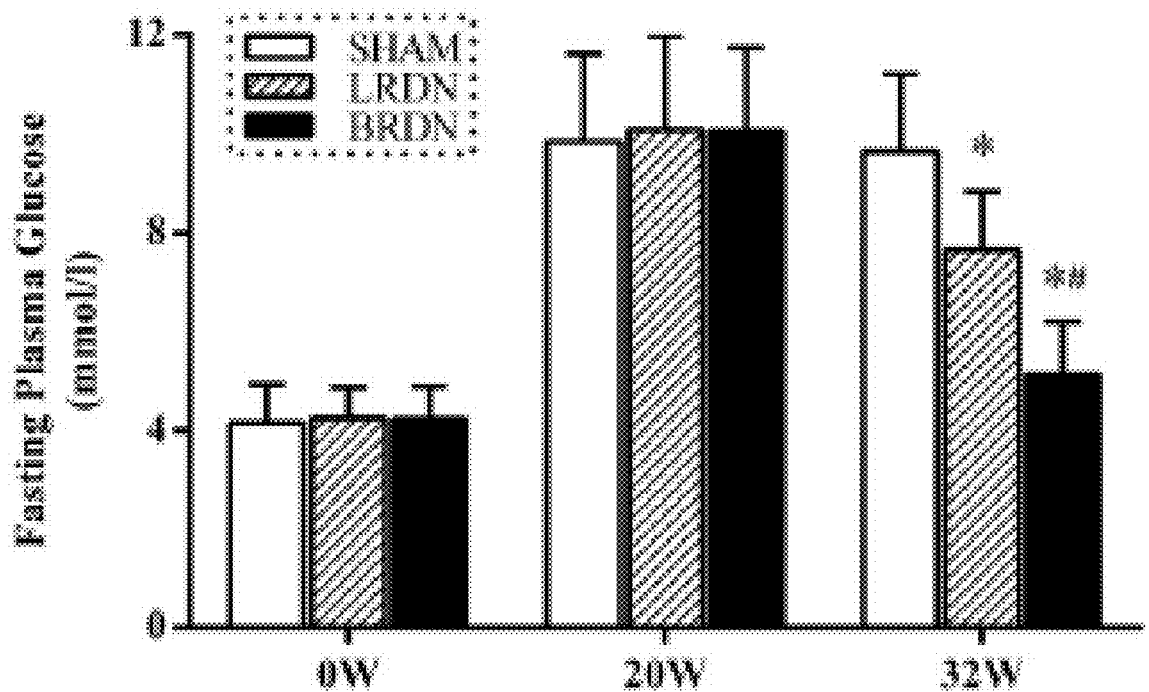
FIG. 21 shows changes in fasting plasma glucose before and after a procedure at week 20 in accordance with an exemplary embodiment of the present invention.
Figure 22:
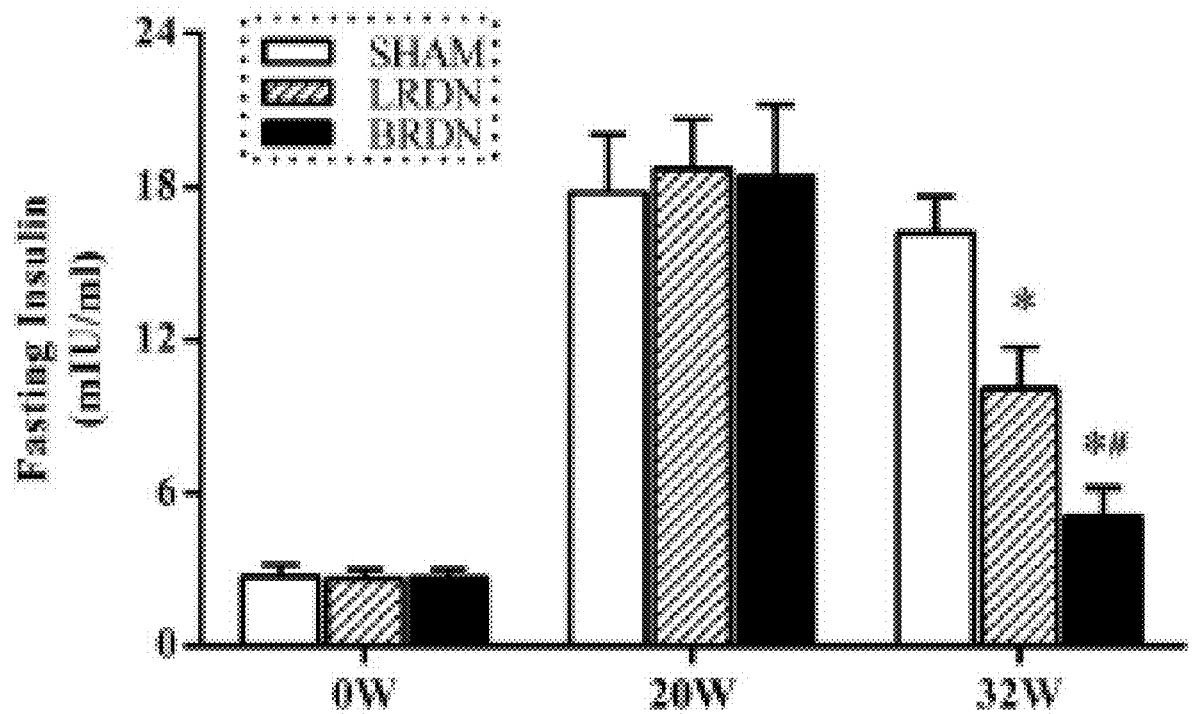
FIG. 22 shows changes in fasting insulin before and after a procedure at week 20 in accordance with an exemplary embodiment of the present invention.
Figure 23:
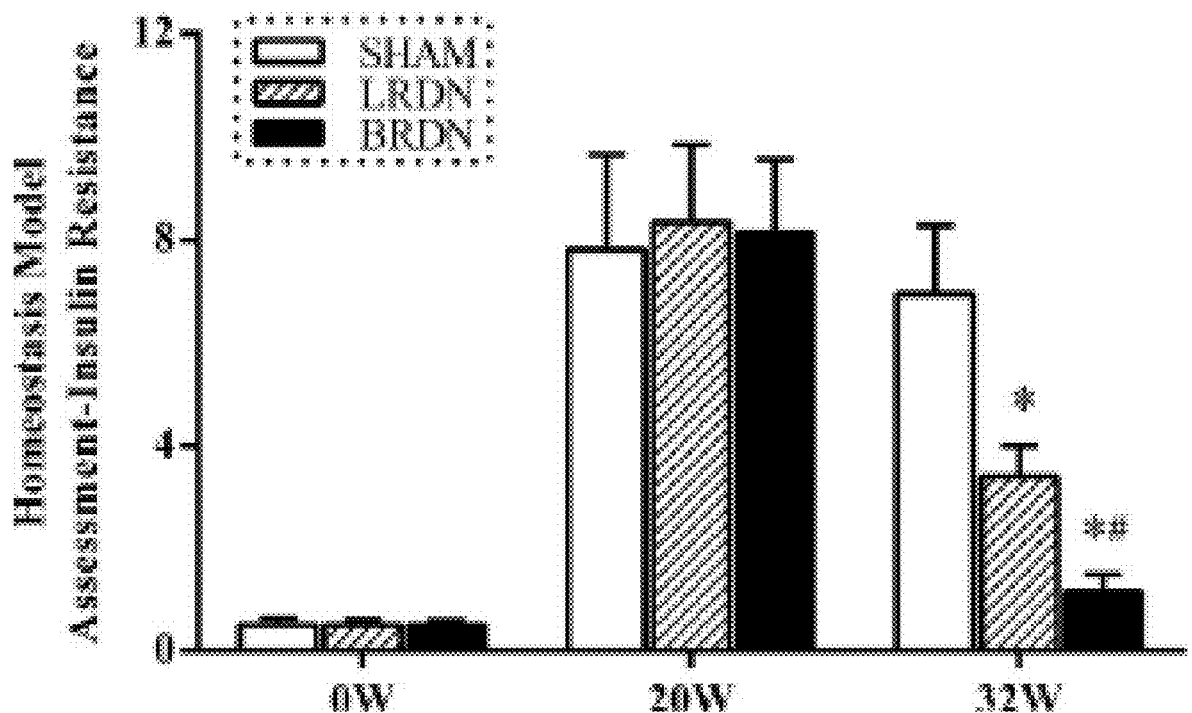
FIG. 23 shows changes in homeostasis-model assessment of insulin resistance before and after a procedure at week 20 in accordance with an exemplary embodiment of the present invention.
Figure 24:
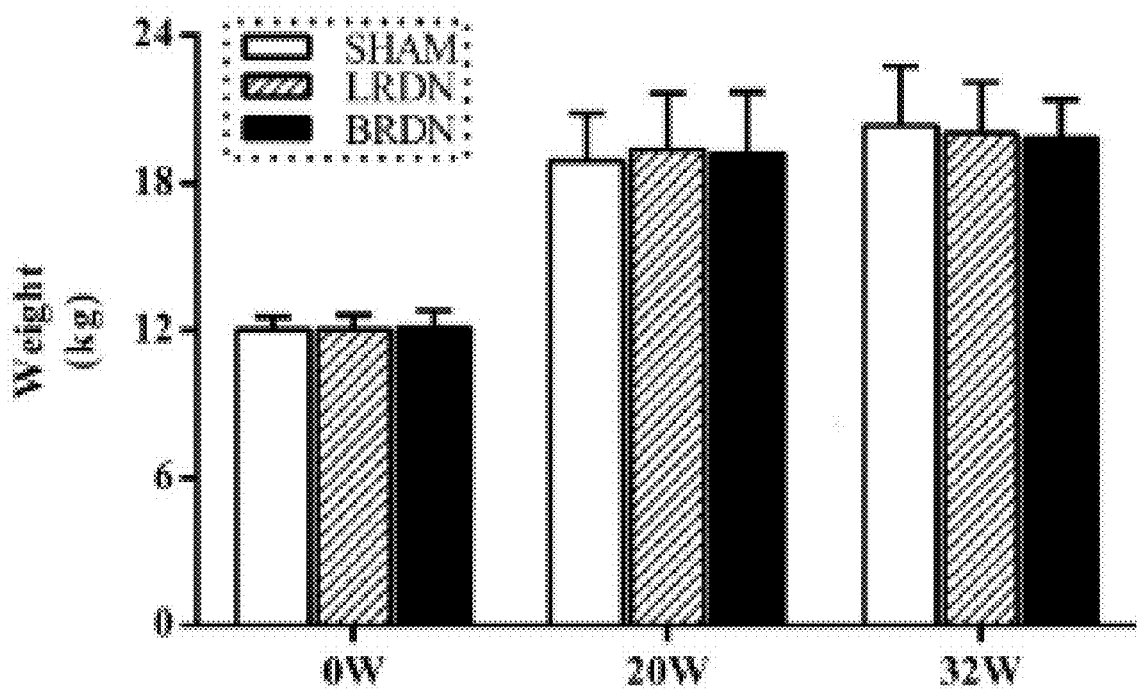
FIG. 24 shows changes in body weight among 3 groups (SHAM, LRDN, and BRDN) in accordance with an exemplary embodiment of the present invention.
Figure 25:
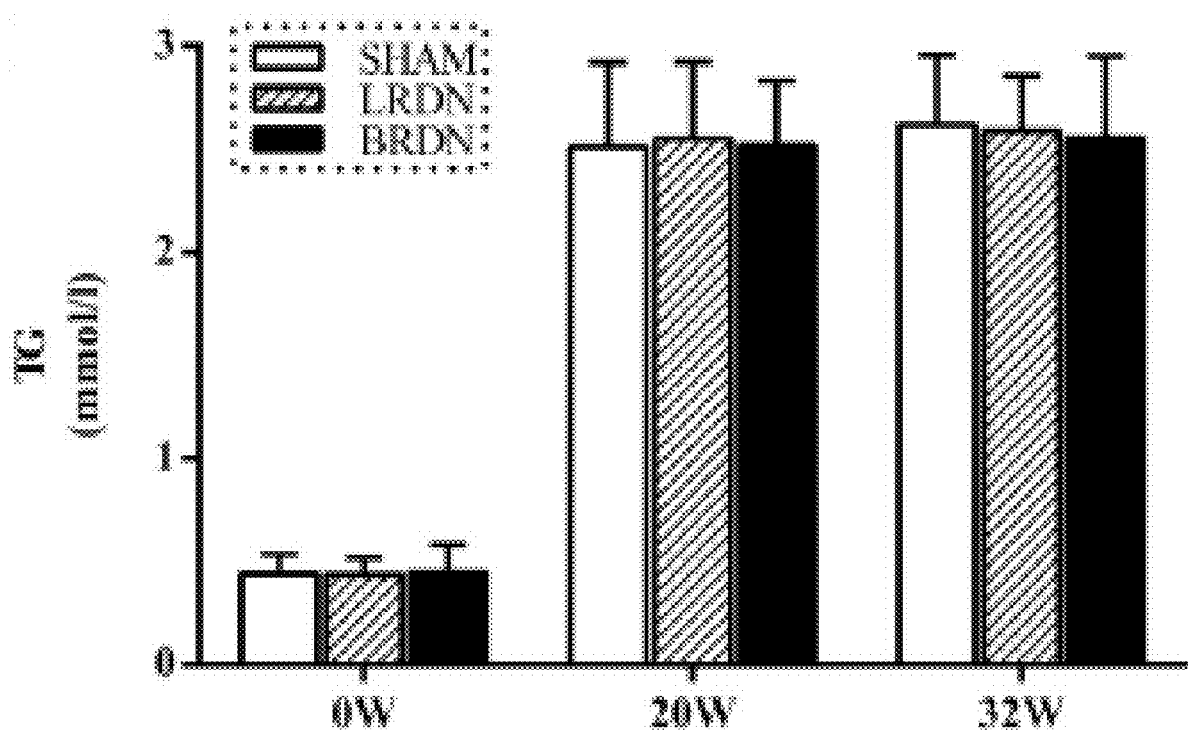
FIG. 25 shows changed in TG among the 3 groups (SHAM, LRDN, and BRDN) in accordance with an exemplary embodiment of the present invention.
Figure 26:
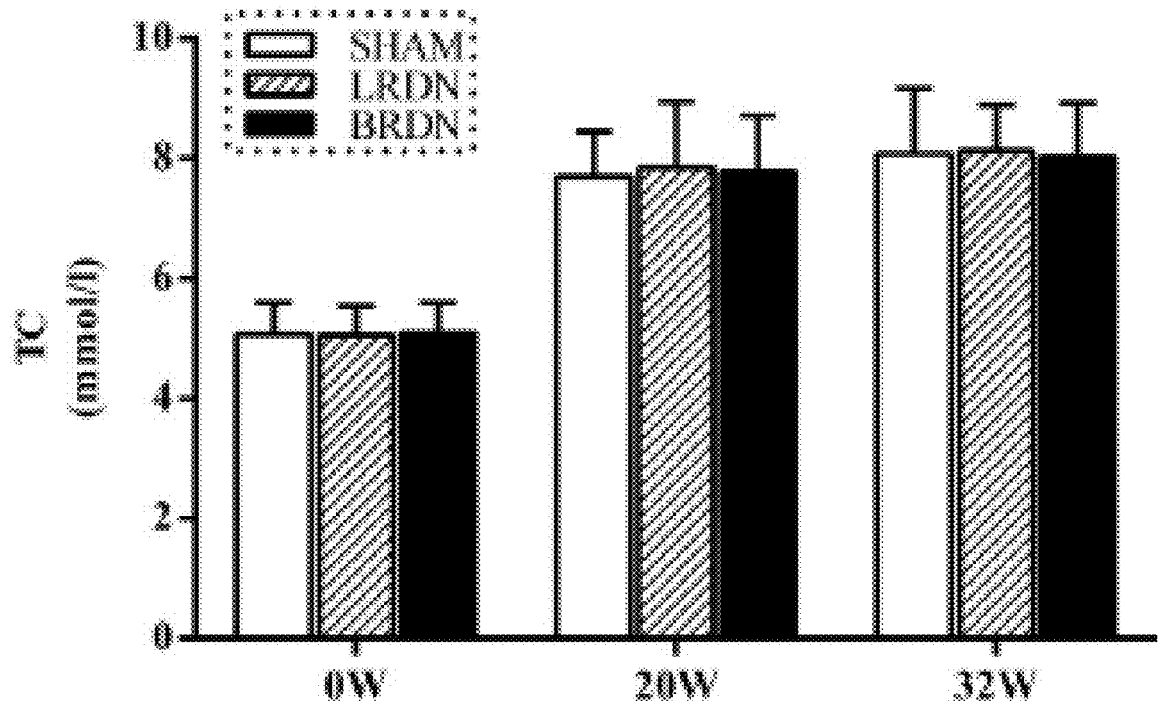
FIG. 26 shows changes in TC among the 3 groups (SHAM, LRDN, and BRDN) in accordance with an exemplary embodiment of the present invention.
Figure 27:
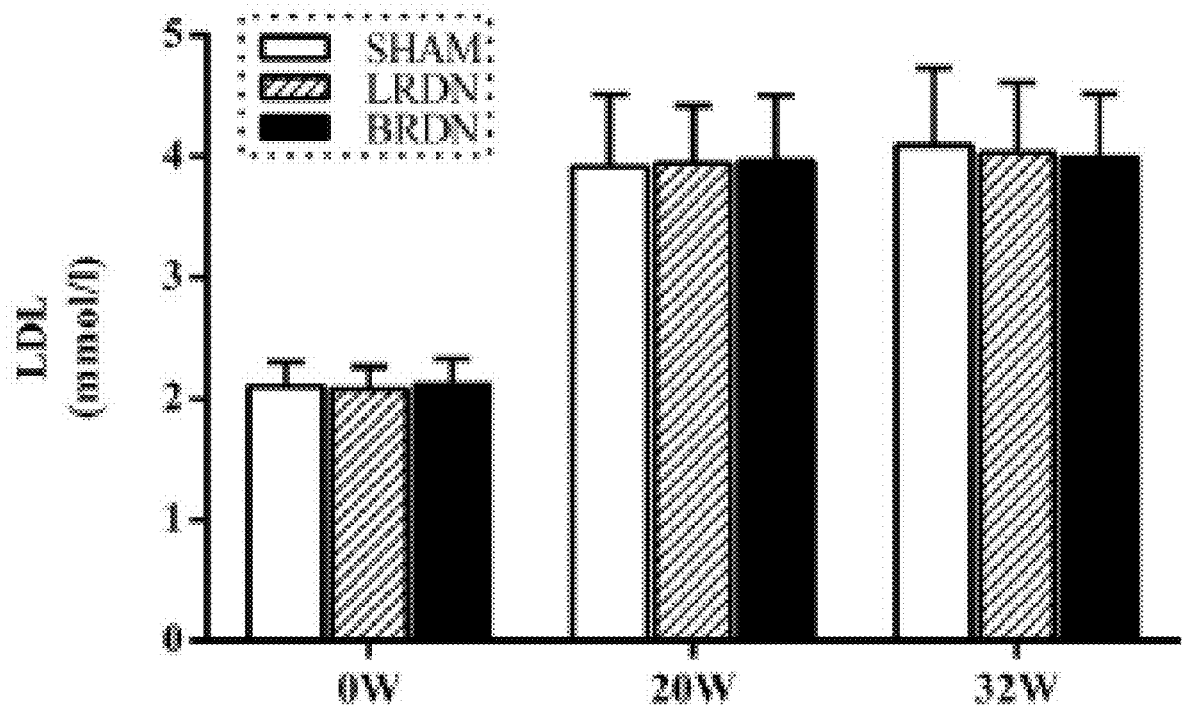
FIG. 27 shows changed in LDL among the 3 groups (SHAM, LRDN, and BRDN) in accordance with an exemplary embodiment of the present invention.
Figure 28:
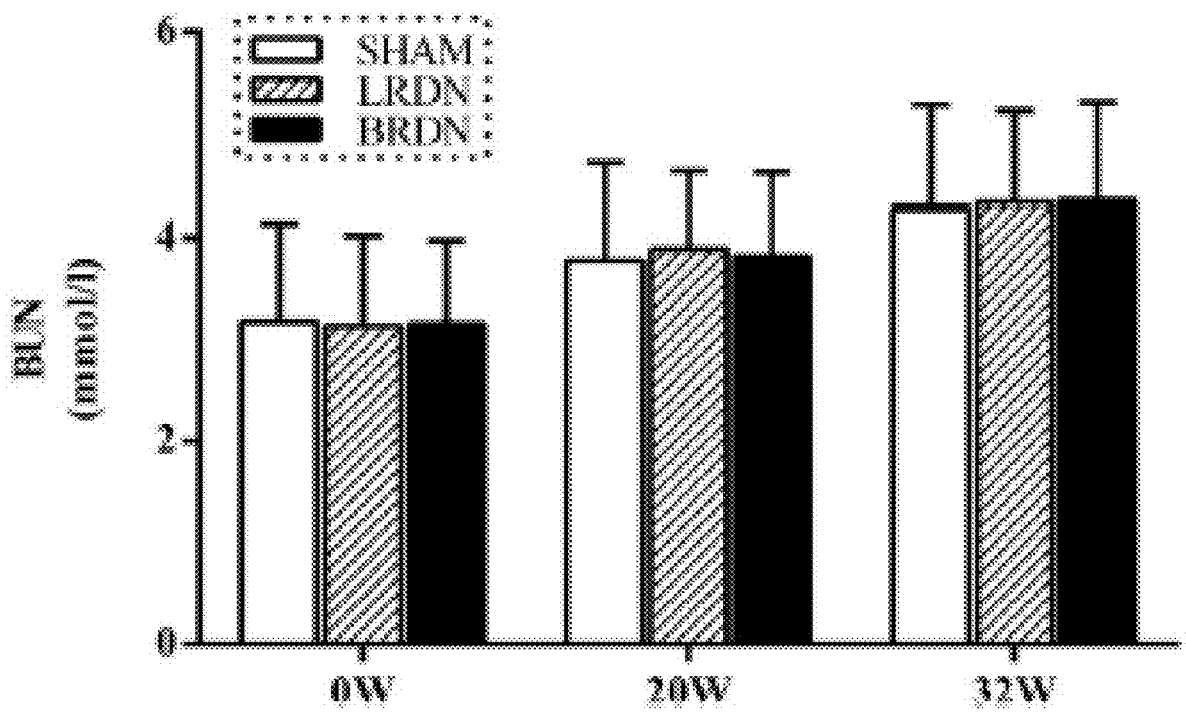
FIG. 28 shows changes in BUN among the 3 groups (SHAM, LRDN, and BRDN) in accordance with an exemplary embodiment of the present invention.
Figure 29:
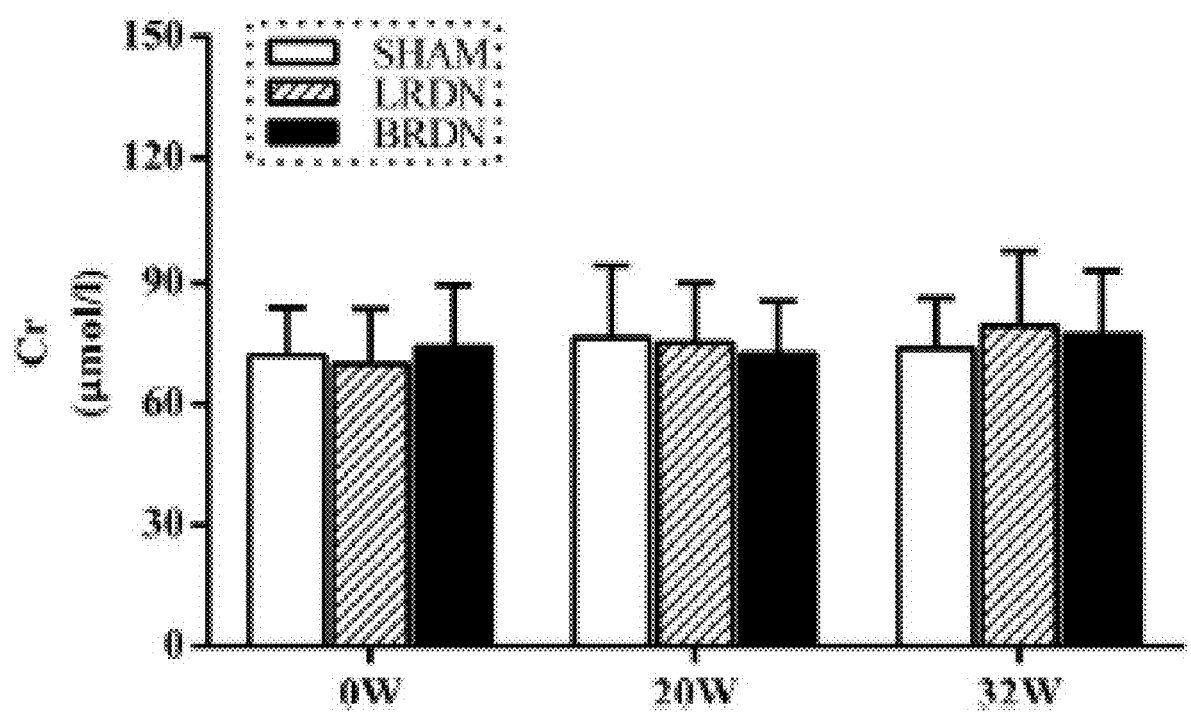
FIG. 29 shows changes in Cr among the 3 groups (SHAM, LRDN, and BRDN) in accordance with an exemplary embodiment of the present invention.

Hematologic Analyses After Procedure: Twelve weeks after RDN (W32), fasting plasma glucose (9.64±1.57 mmol/L vs 5.12±1.08 mmol/L; P<0.0001), fasting insulin (16.19±1.43 mIU/mL vs 5.07±1.13 mIU/mL; P<0.0001), HOMA-IR (6.95±1.33 vs 1.15±0.33; P<0.0001), noradrenaline (600.6±93.6 pg/mL vs 364.2±47.5 pg/mL; P<0.001), and Ang II (2.54±0.28 pg/mL vs 1.78±0.20 pg/mL; P<0.0001) levels were lower in the BRDN group than in the SHAM group. FIGS. 19-23 show the results of the hematologic analysis (*P≤0.05 compared with the SHAM group at same time point; and #P≤0.05 compared with the LRDN group at same time point). FIG. 19 shows the changes in noradrenaline before and after the procedure at week 20. FIG. 20 shows the changes in Ang II before and after the procedure at week 20. FIG. 21 shows the changes in fasting plasma glucose before and after the procedure at week 20. FIG. 22 shows the changes in fasting insulin before and after the procedure at week 20. FIG. 23 shows the changes in homeostasis-model assessment of insulin resistance before and after the procedure at week 20. Compared to W20, body weight, triglyceride (TG), total cholesterol (TC), and low-density lipoprotein (LDL) were increased at W32, and there were no significant differences among the 3 groups. FIG. 24 shows the change in body weight among the 3 groups. FIG. 25 shows the change in TG among the 3 groups. FIG. 26 shows the change in TC among the 3 groups. FIG. 27 shows the change in LDL among the 3 groups. FIG. 28 shows the change in BUN among the 3 groups. FIG. 29 shows the change in Cr among the 3 groups. Compared with the LRDN group at W32, the BRDN group had lower fasting plasma glucose (P=0.0003), fasting insulin (P<0.0001), noradrenaline (P=0.0047), and Ang II (P=0.0040) levels. Regarding HOMAIR, the BRDN group had the lowest level (although still >1), and the LRDN group's level was lower than that of the SHAM group. Regarding BUN and Cr, no statistical differences were found at W32 as compared with W20 among the 3 groups. FIG. 30 summarizes the changes after the procedure in the SHAM, LRDN, and BRDN groups, in which data are presented as mean±SD. FIG. 31 summarizes the data comparisons among the SHAM, LRDN, and BRDN Groups at W0. FIG. 32 summarizes the data comparisons among the SHAM, LRDN, and BRDN Groups at W20. FIG. 33 summarizes the data comparisons among the SHAM, LRDN, and BRDN Groups at W32. In FIGS. 31-33, data are presented as mean±SD, the symbol * denotes comparison between the SHAM and LRDN groups at the same time point, the symbol † denotes comparison between the SHAM and BRDN groups at the same time point, and the symbol ‡ denotes comparison between the LRDN and BRDN groups at the same time point.

Figure 34:
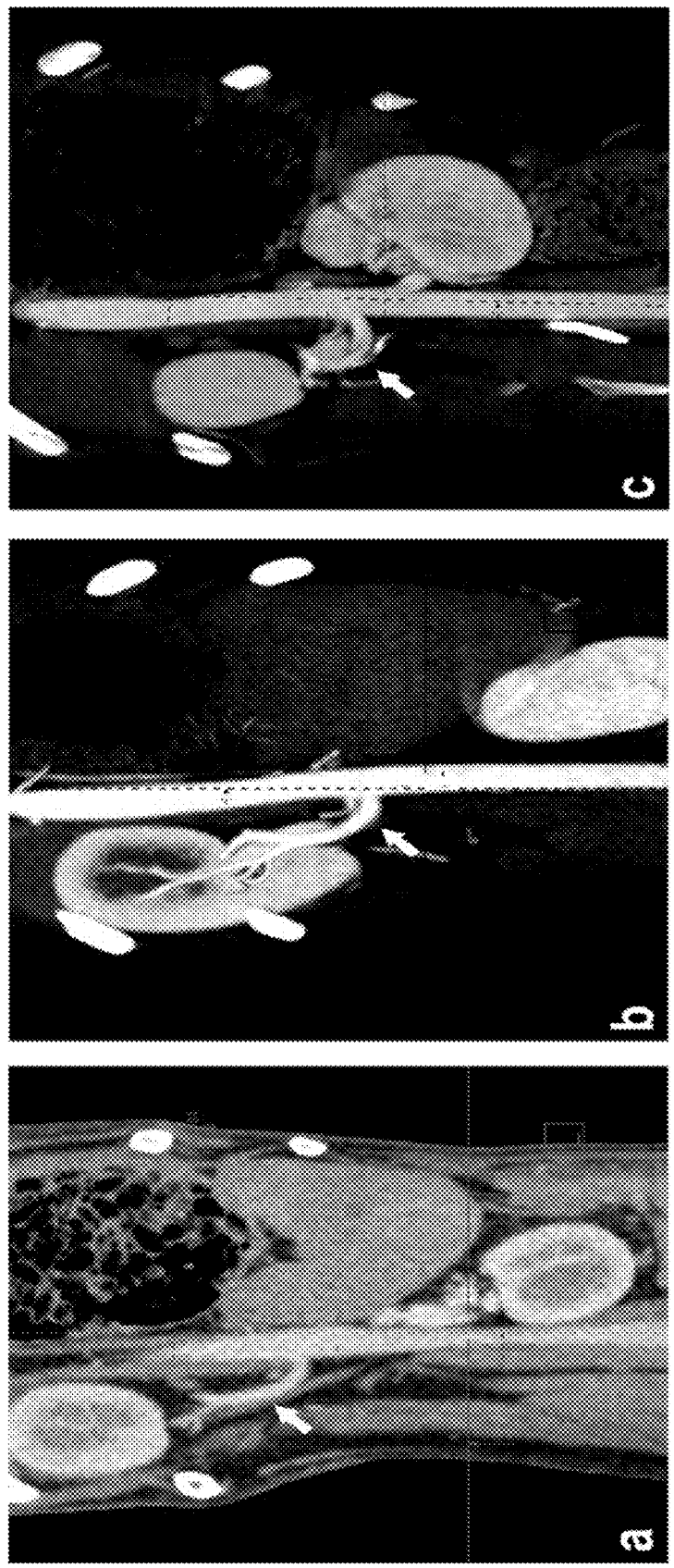
FIG. 34 displays bilateral renal arteriography and CT angiography before and after a procedure in accordance with an exemplary embodiment of the present invention.

Referring to FIG. 34, bilateral renal arteriography and CT angiography (arrows pointing to renal arterial) were performed on all of the dogs before the procedure and immediately, 1 month (panel a), 2 months (panel b), and 3 months (panel c) after the procedure. The multi-electrode RDN catheter was expanded during the procedure. A hematoma around the puncture site was observed in 5 dogs. Immediately after the procedure, all renal arteries were free of dissections and significant stenoses (>75%), and renal artery spasms were observed in 3 dogs, which resolved within 10 minutes of administering 0.1 mg nitroglycerin via intravenous injection. Three months after the procedure, no dissection, aneurysm, thrombus, or artery rupture was observed in any of the renal arteries.

Figure 35:
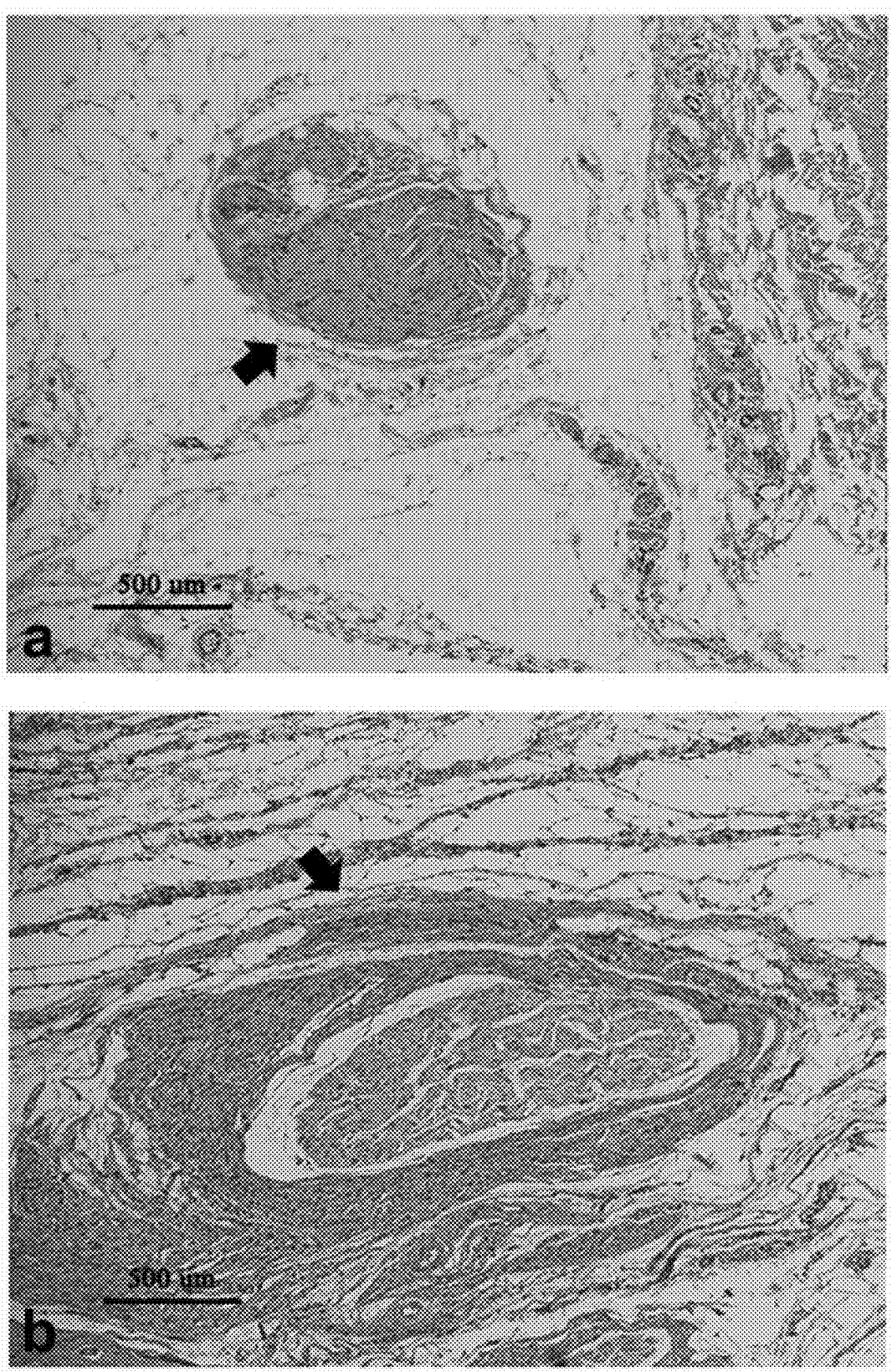
FIG. 35 shows hematoxylin and eosin staining of renal nerves in accordance with an exemplary embodiment of the present invention.

Histopathologic Analyses: FIG. 35 shows hematoxylin and eosin staining of renal nerves. Hematoxylin and eosin staining revealed foci of tunica medial fibrosis of the renal arteries, which presented as self-healing at 3 months after RDN. All treatment sites were covered by an intact layer of endothelium. There was no thromboembolism, aneurysm, or rupture of the renal arteries, and no significant stenosis or hyperplasia was found in any of the 3 groups. There was minimal multifocal intimal thickening (hyperplasia) in the 2 RDN groups. Compared with the SHAM group (see panel a: normal perineurium around nerve bundle (arrow; light microscopy, ×100)), in the RDN groups the renal sympathetic nerves were necrotic and dissolved, and no reinnervation was found (see panel b: hypercellular appearance of nerve bundle and thickened perineurium (arrow) in the renal denervation groups (light microscopy, ×100)). The RDN groups had renal interstitial edema accompanied with inflammatory cell infiltration, whereas the SHAM group had visible tubular atrophy, dilation, and cell infiltration.

Figure 36:
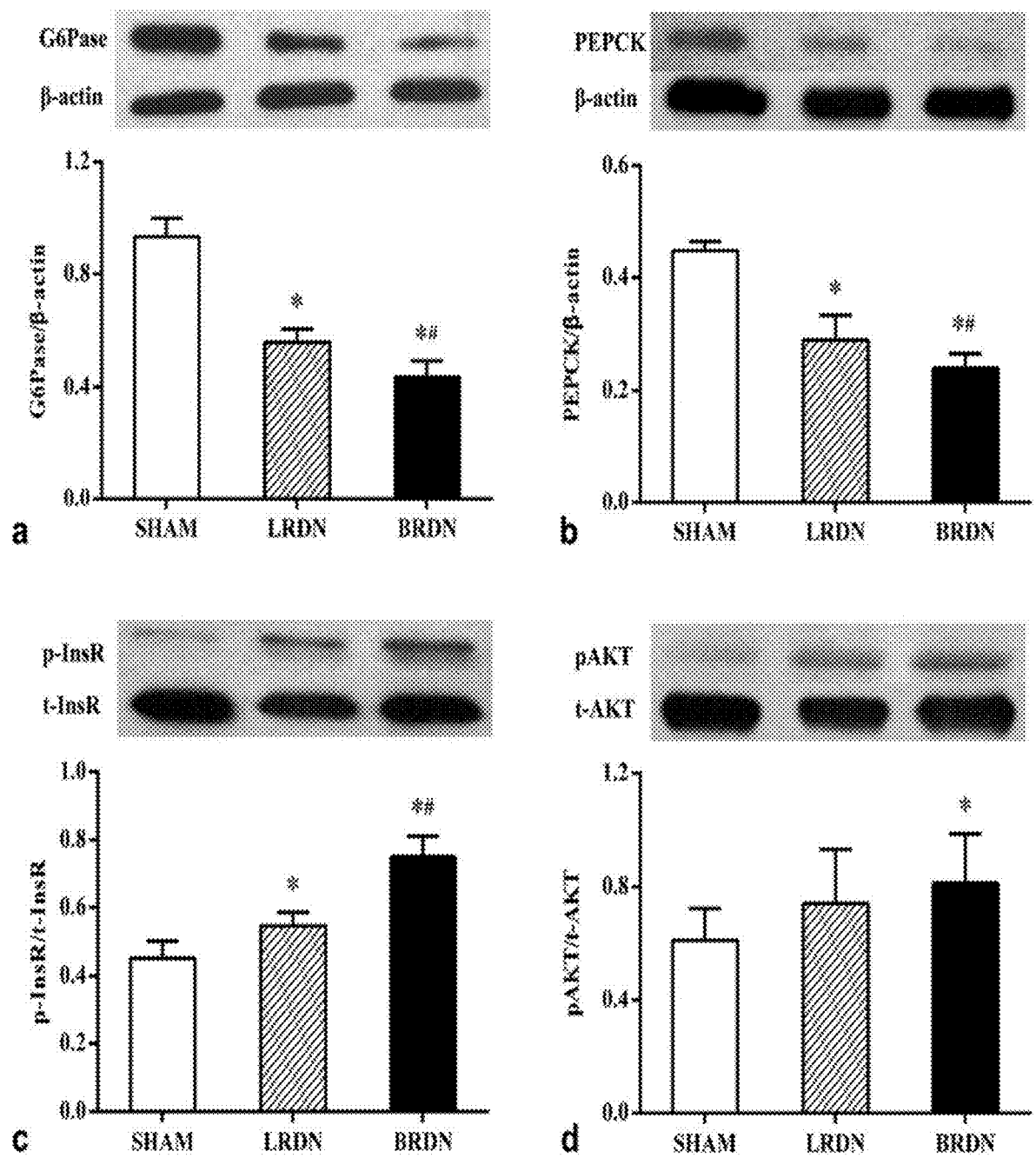
FIG. 36 shows G6Pase protein abundance, PEPCK protein abundance, phospho-insulin receptor/total insulin receptor ratio, and phospho-protein kinase B/total protein kinase B ratio after a procedure in accordance with an exemplary embodiment of the present invention.

Western Blot Analyses: FIG. 36 shows (panel a) G6Pase protein abundance, (panel b) PEPCK protein abundance, (panel c) phospho-insulin receptor/total insulin receptor ratio, and (panel d) phospho-protein kinase B/total protein kinase B ratio after the procedure. *P≤0.05 compared with the SHAM group at same time point; #P≤0.05 compared with the LRDN group at same time point. p-AKT=phospho-protein kinase B; p-InsR=phospho-insulin receptor; t-AKT=total protein kinase B; t-InsR=total insulin receptor. The livers of HFD-fed canines in both RDN groups showed decreases in G6Pase and PEPCK protein expression compared with the SHAM group, and protein expression in the BRDN group was much lower than in the LRDN group (panels a and b). The phosphorylation level of InsR was significantly improved by both BRDN and LRDN compared with the sham procedure, and phosphorylation of InsR in the BRDN group was much higher (P≤5.05) than in the LRDN group (panel c). In addition, BRDN, but not LRDN, resulted in an increase in the phosphorylation of AKT in the liver of HFD-fed dogs (panel d).

To highlight the results, fasting plasma glucose (9.64±1.57 mmol/L vs 5.12±1.08 mmol/L; P<0.0001), fasting insulin (16.19±1.43 mIU/mL vs 5.07±1.13 mIU/mL; P<0.0001), and homeostasis-model assessment of insulin resistance (HOMA-IR; 6.95±1.33 vs 1.15±0.33; P<0.0001) in the BRDN group had significantly decreased at the 3-month follow-up compared with the SHAM group. Western blot analyses showed that RDN suppressed the gluconeogenetic genes, modulated insulin action, and activated insulin receptors-AKT signaling cascade in the liver. CT angiography and histopathologic analyses did not show any dissection, aneurysm, thrombus, or rupture in any of the renal arteries.

In the present embodiment, a multi-electrode RDN catheter, which consisted of 6 electrodes helically on a net structure, was used. Surprisingly, as compared with a Symplicity Flex catheter, the catheter could use the same energy and temperature for simultaneous multipoint ablation, and the ablation electrodes could expand according to the renal artery diameter and press on the artery wall by means of drawing and rotating the catheter basket.

After RDN and 3 months of follow-up, renal angiography and CT angiography did not show any dissection, aneurysm, thrombus, or artery rupture, and histopathologic analyses showed no thromboembolism or rupture in any of the renal arteries. In addition, no statistical differences were found for BUN and Cr, showing that RDN did not impair renal function, which indicated that this multi-electrode radiofrequency ablation catheter could be safely used for RDN procedures in dogs.

The quantification of noradrenaline in renal tissue is 1 of the criterion standards for RDN efficacy in animal studies, and in the present study 3 months after the procedure, compared with the SHAM group, median renal tissue noradrenaline concentration reductions were 68% and 89% in the LRDN and BRDN groups, respectively, which was evidence of successful nerve damage.

T2DM dogs treated with the use of RDN could experience a significant decrease in fasting plasma glucose compared with sham-operated dogs. Although elevated insulin levels and HOMA-IR after RDN were still found in T2DM dogs treated with the use of RDN compared with baseline, their levels were significantly reduced compared with those who underwent the sham operation. This indicated that RDN had a favorable effect on glucose metabolism and peripheral insulin sensitivity. Compared with the LRDN group at W32, the BRDN group had lower fasting plasma glucose, fasting insulin, and HOMA-IR, which were accompanied by decreased serum noradrenaline and Ang II levels. Because no reinnervation was found after RDN and Applicants performed RDN only on the left renal artery in the LRDN group, the compensating action of the right renal sympathetic nerves might account for these differences between the BRDN and the LRDN groups.

Hepatic G6Pase and PEPCK, 2 rate-limiting enzymes, are well known for playing a critical role in gluconeogenesis and glycogenolysis. In the present embodiment, a significant reduction of hepatic PEPCK and G6Pase protein levels was found via Western blot analysis, suggesting that RDN could suppress the expression of G6Pase and PEPCK, thus resulting in improved glucose metabolism. To explore the effects of RDN on insulin signaling pathways on T2DM dogs, the phosphorylation of InsR and AKT proteins in the liver was assessed. RDN enhanced the phosphorylation of InsR, suggesting that RDN stimulated liver insulin signaling and led to an increase of insulin sensitivity. Regarding AKT, the BRDN group, but not the LRDN group, experienced an increase in the phosphorylation of AKT in the liver, and this was probably because of the compensating action of the right renal sympathetic nerves and other growth factors that might have restrained the activation of AKT. BRDN brought about a significant increase in insulin-mediated phosphorylation of AKT, which improved insulin sensitivity and glucose metabolism. Without being bound by any particular theory regarding the precise mechanisms by which RDN affected insulin sensitivity and glucose metabolism, it is believed that increased blood flow could improve the ability of cells to transport glucose through their membranes, and that RDN reduced the activity of the sympathetic nervous system, leading to an increase in the number of open capillaries and a decrease in the distance that insulin had to travel from the intravascular compartment to reach the cell membrane.

In conclusion, RDN with the use of a multi-electrode system effectively decreased gluconeogenesis and glycogenolysis, resulting in improvements in insulin sensitivity and glucose metabolism. Moreover, denervation of the kidneys has a beneficial effect on the liver.

In the foregoing specification, embodiments of the present invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicant to be the scope of the invention, is the literal and equivalent scope of the set of claims that issue from this application, in the specific form in which such claims issue, including any subsequent correction.

The invention claimed is:

1. A method for treating diabetes, a diabetes-associated condition or disorder, or symptoms thereof suffered by a subject, comprising
    (1) placing multiple electrodes within at least one renal artery of the subject and against a blood vessel wall of the at least one renal artery;
    (2) adhering a surface electrode on an external surface of the subject; and
    (3) releasing a therapeutically effective amount of radiofrequency energy through at least one of the multiple electrodes to nearby tissues, so as to increase the temperature of the nearby tissues and induce a thermal alteration of the nearby tissues,
    wherein said treating and said "therapeutically effective" refer to reversing, alleviating, inhibiting the progress of, or preventing the diabetes or the diabetes-associated condition or disorder, or the symptoms thereof in said subject, and
    wherein the method further comprises decreasing fasting plasma glucose level of the subject from 9.64 mmol/L down to 5.12 mmol/L; decreasing fasting insulin level of the subject from 16.19 mIU/mL down to 5.07 mIU/mL; decreasing homeostasis-model assessment of insulin resistance (HOMA-IR) of the subject from 6.95 down to 1.15; or damaging nerve and decreasing renal tissue noradrenaline of the subject from 585.5 pg/g down to 187.7 pg/g or 66.9 pg/g; three months after step (3) is carried out.

2. The method according to claim 1, wherein the subject includes beagles, further comprising decreasing fasting plasma glucose level of the subject from 9.64 mmol/L down to 5.12 mmol/L or decreasing fasting insulin level of the subject from 16.19 mIU/mL down to 5.07 mIU/mL, three months after step (3) is carried out.

3. The method according to claim 1, wherein the subject includes beagles, further comprising decreasing homeostasis-model assessment of insulin resistance (HOMA-IR) of the subject from 6.95 down to 1.15 three months after step (3) is carried out.

4. The method according to claim 1, wherein the subject includes beagles, further comprising damaging nerve and decreasing renal tissue noradrenaline of the subject from 585.5 pg/g down to 187.7 pg/g or 66.9 pg/g three months after step (3) is carried out.

5. The method according to claim 1, further comprising maintaining integrity of the at least one renal artery by introducing no dissection, no aneurysm, no thrombus, no rupture, and no renal function impairment in the artery, after step (3) is carried out.

6. The method according to claim 1, wherein the multiple electrodes are part of a catheter apparatus comprising at least one interstice that is defined by four wire helix segments from two immediately adjacent right-handed wire helixes and two immediately adjacent left-handed wire helixes that are plainly or bi-axially woven into each other; and wherein a therapeutic assembly wraps around only one of said four wire helix segments to stabilize the interstice.

7. The method according to claim 6, wherein the therapeutic assembly includes two terminal bodies and a main body positioned between the two terminal bodies; and wherein cross-sectional area of the main body along a plane perpendicular to the elongation direction of the wire segment being wrapped around is larger than cross-sectional areas of the terminal bodies along a plane perpendicular to the elongation direction of the wire segment being wrapped around, which are larger than a cross-sectional area of the wire segment being wrapped around along a plane perpendicular to the elongation direction of the wire segment.

8. The method according to claim 7, wherein length of the wire segment being wrapped around is maintained to be equal to, or longer than, the main body's length along the elongation direction of the wire segment being wrapped around.

9. The method according to claim 7, wherein length of the wire segment being wrapped around is maintained to be equal to, or longer than, the main body's length combined with length of one of the two terminal bodies, or total length of the two terminal bodies, along the elongation direction of the wire segment being wrapped around.

10. The method according to claim 7, wherein at least one of the two terminal bodies and the main body includes (1) one or more grooves for accommodating or guiding one or more wire helixes that slide(s) over the wire segment around which the therapeutic assembly wraps; or (2) one, two or more protrusions, wherein the gap(s) between the protrusion(s) and the wire segment around which the therapeutic assembly wraps, and the gap(s) between said protrusion(s) themselves, is(are) configured for accommodating or guiding one or more wire helixes that slide(s) over the wire segment around which the therapeutic assembly wraps.

* * * * *